United States Patent [19]

Porter et al.

[11] Patent Number: 5,103,679
[45] Date of Patent: Apr. 14, 1992

[54] METHOD AND APPARATUS FOR DETERMINING THE FUNDAMENTAL VISCOELASTIC PROPERTIES OF A MATERIAL

[75] Inventors: John P. Porter, Cuyahoga Falls; Ronald L. Dellangelo, Doylestown; Emmitt R. Harrell, Jr., Avon Lake, all of Ohio

[73] Assignee: The B. F. Goodrich Company, New York, N.Y.

[21] Appl. No.: 550,866

[22] Filed: Jul. 10, 1990

[51] Int. Cl.$^5$ .......................................... G01N 11/14
[52] U.S. Cl. ..................... 73/843.0; 73/60.0
[58] Field of Search ............... 73/841, 843, 846, 60

[56] References Cited

U.S. PATENT DOCUMENTS

| | | | |
|---|---|---|---|
| 3,494,172 | 2/1970 | Juve et al. | 73/843 X |
| 3,693,421 | 9/1972 | Karper et al. | 73/843 |
| 3,818,751 | 6/1974 | Karper et al. | 73/843 X |
| 4,535,621 | 8/1985 | Gervais et al. | 73/843 X |
| 4,559,812 | 12/1985 | Kitchen | 73/843 X |
| 4,601,195 | 7/1986 | Garritano | 73/60 |

*Primary Examiner*—Hezron E. Williams
*Assistant Examiner*—Joseph W. Roskos
*Attorney, Agent, or Firm*—Renner, Otto, Boiselle & Sklar

[57] ABSTRACT

A method of determining the fundamental viscoelastic properties of a viscoelastic material includes the steps of imparting a torsional stress in a viscoelastic material; measuring the relaxation of the torsional stress over time and converting the relaxation stress to a representative analog waveform; digitizing the representative analog waveform to produce a representative digital waveform; and, determining the frequency dependant fundamental viscoelastic properties of the material based on the shape of a portion of the representative digital waveform. To facilitate automating the method, the shape of the waveform may be analyzed to detect the start of a test, the end of the test, and whether the test is a valide test. Preferably, the fundamental viscoelastic properties of the test material are determined by converting the torque based amplitudes of the waveform to shear relaxation modulus values, such as by multiplying the torque amplitudes by the geometric form factor of the test material, and then by transforming the shear stress modulus values to frequency dependant fundamental viscoelastic properties through the known Yagii/Maekawa approximation. A related apparatus is also disclosed.

18 Claims, 35 Drawing Sheets

METHOD AND APPARATUS FOR DETERMINING THE FUNDAMENTAL VISCOELASTIC PROPERTIES OF A MATERIAL

FIELD OF THE INVENTION

This invention relates generally to an apparatus and method for measuring the fundamental viscoelastic properties of a material, and more particularly, to improvements in a Dynamic Stress Relaxometer.

BACKGROUND OF THE INVENTION

Viscoelastic materials, such as elastomers, rubbers, plastics, and the like, can be described by a number of fundamental viscoelastic properties which vary between different material types and, in fact, may vary between separate batches of the same material type. Consequently, these fundamental properties, such as the loss and storage moduli, the complex viscosity and the loss tangent, may be used to identify materials either by type or by grade. Further, these properties may also be used to predict the processing characteristics of a material.

However, heretofore many methods of determining the fundamental viscoelastic properties of materials have been time consuming, i.e., often requiring several hours, and have relied on the participation of a skilled technician to perform the test. Moreover, with many tests it is possible only to describe a few characteristics of the material, such as die swell or stress relaxation, and not actually to determine the fundamental viscoelastic properties of the material. These drawbacks have made these tests unsuitable for use on the factory floor or for use in a control system wherein the results of the test are employed to modify the composition or processing of the material.

A Dynamic Stress Relaxometer (DSR), as described in U.S. Pat. Nos. 3,693,421 and 3,818,751, has provided a relatively quick way to predict some characteristics of a material and also to at least roughly distinguish between materials and grades of materials. The disclosures of such patents hereby are entirely incorporated by reference. In a DSR test a sample of a viscoelastic material is subjected to a prescribed angular deformation thus creating shear stresses in the material. The gradual relaxation of these stresses over time is measured and plotted to provide a stress relaxation curve for the material. As the relaxation curve follows a generally exponential decay path, a number of standard measurement points along the curve are selected which have been found to yield significant information about the test specimen in a relatively short time, i.e., less than ten minutes. This information is then used to predict the die swell, processability or type or grade of the material tested. While DSR testing has been quite an advance over previous methods, it still lacked the ability to determine quantitatively the fundamental viscoelastic properties of the material.

It would be desirable to develop an improved accuracy DSR device and to combine such a DSR device with the means to interpret the results to determine the fundamental viscoelastic properties of a material.

As used herein the term "viscoelastic" is meant to include synthetic or natural rubbers, plastics, thermoplastics, elastomers and any other material that exhibits viscoelastic properties.

SUMMARY OF THE INVENTION

It is an object of the present invention to provide a fast and accurate way to measure the fundamental viscoelastic properties of a material.

It is another object of the invention to substantially automate the process of performing a dynamic stress relaxation test.

According to one aspect of the present invention, an apparatus for determining the fundamental viscoelastic properties of a viscoelastic material includes means for imparting a torsional stress in a viscoelastic material; means for measuring the relaxation of the torsional stress over time and converting the relaxation stress to a representative waveform; and processing means for determining the frequency dependant fundamental viscoelastic properties of the material based on the shape of a portion of the waveform. Preferably, the processing means includes a first dedicated processor for producing a digital representation of the waveform and a second general processor, such as an IBM compatible microcomputer for determining the fundamental viscoelastic properties from a portion of the digital representation. To facilitate automating the determination of the fundamental viscoelastic properties of the test material, the first processor examines the waveform and aborts the determination if the digital waveform is atypical of an expected waveform for a viscoelastic material subjected to a torsional stress.

According to another aspect of the present invention, a method of determining the fundamental viscoelastic properties of a viscoelastic material includes the steps of imparting a torsional stress in a viscoelastic material; measuring the relaxation of the torsional stress over time and converting the relaxation stress to a representative analog waveform; digitizing the representative analog waveform to produce a representative digital waveform; and, determining the frequency dependant fundamental viscoelastic properties of the material based on the shape of a portion of the representative digital waveform. To facilitate automating the method, the shape of the waveform may be analyzed to detect the start of a test, the end of the test, and whether the test is a valid test. Preferably, the fundamental viscoelastic properties of the test material are determined by converting the torque based amplitudes of the waveform to shear relaxation modulus values, such as by multiplying the torque amplitudes by the geometric form factor of the test material, and then by transforming the shear stress modulus values to frequency dependant fundamental viscoelastic properties through the known Yagii/Maekawa approximation.

These and other objects, advantages, features and aspects of the present invention will become apparent as the following description proceeds.

To the accomplishments of the foregoing and related ends, the invention, then, comprises and features hereinafter fully described in the specification and particularly point out in claims, the following description and the annexed drawings setting forth in detail a certain illustrative embodiment of the invention, this being indicative, however, of but one of the various ways in which the principals of the invention may be employed. It will be appreciated that the scope of the invention is to be determined by the claims and the equivalents thereof.

DETAILED DESCRIPTION OF THE INVENTION

Figure 1:
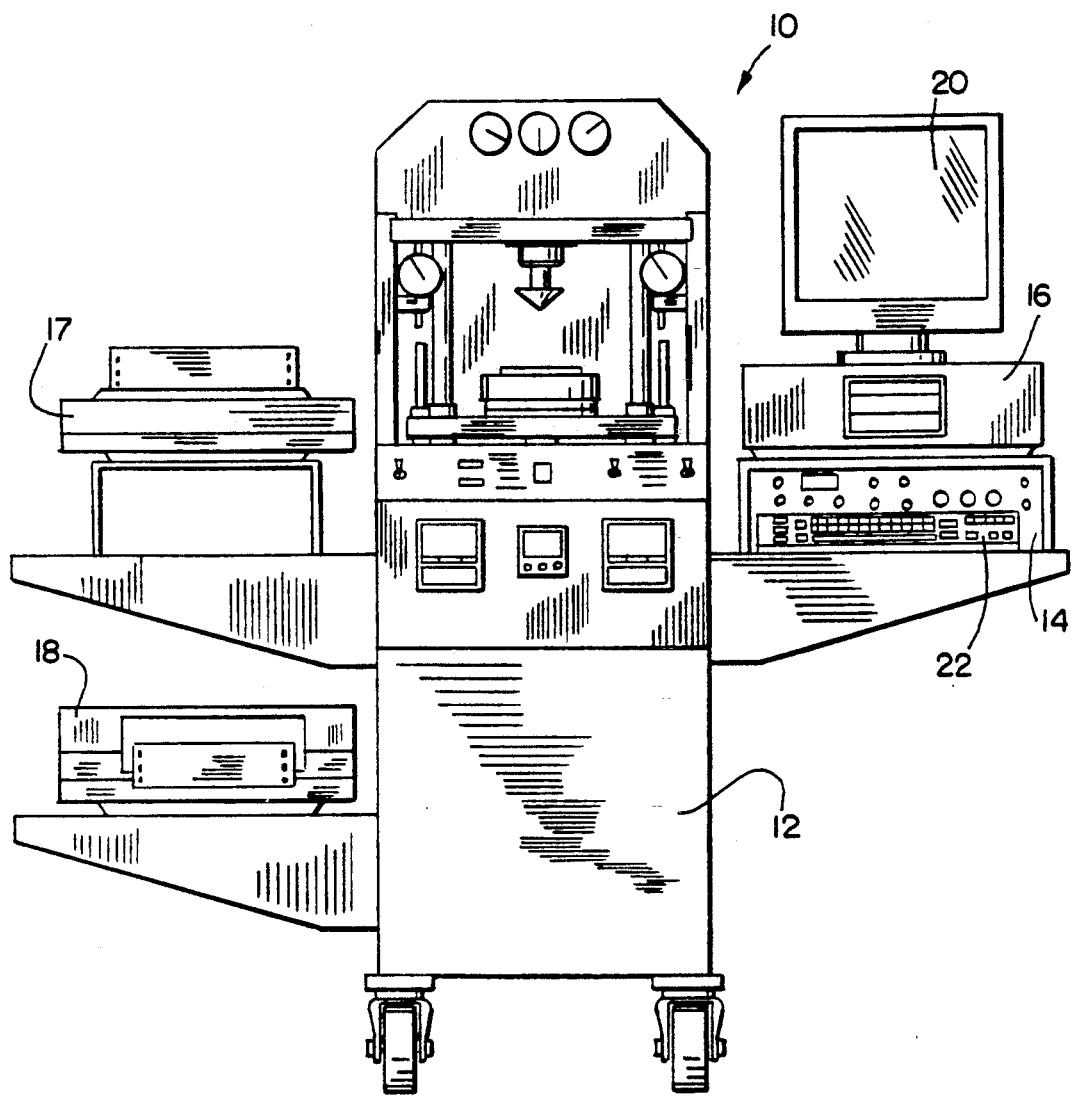
FIG. 1 is an illustration of the Dynamic Stress Relaxometer system of the present invention.
Figure 2:
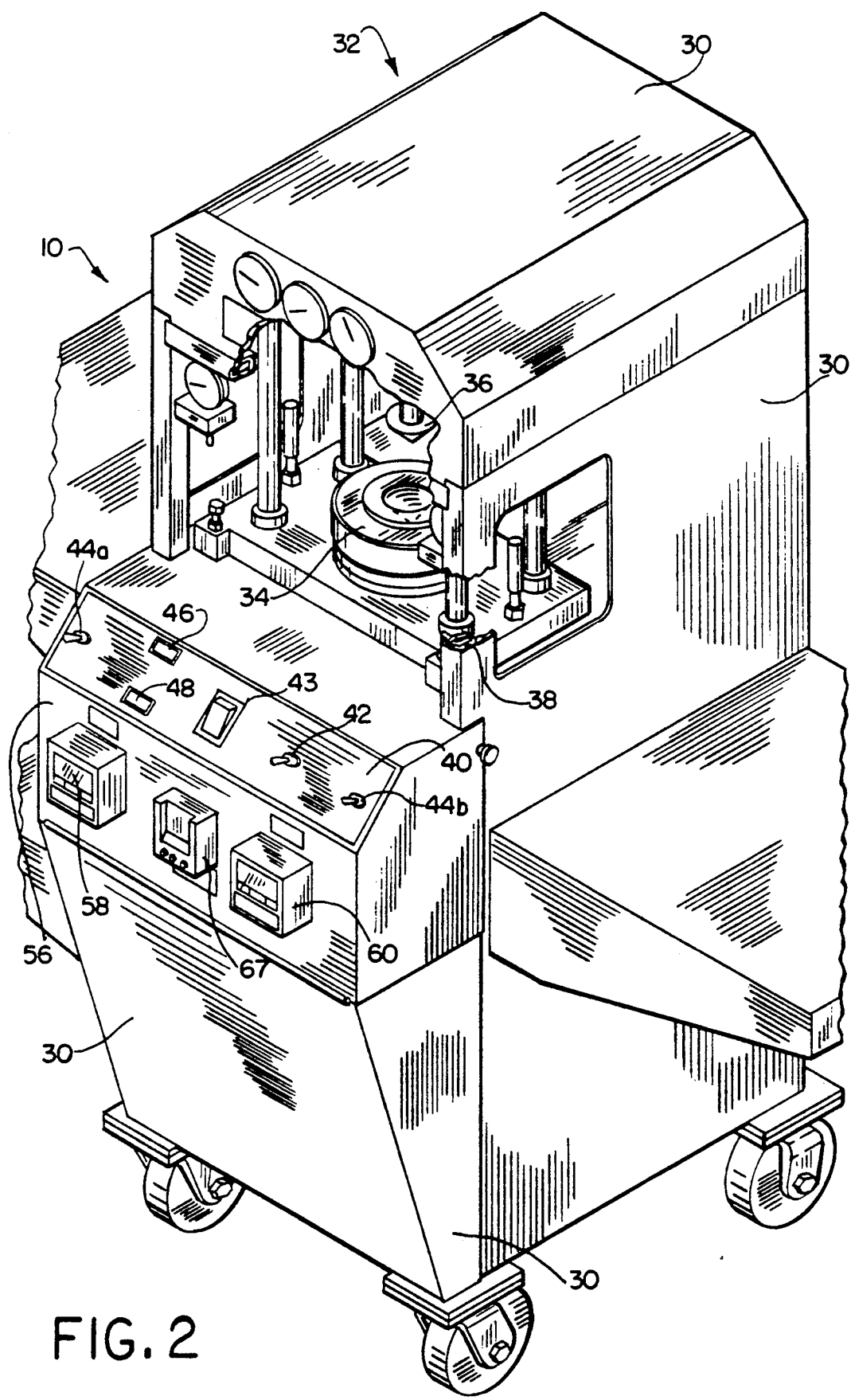
FIG. 2 is an oblique partially cutaway view of the DSR device.
Figure 3:
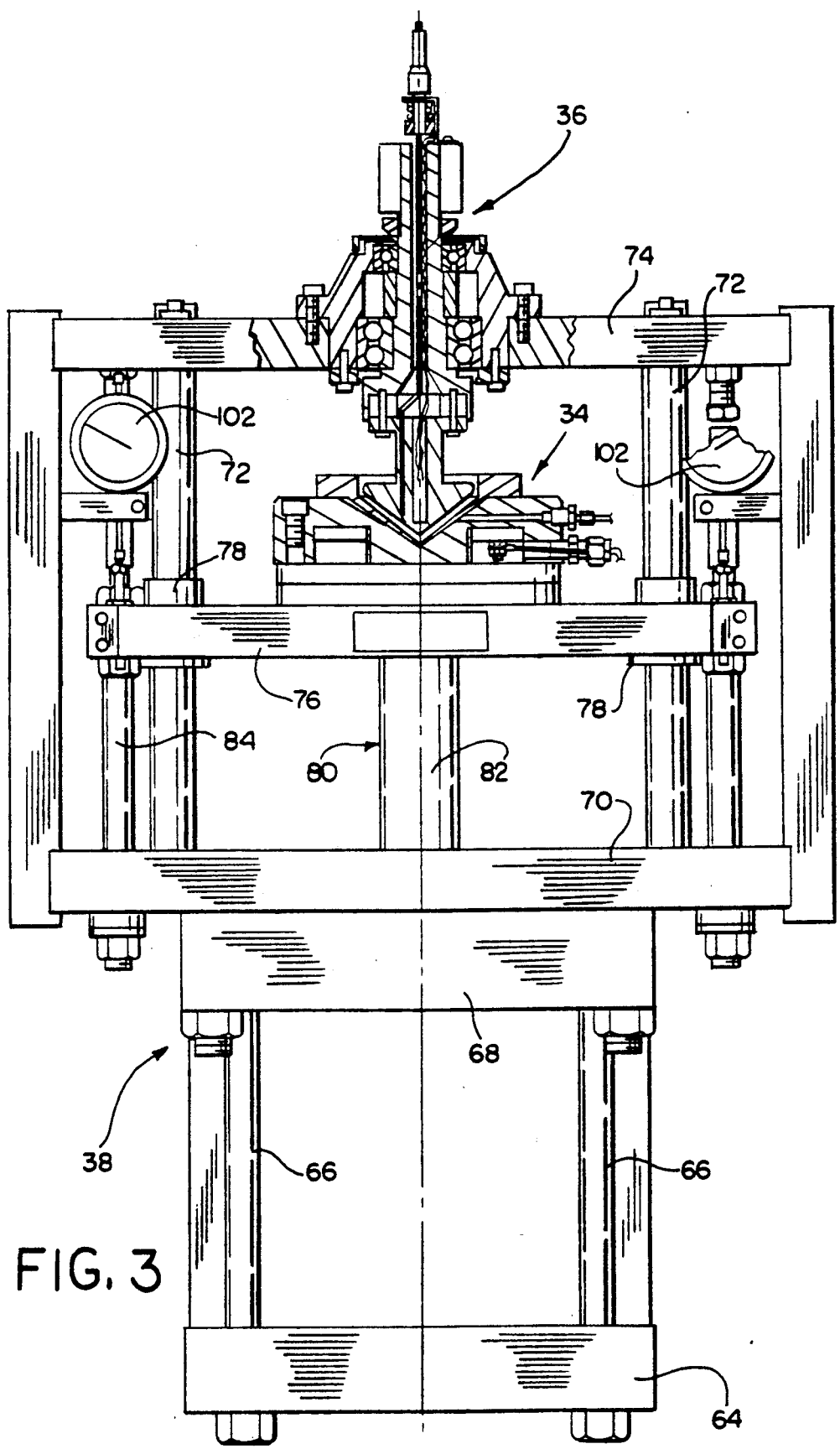
FIG. 3 is a front view of the internal components of the DSR device with the cabinet removed.

Referring now to the several figures in which like reference numeral depict like items, and initially to FIGS. 1-3 there is shown a Dynamic Stress Relaxometer (DSR) System 10. The DSR system 10 includes a dynamic stress relaxometer device 12, a dedicated processor 14, a general purpose computer 16, a printer 17 and a plotter 18 which function together to provide both quantitative and qualitative information about viscoelastic material subject to the test.

Briefly, the DSR device 12 performs a test of a viscoelastic material (test specimen) by subjecting the test specimen to a prescribed impulsive angular deflection, generally ½, or 2 degrees. (Other deflections may be employed, for example, depending on the properties of the material, the capability or design of the DSR machine, etc.) This creates a torsional stress in the test specimen resisting the angular deflection. The DSR device 12 then measures the relaxation of the torsional stresses in the test material over time and provides the data, in the form of an analog signal, to the dedicated processor 14. The dedicated processor 14 scales and filters the signal and digitizes it for digital processing in the dedicated processor and, in some cases, in the general processor 16 also.

The DSR system 10 preferably provides a selection of three testing procedures, called PROGRAM I, PROGRAM II, and PROGRAM III, for manipulating the data, for controlling the test, and optionally for controlling ancillary or external operations, such as in a feedback or feedforward control system. In a feedback control system the DSR system may be provided with a sample of a prepared viscoelastic material of which it will determine the fundamental viscoelastic properties or other measured characteristics, as will be discussed later. The values of some or all of these properties or measured characteristics are then provided to a suitable controller which may adjust the quantities of resins and fillers or other additives supplied to a continuous mixing apparatus preparing the viscoelastic material which was sampled. In another example of a DSR system in a control system, control can be had over the processing of a previously prepared viscoelastic material. In this instance the DSR system determines the fundamental viscoelastic properties or other measured characteristics of a sample from a batch of material, such as in forming a tire. The values of some or all of these properties or measured characteristics are then provided to a controller which may, for example, adjust the time or temperature of the next process. While this is an example of a feedforward control system, the DSR system could similarly be used in a feedback control system used in controlling the processing of a material based on the analysis of a sample of processed material.

Figure 4:
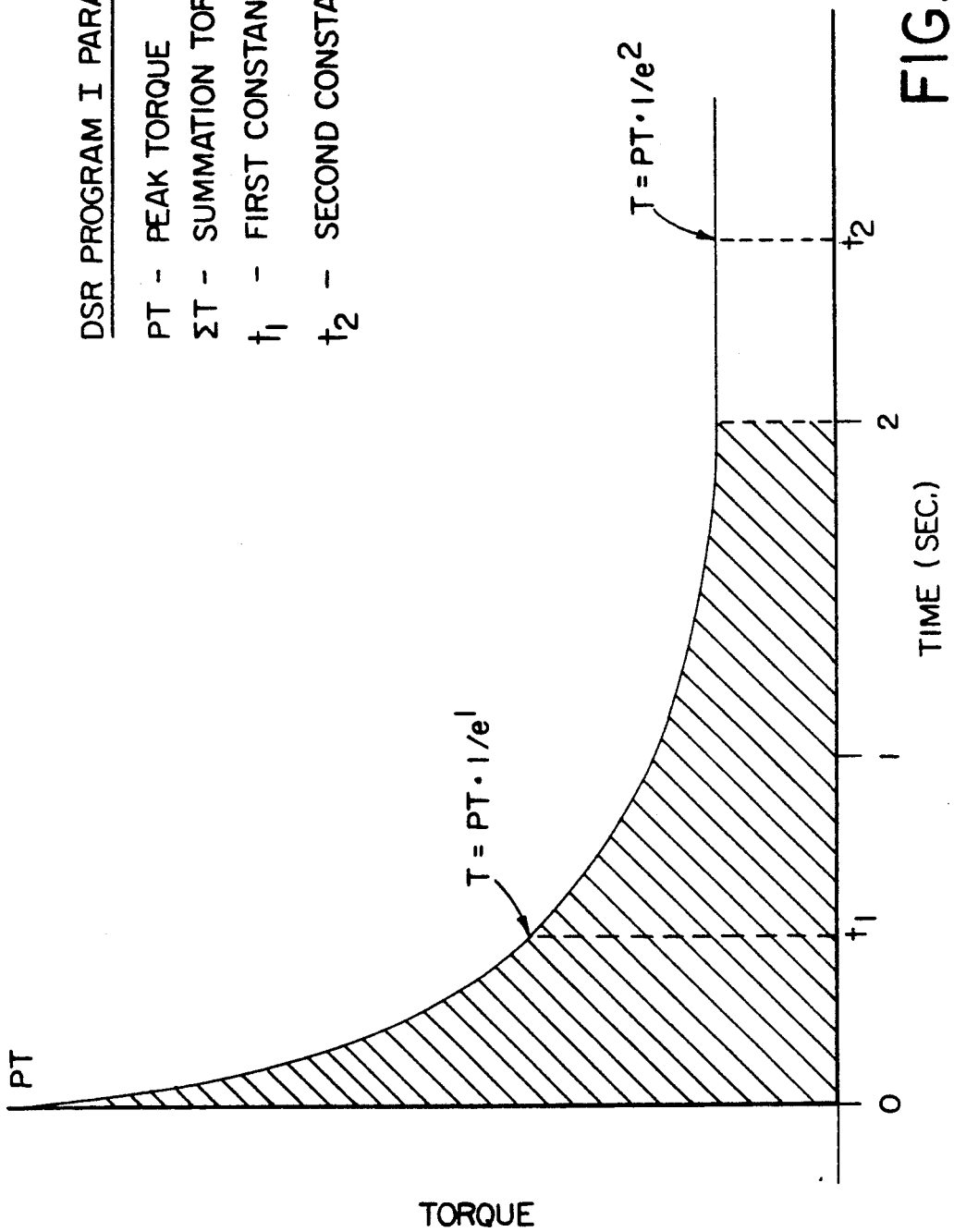
FIG. 4 is a graph of the Torque v. Time curve generated by PROGRAM I (there are several operational programs or computer programs employed in the DSR, as are described below)

The PROGRAM I test procedure, performed in the dedicated processor 14, provides a torque vs. time response curve (see FIG. 4), measures the maximum torque and the time for the stresses in the test specimen to relax beyond certain set amounts (time constants), and computes a summation of the relaxation torque over a certain time period, such as a two second period. The PROGRAM I test results provide a convenient and efficient way of grading materials, such as for quality control purposes, and for predicting the suitability or processability of a material for a certain use. When the PROGRAM I test is used as a quality control mechanism, the numerical results of several tests performed over a work shift or other period of time may be transferred to the general computer 16 for statistical analysis, such as to provide a mean or standard deviation of the results.

Figure 5:
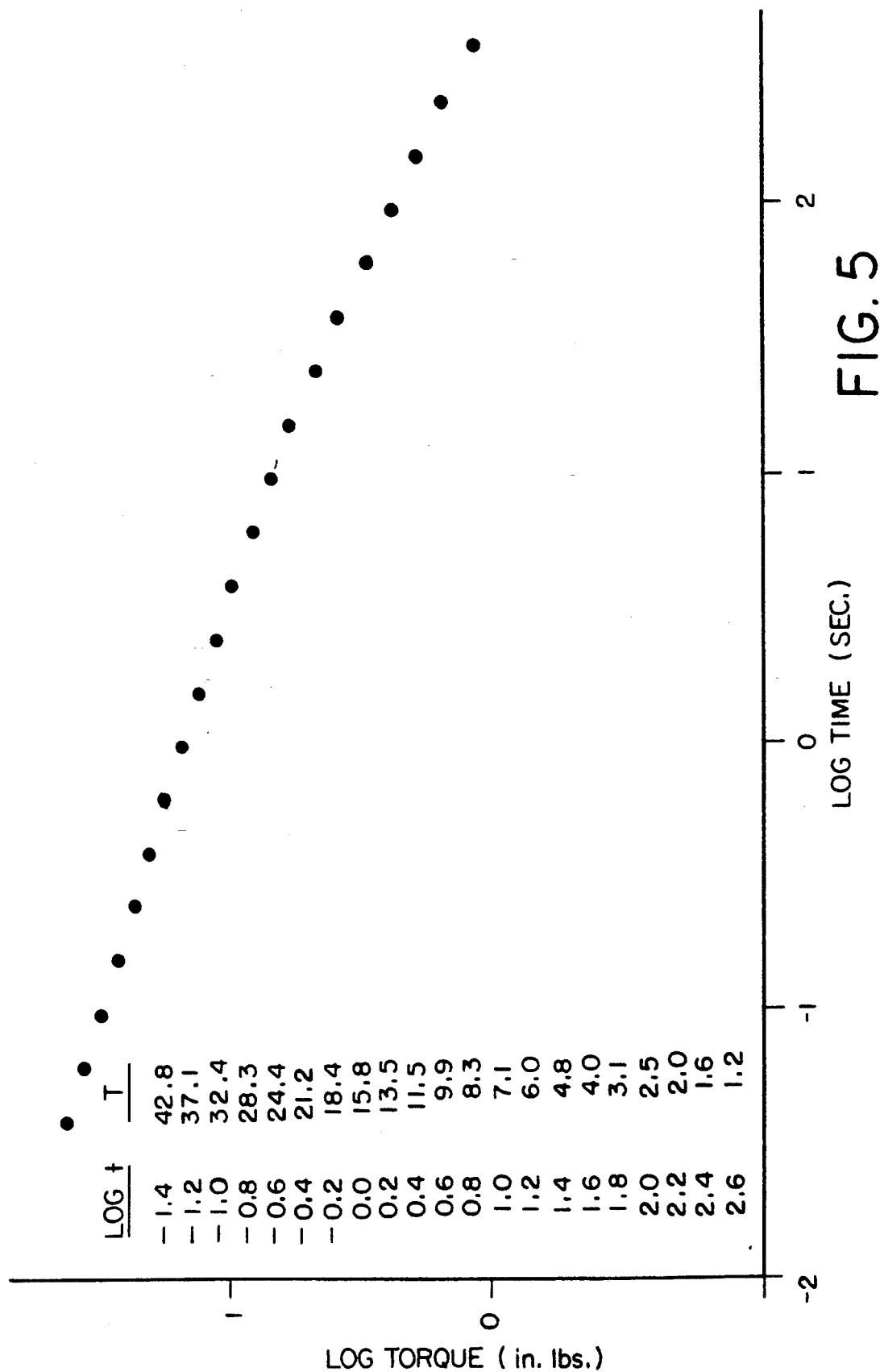
FIG. 5 is a graph of the Log-Torque v. Log-Time plot generated by PROGRAM II.

The PROGRAM II test procedure, also performed in the dedicated processor 14, produces a log-torque vs. log time curve of the relaxing stresses in the test specimen (See FIG. 5). The PROGRAM II log plot provides a justification or explanation of the PROGRAM I test results, and also facilitates the determination of certain characteristics of the test specimen, for example, whether the test specimen is a branched or linear polymer. The PROGRAM II plot could, of course, be other than log based; the log-based plot, however, provides readily usable information in a convenient format and is thus employed.

Unlike the PROGRAM I or PROGRAM II tests, the PROGRAM III test is preferably performed partly in the dedicated processor 14 and partly in the general processor 16. The dedicated processor 14 produces a preselected number of coupled torque and time data pairs which are transferred to the general processor 16 for further processing. The general processor 16 determines from those pairs a number of fundamental viscoelastic properties of the test specimen as a function of frequency, such as the storage modulus, the loss modulus, the complex viscosity and another property called tan-delta. These values are presentable in numerical and/or graphical format and may be presented in some cases as a function of one another, or with multiple tests and/or properties on one graph. (See FIGS. 6-9).

The numerical and/or graphical output of the PROGRAM I, PROGRAM II or PROGRAM III tests may be displayed on a video monitor 20 or in a hard copy format on the printer 17 or plotter 18. When displayed on the video monitor 20 the general processor 16 allows much of the graphical output to be massaged, such as through changing the degree of fit of the curve following the actual coordinate data points. The outputs of PROGRAMS I, II and III may be used to control various apparatus, such as that used to make the material being tested, that employing the material being tested, etc.

Turning to a more in depth discussion of the DSR system 10 and its components, and referring again to FIGS. 1-3, the general processor 16 is preferably an IBM TM compatible microcomputer, such as that manufactured by COMPAC TM, although other generalized computers, processors or the equivalent may be substituted with the appropriate modifications to the communication protocol. The general processor 16 is provided with a video display device 20 or the like and a keyboard 22 for interaction with an operator.

The dedicated processor 14 includes analog components for conditioning an analog input signal from the DSR device 12 and digital components for analyzing and recording the digitized signal and providing digital output to the general processor 16. The center of the digital components is preferably an INTEL TM 8085 microprocessor although other microprocessors may be employed, as would be apparent to one of ordinary skill in the art. A more complete description of the dedicated processor 14 is provided below.

The DSR device 12 includes a number of panels 30 forming a cabinet 32 which partly encloses the stator assembly 34, the rotor assembly 36, the control electronics 37 (shown in FIG. 15), and a supporting structure 38 for maintaining all the elements in their respective places.

Fundamentally, when the DSR device 12 is used to test a material, a quantity of such material is placed in the stator, the material is heated, the stator and rotor are brought together to apply compressive force to the material to obtain a sample having a constant thickness, and the above-mentioned deflection is applied. Data is taken, especially as the material relaxes after being deflected (subjected to torsional stress), and the data is processed and used in various ways, for example, as are described herein. Further details of the operation of the DSR are presented below.

On the front face of the DSR immediately below the stator assembly is an upper control panel 40. The upper control panel 40 has a tripole switch 42 for placing the DSR in MANUAL, AUTOMATIC or OFF mode, a power switch 43, and a pair of tripole switches 44a and 44b; one located at the extreme left side and the other at the right side of the panel. The switches 44a and 44b open or close the stator and rotor assemblies 34, 36 as described below. The switches 44a and 44b are biased in a null position. To close the assemblies 34 and 36, which is actually accomplished by elevating the stator assembly 34 to a position slightly below the rotor assembly 36, both switches 44a and 44b must be held in the CLOSE position simultaneously. This is a safety feature which prevents an operator from accidently closing the assemblies and thus helps to prevent operator injury. A pair of indicator lamps 46 and 48 visually indicate whether the rotor and stator assemblies are in the CLOSE or OPEN position, respectively. Gauges 50, 52 and 54 located near the top of the DSR device 14 provide a visual readout of the closure, stroke and retract pressures, respectively.

An lower control panel 56 directly below the upper control panel 40 includes the rotor and stator temperature controllers 58, 60, which allow the temperatures of the rotor and stator to be set, and a presetable stroke timer 62, which controls the time period between closure of DSR and the deflection of the viscoelastic material to be tested.

The supporting structure 38, as shown in FIG. 3, includes a base 64 from which extends vertically four support columns 66. Affixed atop the vertical support columns 66 is a secondary base 68. The base 64, vertical support columns 66, and the secondary base 68 provide a stable structure upon which the support table 70 is secured.

Four cylindrical rods 72 arranged in a rectangular configuration and extending vertically from the support table 70 maintain the rotor table 74 and stator table 76 in correct relative positioning. The rotor table 74 from which the rotor assembly 36 is mounted is non-movably secured at or near the top the rods 72. Stator table 74 upon which the stator assembly 34 is mounted is slideably secured on the rods 72 by bushings 78 that allow the stator table 76 to slide vertically along a portion of the length of the rods 72. Vertical movement is achieved by a hydraulic cylinder assembly 80 positioned between the secondary base 68 and the stator table 76. The blind end of the cylinder assembly 80 is suitably secured to the secondary base 68 and the cylinder rod 82 extending from the cylinder is secured to the bottom of the stator table 76. Actuation of the hydraulic cylinder assembly 80 is accomplished through the control of pressure through inlet and outlet ports (not shown).

Figure 10:
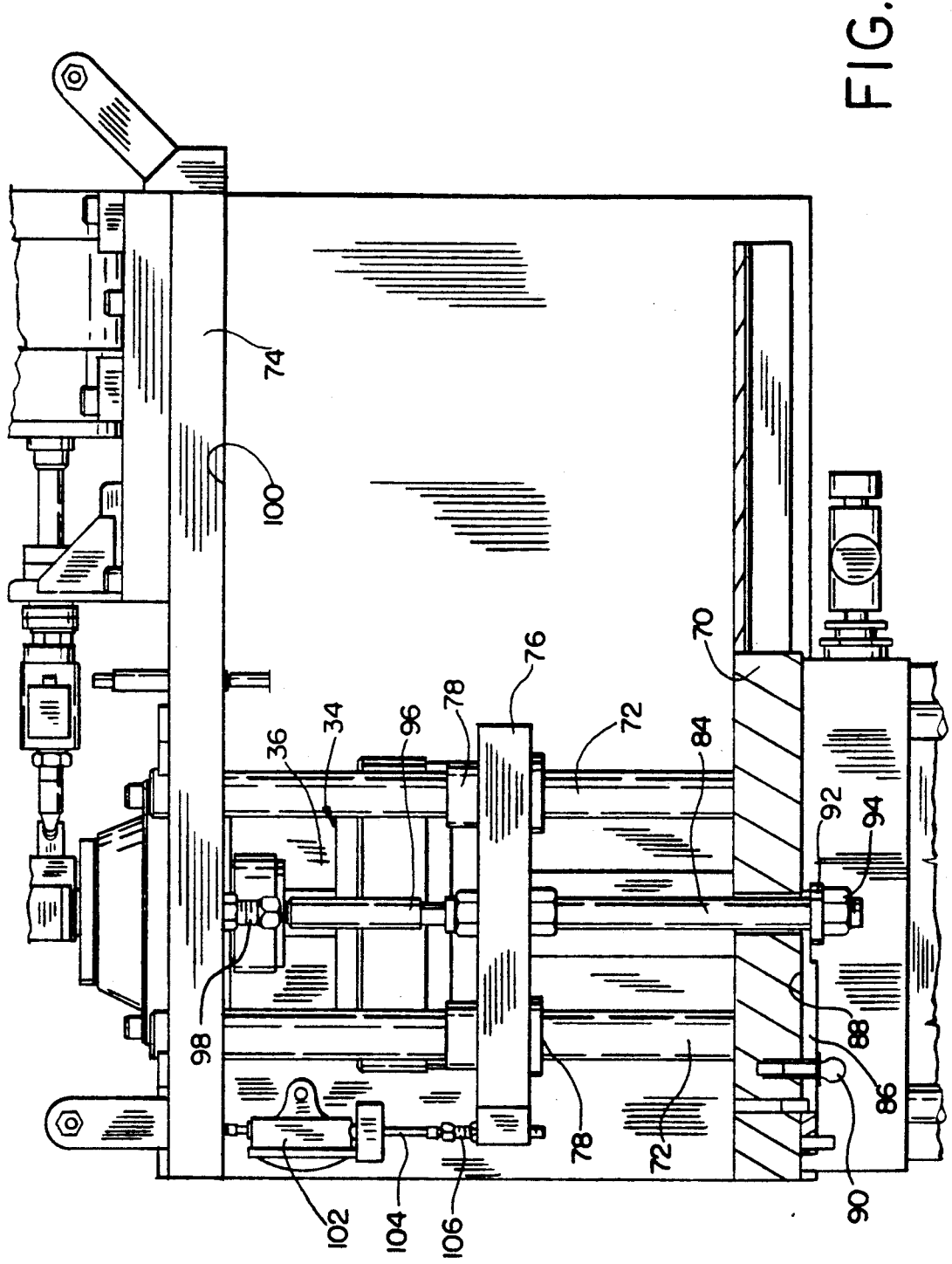
FIG. 10 is a partial side view of the DSR device.

The maximum length upward of travel of the stator table 76 along the cylindrical rods 72 is determined by two rods 84 extending vertically downward from the stator table 76 through clearance holes in the support table 70, as shown in FIG. 10. Shims 86 mounted to the bottom face 88 of the support table 70, such as by machine screws 90, provide for precise control of the closure height of the stator assembly 34. Stops 92 secured to the end of the rods 84 by a nut 94 contact the shims 86 when the stator table 76 has reached its maximum height to prevent further elevation. The maximum elevation is further determined by abutment rods 96 which extend from the stator table 76 along the vertical axis of the rods 84. The abutment rods 96 contact the vertically adjustable screws 98 which extend downwardly from the bottom face 100 of the rotor table 74.

A pair of closure gauges 102 are provided for visual measurement of the closure height of the stator table 76 and attached stator assembly 34. The closure gauges 102 include downwardly extending gauge pins 104 which contact vertically adjustable elements 106, such as machine screws, mounted to stator table 76.

Figure 11:
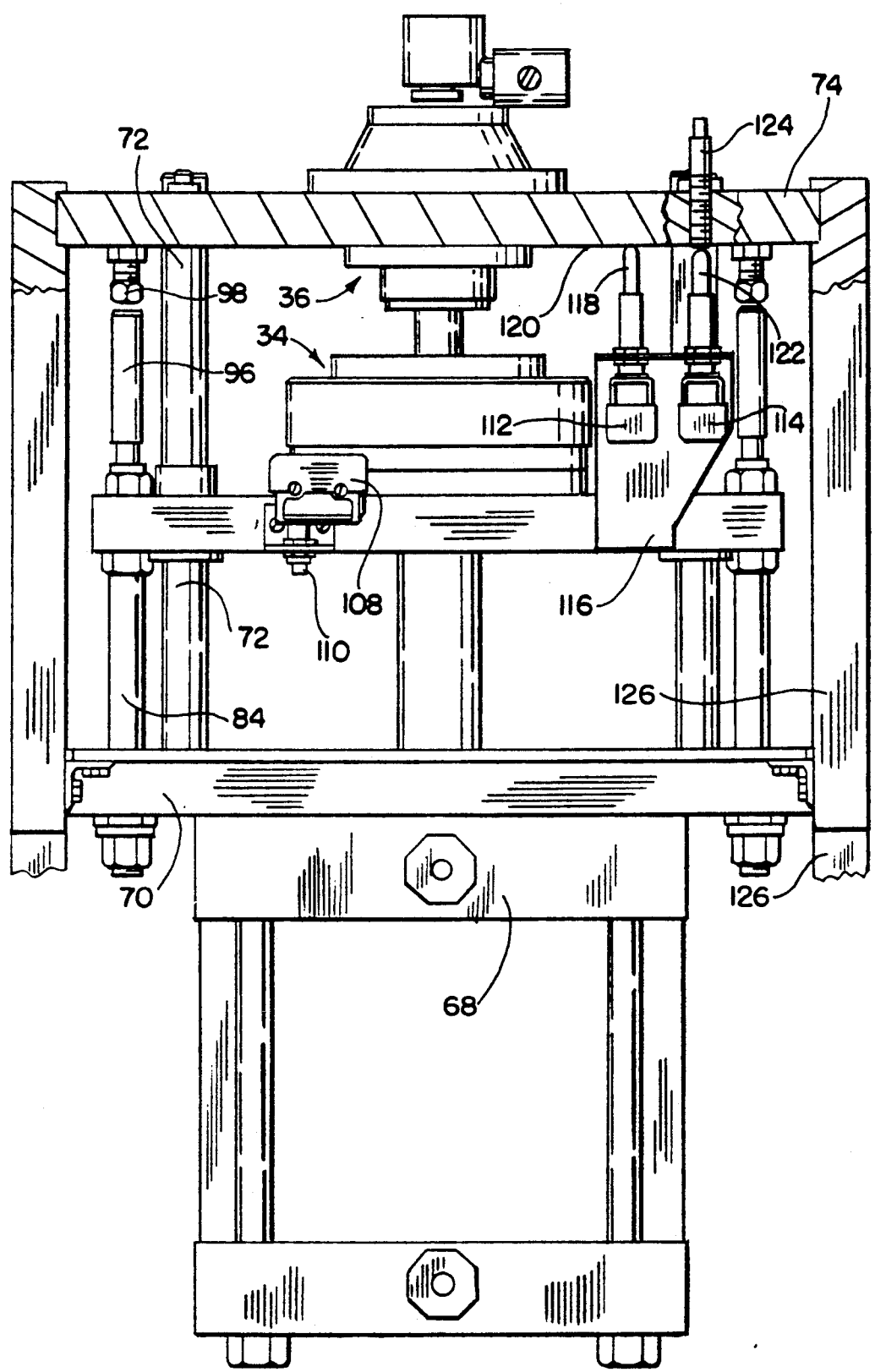
FIG. 11 is a rear view of the DSR device.
Figure 15:
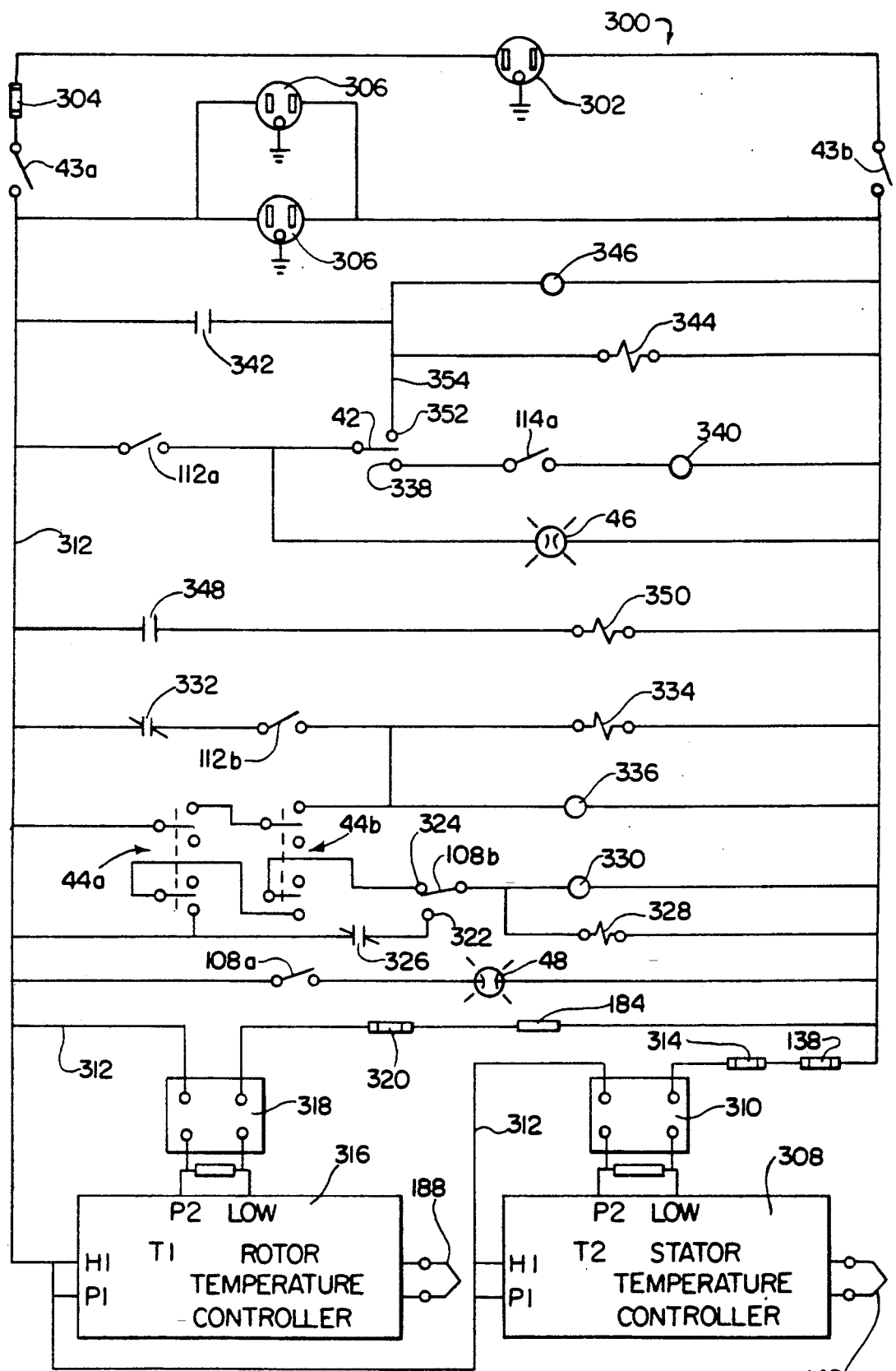
FIG. 15 is an electric schematic diagram of the DSR device control electronics.

Precise information as to the vertical location of the stator assembly 36 is determined by limit switches, shown in FIG. 11, and is provided to the DSR control electronics 37 (FIG. 15). Lower limit switch 108, secured to the stator table, contacts the support table by pin 110 when the stator table 76 has reached its lowest position. Upper limit switch 112 and fine upper limit switch 114 are mounted to a common support 116 which is secured to the stator table 76. Upper limit switch 112 includes a vertically extending pin 118 which contacts the bottom face 120 of the rotor table 74 when the stator assembly 34 has reached a location .050 inches below its final closure height. Fine upper limit switch 114 includes an upwardly extending pin 122 which contacts a vertically adjustable contact 124 when the stator table has reached a location 0.005 inches from its final closure height. Electrical signal outputs from the limit switches 108, 112 and 114 are provided to the DSR device 12 control electronics 37 which are discussed below.

Outer support elements 126 secured to the rotor table 74, the support table 70, and the base 64 provide an outer structure upon which the housing panels 30 are secured.

Figure 12:
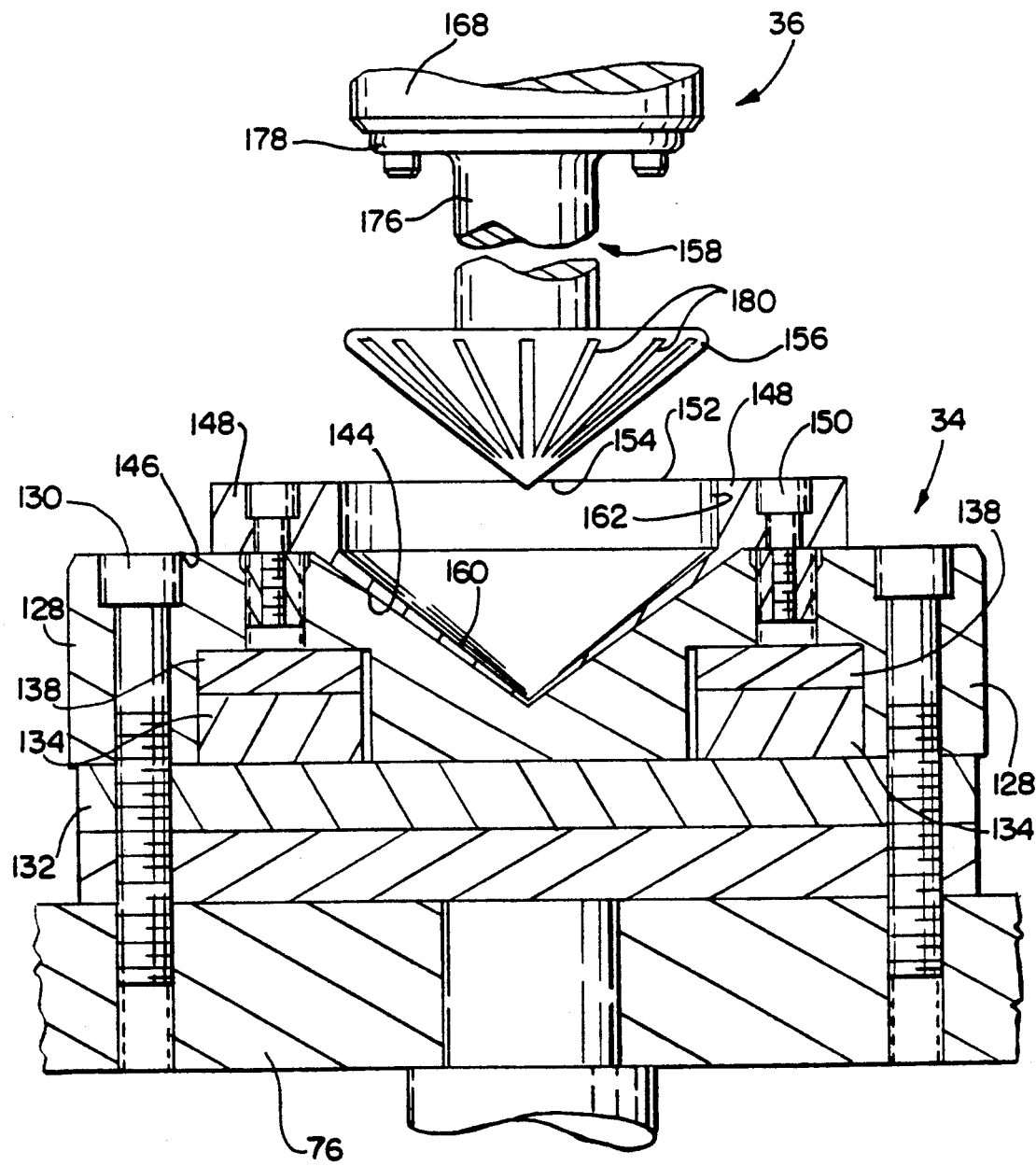
FIG. 12 is a cross-sectional view of the stator assembly with the rotor shown at partial closure.
Figure 13:
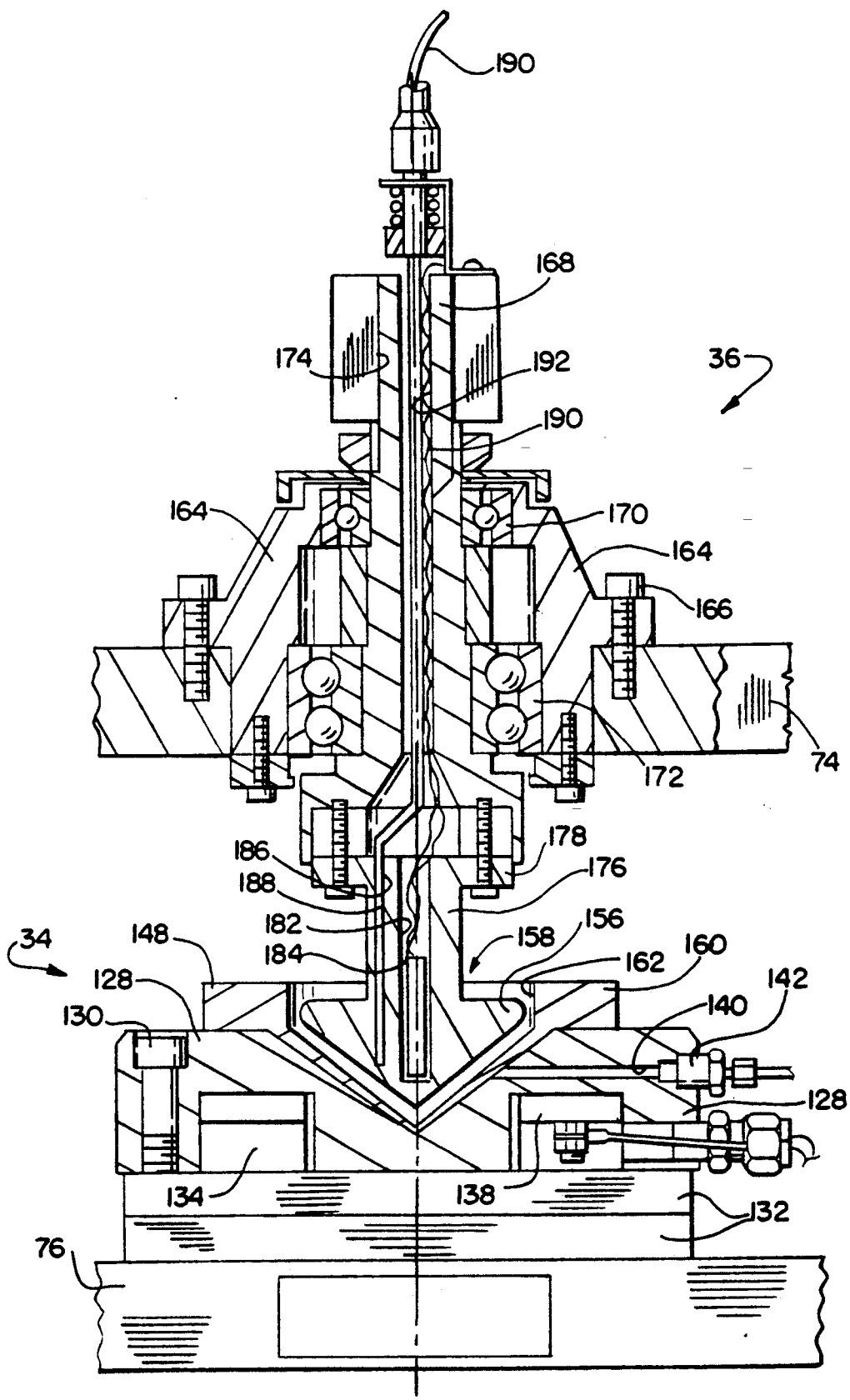
FIG. 13 is an illustration of the area including the stator and rotor assemblies with the assemblies shown in cross-section.

Referring now to FIGS. 12 and 13, there is shown a cross-sectional view of the stator and rotor assemblies 34 and 36. The stator assembly 34 includes a stator base 128 which is bolted to the stator table 76 with bolts 130. An insulating member 132 interposed between the stator base 128 and the stator table 76 prevents heat transfer from the stator base 128 to the stator table 76. The stator base 128 includes an annular recess 134 located in its bottom face 136 for the insertion of a 500 watt ring-type electrical heating element 138, and a lateral recess 140 for the insertion of a temperature sensing device 142, such as a thermocouple. The stator base 128 further includes a conical recess 144 in its top face 146 into which a specimen container 148 is removably secured, such as with bolts 150.

The specimen container 148 includes a truncated cone shape cavity 152 in its top face 154 for the reception of the generally conical shape lower portion 156 of the rotor 158 of the rotor assembly 36. The conical shape lower region 160 of the cavity 152 is truncated at the upwardly extending cylindrical face 162. The conical shape lower region 160 may be provided with radially extending channels or grooves or some other suitable surface (not shown) which prevents rotation of the specimen contained therein relative to the specimen container 148.

The cone shape lower portion 156 of the rotor 158 and the cone shape lower region 160 of the cavity 152 are of an equal conical angle. Consequently, when the stator assembly is raised to the closed position, the volume of specimen material sandwiched between the rotor and the specimen cavity will be of a constant thickness throughout. This facilitates the calculation of accurate test results without requiring that the specimen be subject to a constant stress throughout the specimen.

The stator base 128, the specimen container 148 and the rotor 158 are constructed of a material having a high coefficient of thermal conductivity and a high degree of resistivity to chemical interaction with the specimen material, such as a chromium steel. The high thermal conductivity of the stator base 128 and the specimen container 14 in conjunction with the low thermal conductivity associated with the insulating member 132 provide a heat transfer path whereby heat generated by the heating element 138 is efficiently transferred to the test specimen located in the specimen container 148 without substantial loss to the stator table 76.

The rotor assembly 36 aligned directly above the stator assembly 34, as shown in FIG. 13, includes an annular housing 164 extending through and secured to the rotor table 74 by the bolts 166. A rotor shaft 168 is disposed within the annular housing 164 and maintained in correct relative positioning by annular bearings 170 and 172. The bearings 170, 172 allow for angular rotation of the rotor shaft 168 within the annular housing 164 while preventing axial movement. The outer surface 174 of the rotor shaft 168 is stepped with each subsequent lower step increasing in diameter. This stepped outer surface 174 of the rotor shaft 168 allows the upward forces on the rotor shaft to be distributed among the bearing elements 170, 172.

Secured to the bottom of the rotor shaft 168 is the rotor 158. The rotor includes a lower conical region 156 for insertion into the specimen container 148 and a cylindrical shaft portion 176 broadening into a flange 178 for mounting to the rotor shaft 168. The conical lower portion 156 of the rotor 158 may be provided with radially extending channels or grooves 180 to prevent the specimen from rotating relative to the surface 156 upon deflection. The rotor 158 further includes a vertical passage 182 for the insertion of a 200 watt electrical heating element 184 and an offset vertically extending passage 186 for the insertion of a temperature sensing device 188, such as a thermocouple. The electrical leads 190 of the heating element 184 and the thermocouple 188 extend upwardly through an axial passage 192 located in the rotor shaft 168 for connection to the DSR device 12 control electronics 37 described below.

Figure 14:
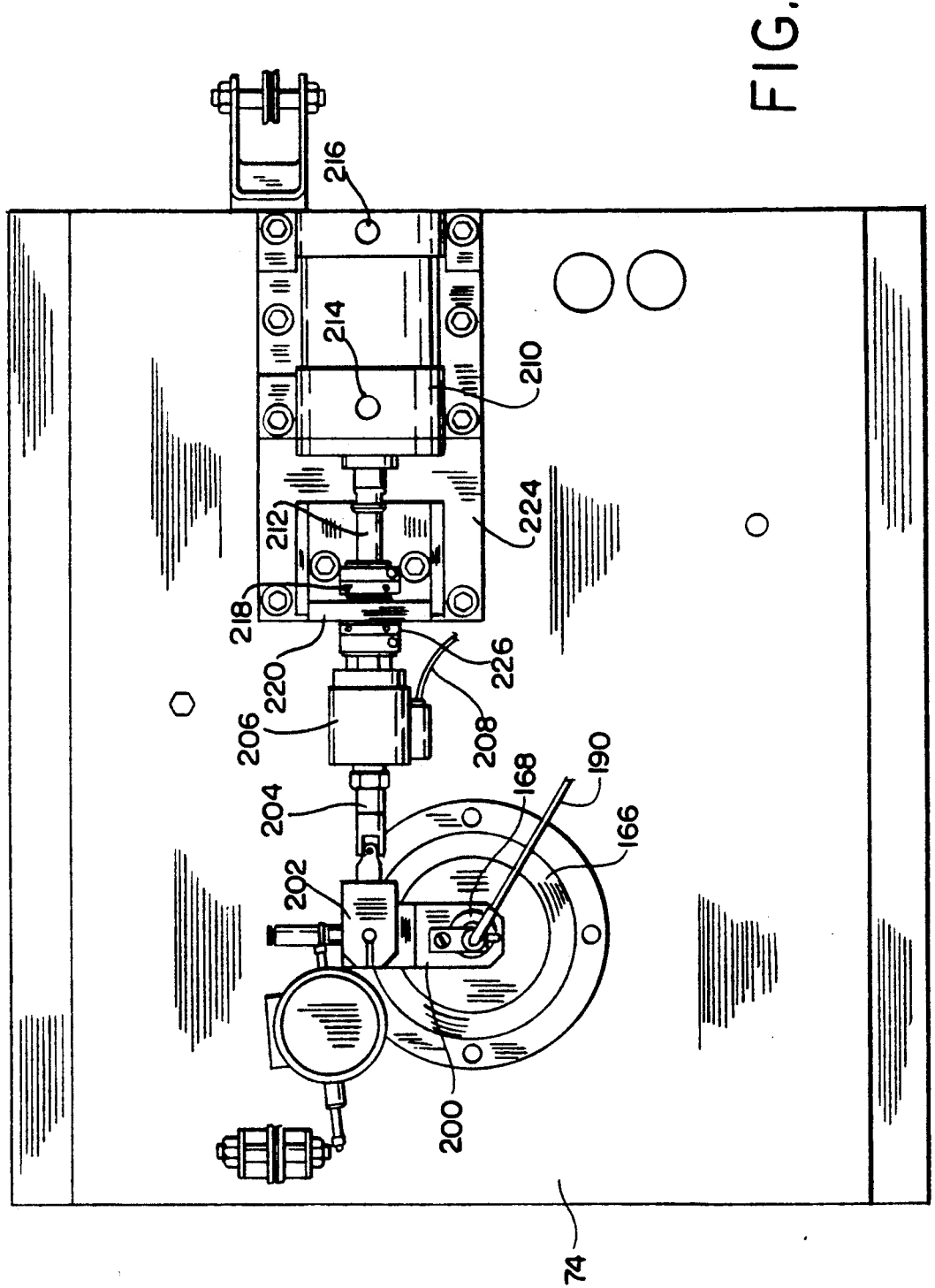
FIG. 14 is a top view of the rotor table showing the connections with the load cell and pneumatic cylinder.

At or near the top of the rotor shaft 168 is connected the rotor arm 200 as is shown in FIG. 14. The rotor arm 200 extends perpendicularly to one end of the longitudinal axis of the rotor shaft 168 and is connected to a universal joint 202. At the other end of the universal joint 202 is connected an extension arm 204 which is in turn connected to the load cell 206. The Universal joint 202 connection between the rotor arm 200 and the extension arm 204 allows the torque transferred from the rotor 158 through the rotor shaft 168 to the rotor arm 200 to be translated into a linear force through the extension arm 204 to the load cell 206 without imparting stresses involved with a bending moment on the load cell 206. Consequently, the load cell 206 accurately measures torque exerted on the conical face 156 of the rotor 158 by the test specimen.

The load cell 206 may be a conventional device which produces an output that is electrical in nature or is able to be read, sensed, detected or used in or with an electrical device. One example is a resistor, the resistance of which varies as a function of force applied thereto or deformation thereof. Other examples are a piezoelectric device, a variable capacitor, etc.

The load cell 206 preferably is coupled in a whetstone bridge configuration (not shown) and will be referred to below as including or being a whetstone bridge type load cell. Of course, other load cell devices and circuits may be used to detect or sense mechanical input and to convert such input to an electrical output or response of desired resolution. Thus, a similar element or elements capable of converting mechanical stress to electrical energy, which generates an electrical signal linearly proportional to the resisting torque on the rotor surface 156 may be employed. The electrical signal is conducted to the dedicated processor 14 over the wires 208.

The load cell 206 is also connected to the pneumatic cylinder 210 through the cylinder rod 212. The pneumatic cylinder 210 includes two ports 214 and 216 which are connected to pneumatic supply/exhaust lines (not shown). Applying pressure to port 216 while exhausting pressure from port 214 forces the cylinder rod 212 to extend from the pneumatic cylinder 210. This in turn causes the rotor 158 to rotate a predetermined angular distance in the counterclockwise direction. This angular distance is controlled by the axial distance between an annular stop 218 mounted to the cylinder rod 212 and an abutment element 220, secured to the cylinder base 224, when the cylinder rod 212 is in its fully retracted position. The angular position of the rotor 100 when the annular stop 218 is abutting the abutment element 220 is the null position of the rotor 158, corresponding to the position of the rotor at the start of the DSR test.

Conversely, applying pressure through the port 214 while exhausting the port 216 forces the cylinder rod 212 to retract into the pneumatic cylinder 210, thus causing the rotor 158 to rotate clockwise an angular distance corresponding to the axial distance between the abutment element 220 and the annular stop 226, mounted to the cylinder rod 212, when the cylinder rod 212 is in its fully extended position. Preferably this axial distance corresponds to a 2 degree rotation of the rotor 158. It takes approximately 5 milliseconds to effect the complete 2 degree rotation and thus the deflection of the specimen.

The degree of angular rotation of the rotor 158 may be decreased by mounting a shim (not shown) of appropriate width to the face of the abutment element 220 proximate the stop 226. Consequently, the travel of the cylinder rod 212 from its fully extended position towards its retracted position will be shortened by the width of the shim. It has been found that for some materials it is advantageous to effect a deflection of only 1 or ½ degree. To affect a 1 degree deflection, for example, the inserted shim would be of a width corresponding to one-half of the axial distance between the stop 226 and the abutment element 220, without the shim in place, when the cylinder rod 212 is in its fully retracted position; thus shortening the travel of the rod to one-half of its normal travel.

Referring now to FIG. 15 there is shown a diagram of an electrical circuit 300 for the DSR device 12 control electronics 37. Basically, the circuit 300 controls the upward or downward movement of the stator assembly 34, the impulsive rotation of the rotor 158, and the heating and temperature control of the stator base 128 and the rotor 158. The circuit 300 is connected to a 115 volt 20 amp alternating current power supply 302 through the power switch 43. A 15 amp fuse 304 provides overall overcurrent protection for the circuit 300. When the DSR device 12 is in an ON state, such as when switch 43 on the indicator panel 40 is in the ON position, switches 43a and 43b are closed. This provides power to the remainder of circuit 300 including the auxiliary power outlets 306.

While power is applied to the circuit 300, the stator temperature controller 308 continuously monitors the temperature of the stator assembly 34 as indicated by the output signal of the thermocouple 142. Based on the indicated temperature, the stator temperature controller 308 will cause the solid state switch 310 to assume an opened or closed position. When the solid state switch 310 is in its closed position, supply power from line 312 is conducted to the 500 watt ring type electrical heating element 138 in the stator base 128. A 10 amp fuse 314 provides overcurrent circuit protection. When the stator temperature controller 308 determines that the stator assembly 34 has reached its desired temperature, the solid state switch 314 is opened interrupting power to the 500 watt stator heater 138.

Likewise, the temperature of the rotor 158 is controlled by the rotor temperature controller 316 based on the output signal from the thermocouple 188 in the rotor. When the rotor 158 is below the selected temperature, the solid state switch 318 closes providing supply power from line 312 to the 200 watt rotor heater 184 to heat the rotor. A 10 amp fuse 320 provides overcurrent safety protection for this area of the circuit.

When the DSR device 12 stator and rotor assemblies 34 and 36, respectively, are in the fully open position, the lower limit switch 108 has pin 110 depressed against the support table 70 thus closing the switch 108A and permitting power from line 312 to flow to and light OPEN indicator lamp 48 located on the front face control panel 40. The switches 44A and 44B are biased in a null position and do not conduct power absent simultaneous actuation by an operator.

The lower limit switch 108 is also equipped with a switch 108b which engages contact 322 when the pin 110 is depressed against the support table 70 or contact 34 when stator table 128 is elevated so pin 110 is not depressed by support table 70. With the DSR device 12 in its fully open position, switch 108b is in position to engage contact 322 thus supplying power from line 312 through the closed up latch contact 326 to activate the down solenoid 328 and down latch 330 to maintain the stator assembly 34 in its fully lowered position. The activated down latch 330 opens the normally closed down latch contacts 332 preventing current flow to the up solenoid 334 absent action by an operator.

To start the test an operator simultaneously holds the switches 44a and 44b in their up, or CLOSE, position, thus power is supplied from the supply line 312 to the up solenoid 334 and the up latch element 336. Energizing the up latch element 336 opens the normally closed up latch contacts 326 thus preventing current flow to the down solenoid 328 and down latch 330, and closing the down latch contacts 332. This permits the upward movement of the stator table 76 while pin 110 of the lower limit switch 108 is still depressed and switch 108b is in position to engage contact 322. With the switches 44A and 44B held in their CLOSE positions, power is continually applied to the up solenoid 334 to raise the stator assembly 34 towards the rotor 158.

When the stator assembly 34 reaches a location approximately 0.050 inches from the final closure height, the upperly extending pin 118 of the upper limit switch 112 will be depressed against the bottom face 120 of the rotor table 74 closing the switch 112a and allowing power to flow from line 312 to light the CLOSED indicator lamp 46 located on the control panel 40. Simultaneously, the switch 112b of the upper limit switch 112 will also close and power will flow from line 312 through the closed down latch contacts 332 through the upper limit switch 112b to the up solenoid 334, bypassing operator switches, 44a. After once the stator assembly 34 has reached a height 0.005 inches from the final closure height, the pin 122 of the fine upper limit switch 114 will be depressed by the adjustable contact 124 thus closing the switch 114a. In the automated test case the switch 42 on the control panel 40 will be in the AUTOMATIC position (engaging contact 338) and power will be supplied from the supply line 312 through the upper limit switch 112a through the tripole switch 42 and contact 338, and through the fine upper limit switch 114a to the presetable preheat timer 340. The preheat timer 340 will begin to count down to zero from a preset value that is chosen to ensure that stator and rotor temperature controllers 308 and 316, respectively, have had sufficient time to bring the test specimen to the desired temperature. The up solenoid 334 will continue to elevate the stator assembly 34 until it reaches its final closure height.

When the preheat timer 340 times out, the timer contacts 342 are closed thus supplying power from the supply line 312 to the exhaust solenoid 344 and the exhaust timer 346. Activation of the exhaust solenoid 344 vents the pneumatic cylinder port 216 to ambient. The exhaust timer 346 invokes a 5 second pause, ensuring that the pressure in the pneumatic cylinder reaches ambient. At the end of the 5 second time-out, the exhaust timer contacts 348 are closed supplying power from the supply line 312 to the stroke solenoid 350 causing 70 psi of pressure to be applied to port 214 of the pneumatic cylinder 210. This causes the cylinder rod 212 to retract which, in turn, causes the rotor 158 to rotate the preset amount. At this point the test proceeds with the load cell 206 generating a signal proportional to the torque exerted on the rotor 158 by the test specimen and sending that signal to the dedicated processor 14 for processing as described below.

If the DSR device 12 is operating in manual mode, the operator actuates switch 42 on the upper control panel 40 to the MANUAL position once the stator assembly has reached the final closure height. This causes switch 42 to engage contact 352 thus supplying power to the exhaust timer 346 and exhaust solenoid 344 via line 354. The operation from this point on is as described above relative to the automatic mode. Note that the DSR device is preferably only operated in the manual mode to perform set-up operation on the device and not during an actual material test.

After the test is completed, the operator simultaneously holds both switches 40A and 40B in the OPEN, or LOWER, position to lower the stator assembly 34. When the switches 40A and 40B are held in the OPEN position, power is conducted from supply line 312 through the lower limit switch 108b, which is in position to engage contact 324, to the down solenoid 328 and down latch 330. The down latch 330 latches the down latch contacts 332 in an open position thus preventing current flow to the upper solenoid 334 and up latch 336 regardless of the position of the upper limit switch 112a and contacts 332. Simultaneously, the down solenoid 328 is energized and the stator assembly 34 continues to lower while the switches 44a and 44b are both held in the OPEN position.

One safety feature of the circuit 37 is that travel of the stator assembly is prevented absent direct action by the operator. When the stator assembly 34 is in its fully open, or fully lowered, position the up latch contacts 326 are in a closed position and the lower limit switch 108b is in a position to conduct current to the down latch 328 and down solenoid 330 thus preventing any movement of the stator assembly until both switches 44a and 44b are simultaneously held in the up or CLOSE position. At any time during elevation of the stator assembly 34 prior to reaching a location 0.050 inches from full closure height or at any point during lowering of the stator assembly, movement of the stator assembly is stopped if either of the switches 44a or 44b is not held in position.

Figure 16:
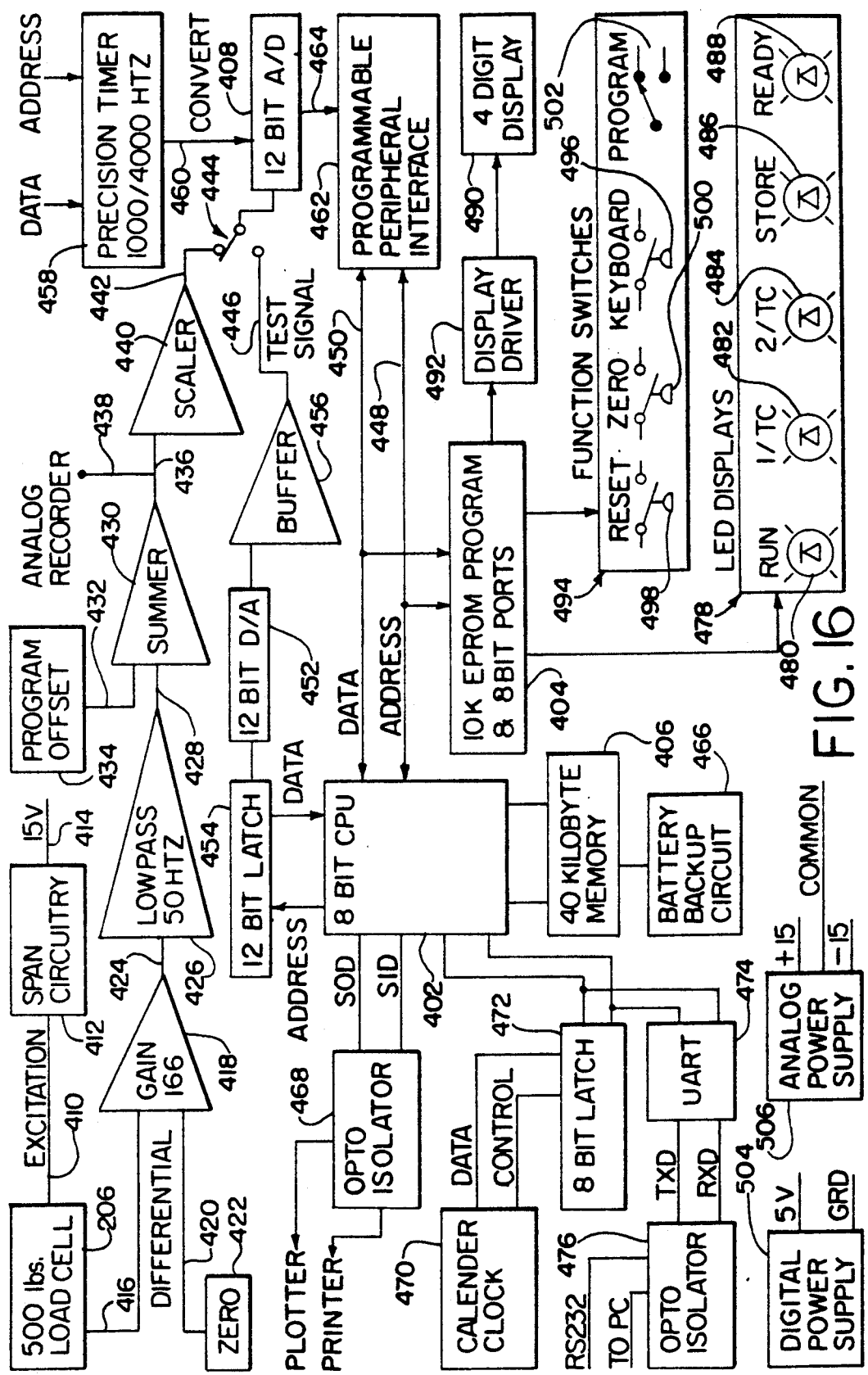
FIG. 16 is a data block diagram representation of the dedicated processor electronics.

Referring now to FIG. 16 there is schematically illustrated an electrical circuit data flow diagram for the dedicated processor 14. The dedicated processor 14 electronics include analog circuitry for processing an analog signal from the load cell 206 prior to digital conversion, and digital circuitry for analyzing the digital information to determine values indicative of various viscoelastic properties of the test specimen. The digital electronics include a computer processing unit 402, such as an Intel 8085 microprocessor, read-only program memory 404, random access storage memory 406, an analog to digital converter 408, plus a number of other components as will be described more fully below.

Discussing initially the analog components or analog component package of the circuit, the electrical components of the load cell 206, such as a whetstone bridge, are shown schematically in FIG. 16 at 206. The torque signal generated by the load cell 206 is a function of the excitation signal voltage 410, as well as the axial force on the cell. Accordingly, span circuitry 412 is provided to allow the supply power 414 to the load cell 206 to be adjusted, within a range of +/−5 percent of 5.25 volts, to accommodate inevitable sensitivity variances among different load cells.

Reference numeral 414 may be used here and elsewhere to designate an electrical line, group of lines, connection or output or to designate the signal thereon. Generally, if there is any significance to the difference between such designation, it will be clear from the context. Similar uses of reference numerals occur with respect to other lines and signals thereon, as will be evident.

Upon angular deflection of the test specimen, the load cell 206 generates an analog signal on line 416 which is provided to a differential amplifier 418 along with the zeroing signal on line 420 from the conventional manual zero 422 or offset device. The amplifier 418 sums the zero signal 420 with the load cell signal 416 to provide for calibration of the load cell 206. The resultant signal is amplified with a gain of 166 since the excitation output voltage of the load cell is relatively small.

The output signal 424 of the amplifier 418 is provided to a low pass filter 426 with a cutoff frequency of 50 hertz to filter out high frequency components of the output signal 424. The resultant signal 428 is summed in a summer 430 with an offset signal 432 from a program offset circuit 434 relating to whether the CPU 402 is executing PROGRAM I or PROGRAM II/PROGRAM III as will be described fully below. The output signal 436, having a correlation of 20 millivolts to one-inch pound of torque, may be tapped for use by a strip recorder or for use as a test signal 438.

A scaling unit 440 scales the output signal 436 of the summer 430 with a gain adjustable between zero and 1.5 to provide the analog signal 442. The gain of the scaling unit 440 is adjusted to absorb errors imposed on the analog torque signal through the cumulative tolerances of the various components of the analog component package and to provide scaling to the A/D converter 408 of one count equals 0.1 in-Lbs/torque. In this manner any selection of analog components can be adjusted to perform to consistent specifications, thus allowing the interchange or replacement of analog component packages without affecting the performance of the DSR. The scaled and filtered torque signal 442 is now suitable for digital conversion by the 12 bit analog to digital (A/D) converter 408.

The A/D converter 408 and scaled signal 442 are connected through a test switch 444 which allows the scaled signal 442 to be replaced by the test signal 446 under appropriate conditions. The test signal 446 is a known waveform which mimics an actual DSR test torque versus time curve. Since the waveform, and thus the data points along the waveform, are known, the test results are also known and can be used to determine whether the digital components of the dedicated processor 14 are functioning properly by whether they compute the expected known values.

The test signal 446 is an analog recreation of a series of data points stored in program memory 404. The CPU 402 accesses the locations in locations memory 404 containing the test digital data points via an address bus 448. The data points are returned to the CPU 402 over a data bus 450. The CPU 402 then transfers the test data to a 12 bit digital to analog (D/A) converter 452 via a 12 bit latch 454. The D/A converter 452 converts the latched 12 bit test data into an analog test signal 446. The test signal 446 is provided to the test switch 444 through the buffer 456, which increases the amplitude of the test signal commensurate to that of the scaled signal 442, for connection to the A/D converter 408 during test conditions.

The position of the test switch 444 is transparent to the operation of the A/D converter 408 which converts an analog input signal to a digital word regardless of whether that signal represents actual torque relaxation data from the load cell 206 or recreated test data. The A/D converter 408 having twelve information bits has a resolution of 4096 nondimensional counts. In the exemplary embodiment a 500 Lb$_f$ load cell 206 will, under operating conditions, experience a maximum of 200 pounds of force, and the desired resolution is 0.1 inch-Lb$_f$; therefore, it is convenient to allocate 4,000 of the 4,096 available counts in the A/D converter 408 for the conversion of positive torque. Consequently, 1 count equals 0.1 inch-Lbs$_f$. For a PROGRAM I test the measured torque is always positive, therefore, the remaining 96 counts go unused. When performing a PROGRAM II or PROGRAM III test, however, it is possible to have a measurement indicating a small negative torque. In these cases, the remaining 96 counts are used as an offset, equalling 9.6 inch-Lbs$_f$, to compensate for any small negative torque values.

The rate at which the A/D converter 408 converts the input analog signal to a 12 bit digital data word is either 1,000 or 4,000 conversions per second. (Other rates may be employed equivalently.) The rate at which the A/D converter operates is determined by the precision timer 458. The timer 458 produces a 1,000 or 4,000 hertz clock signal which is sent to the A/D converter to produce the desired conversion rate over the line 460.

Each 12 bit digital data word converted by the A/D converter 408 is passed to a programmable peripheral interface device 462 via the 12 bit data bus 464. The programmable peripheral interface 462 temporarily stores the digital data words in a data buffer section of the interface 462 prior to access by the CPU 402.

The CPU 402 accesses a data word from the programmable peripheral interface 462 by addressing the proper location in the data buffer via the address bus 448. The data word is returned to the CPU 402 over the data bus 450. Each data word obtained from the programmable interface 462 is examined by the CPU 402 and then placed in a location in the static random access storage memory 406. Forty kilobytes of accessible memory are provided for the accumulation of torque and elapsed time data for one or more DSR tests. The storage memory 406 is provided with a battery backup 466 to prevent the loss of stored data when power is interrupted to the memory. Alternatively, the storage memory could be implemented with chips using EE-PROM technology.

The CPU 402 may provide information to the plotter 18 or printer 17 via an opto-isolator 468. The CPU 402 is also provided with a calendar clock 470 through an 8 bit latch 472 to allow data to be tagged with the time the test occurred and to permit the CPU 402 to transfer test data at a predetermined time. The CPU 402 may transfer stored data from the storage memory 406 to the general computer 16 through a UART 474 and opto-isolator 476.

The CPU 402 interfaces with the 14 kilobyte program memory device 404 via the address bus 448 and data bus 450. The program memory 404 aside from storing the test data, also stores the executable computer program code for PROGRAM I, PROGRAM II, a portion of PROGRAM III, and other related computer program or operating codes necessary to control the dedicated processor 14. The program memory device 404 further includes a number of ports for the control of several LED displays 478 indicating such information as whether a test is running 480, whether the first time constant has been reached 482, whether the second time constant has been reached 484, if data is being stored 486, and a ready LED 488 which indicates when a PROGRAM II or PROGRAM III test is complete. Another port operates a 4 digit digital display 490 through a display driver 492 to provide a periodic visual display of torque information for use in calibrating the load cell 206 via the manual zero 422. Further ports interface with function switches 494 such as an additional keyboard 496, a reset switch 498, a zero switch 500, and a program switch 502 the functions of which are described below.

A digital power supply 504 provides 5 volt power to the digital components. An analog power supply 506 provides +/-15 volt power to the analog components of the dedicated processor 14.

Figure 17A:
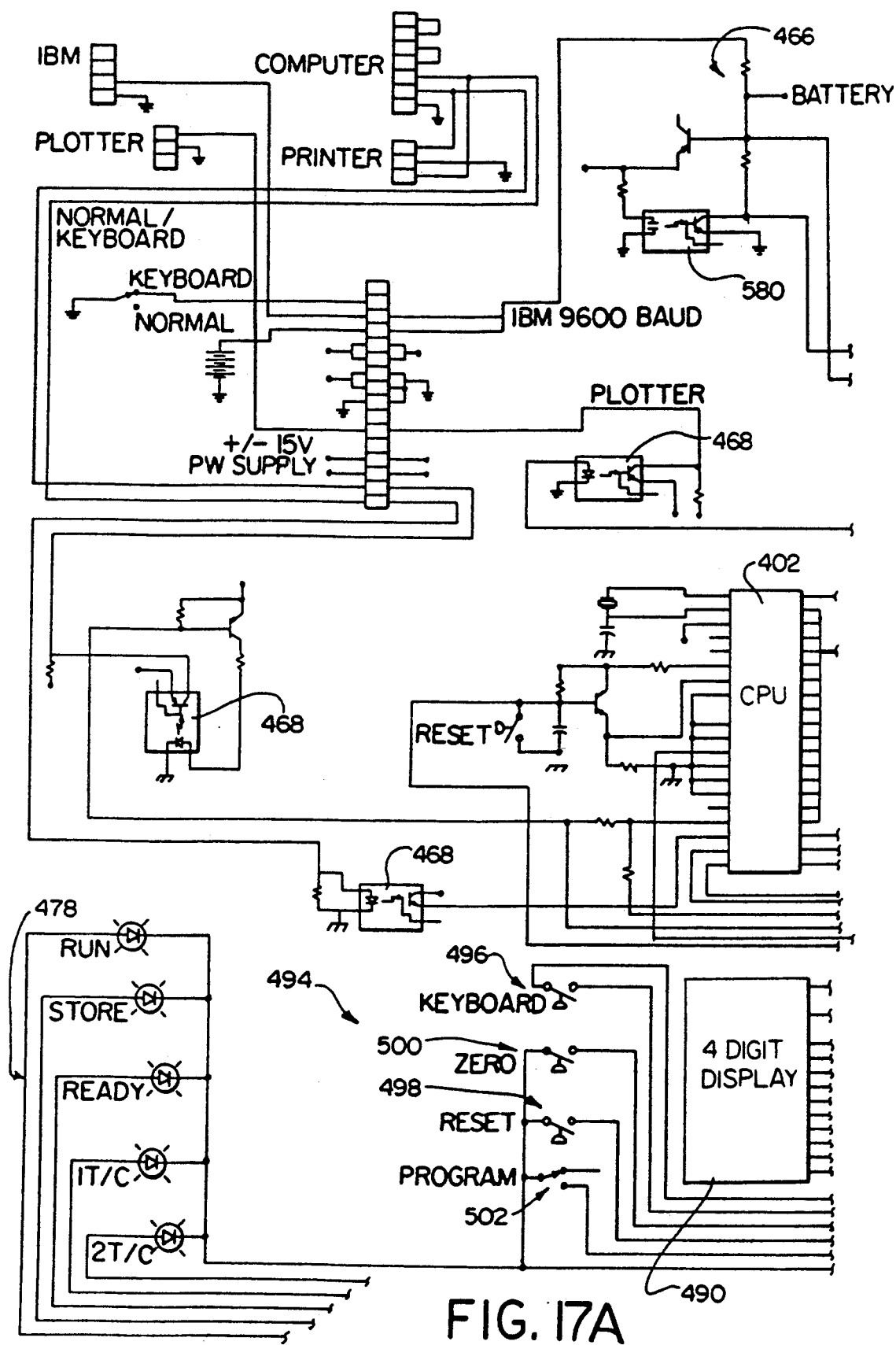
FIG. 17a–f are an electrical schematic diagram of the dedicated processor.
Figure 17B:
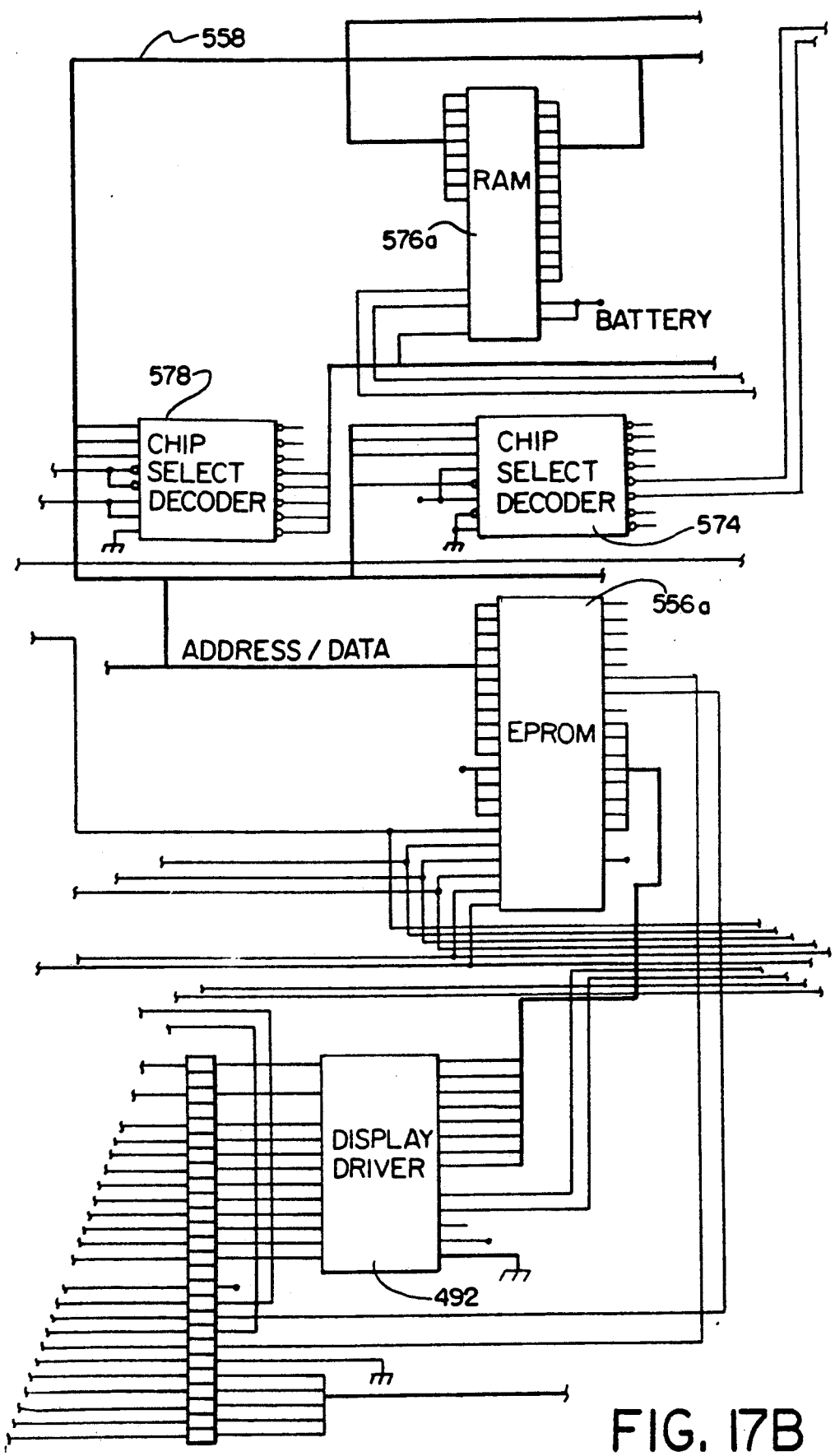
Figure 17C:
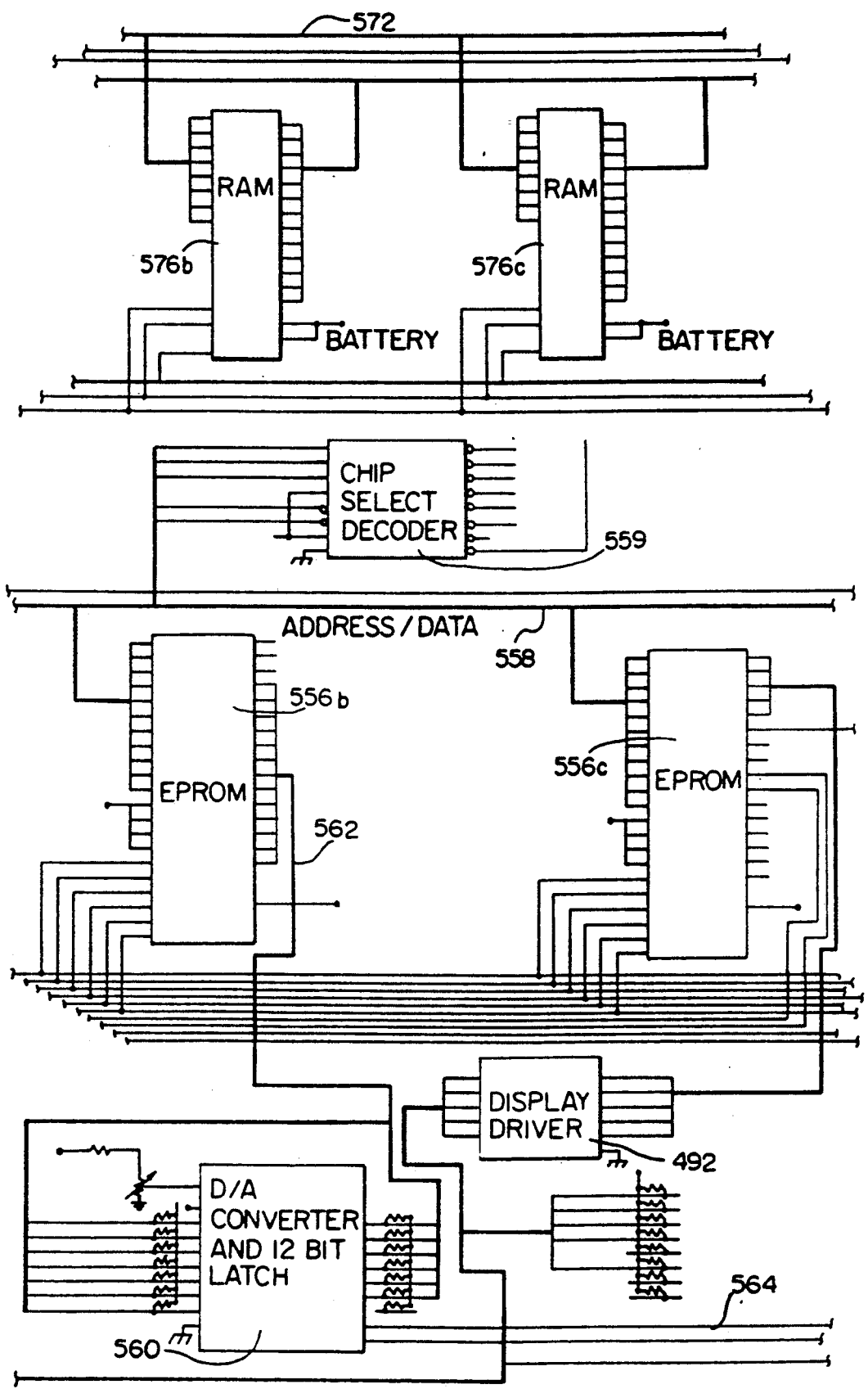
Figure 17D:
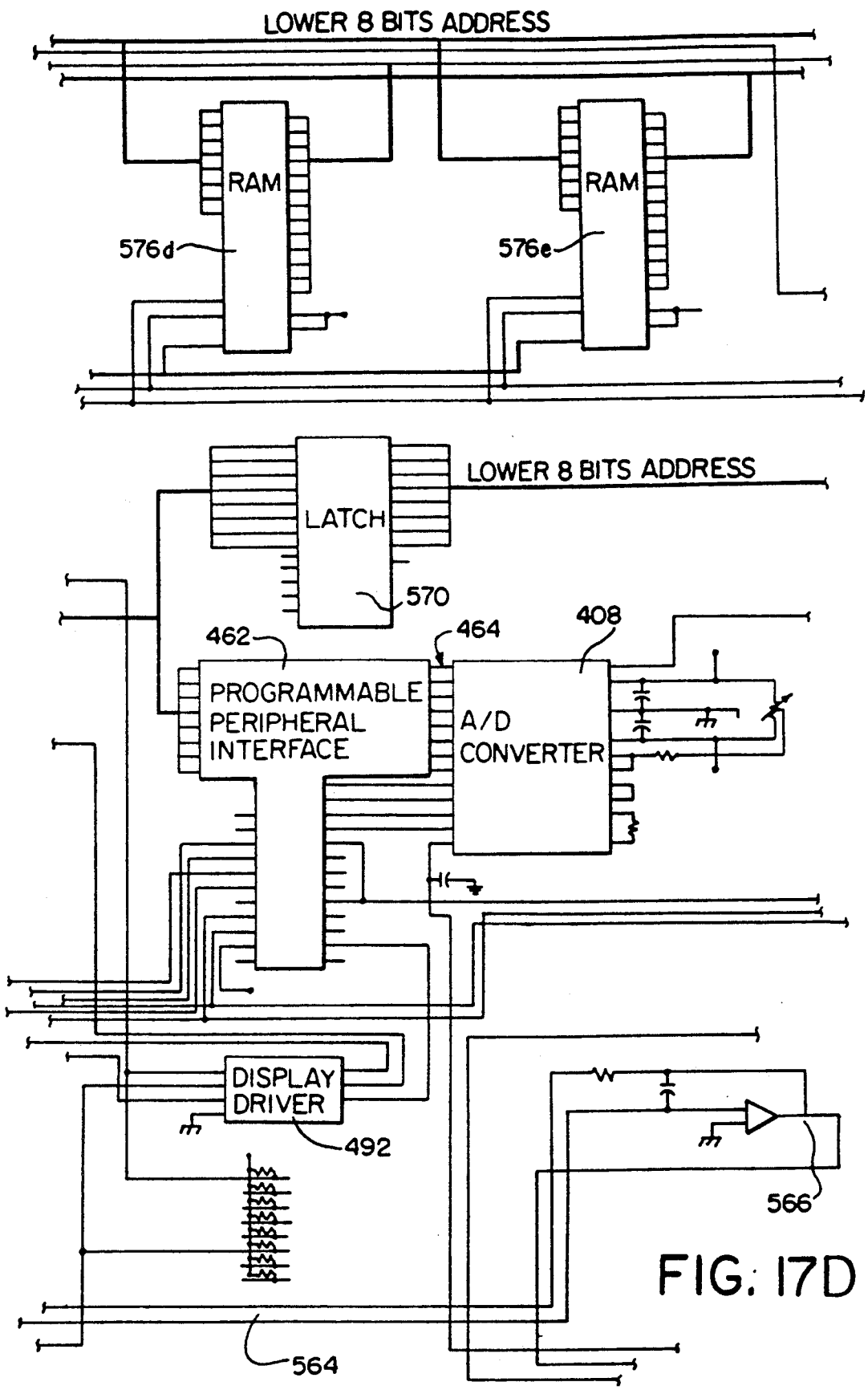
Figure 17E:
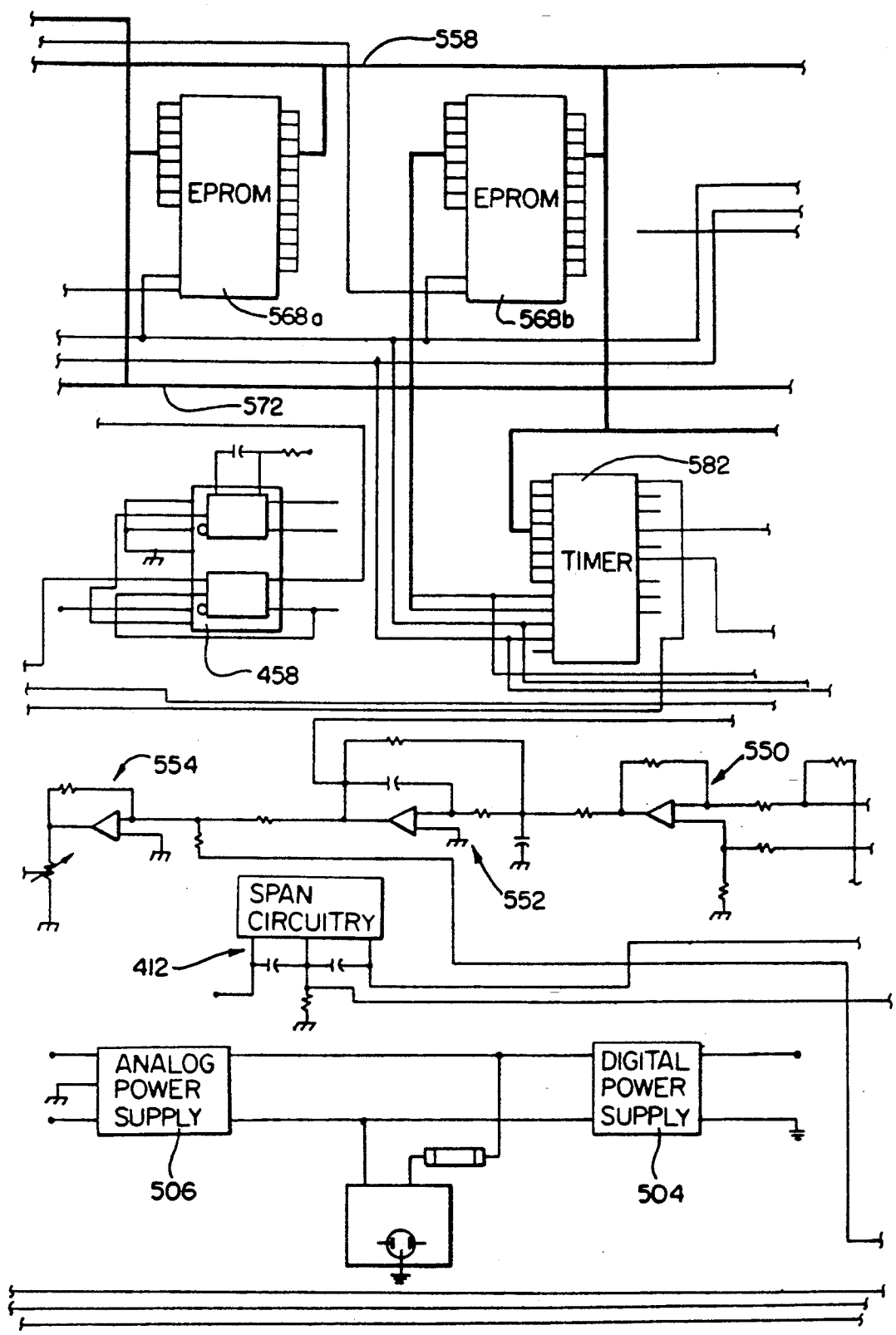
Figure 17F:
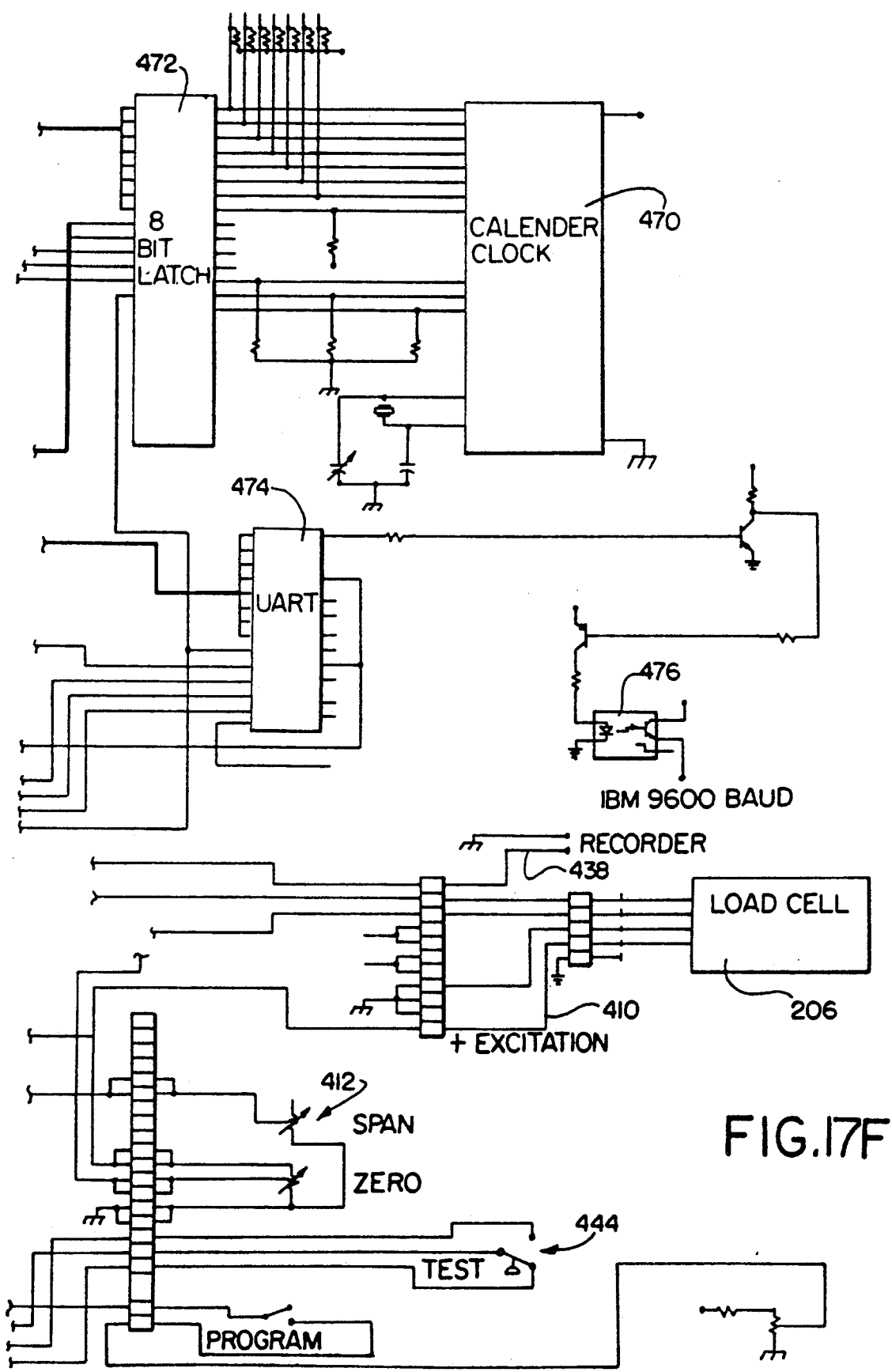

Referring now to FIGS. 17a-17f there is shown a schematic electric circuit diagram for the analog and digital electronics of the dedicated processor 14. The drawings may be placed side by side to depict continuation of various electrical lines or connections from sheet to sheet to complete the circuit. The load cell 206 (FIG. 17f) provides an analog signal to a series of operational amplifiers 550, 552, 554 (FIG. 17e) which perform the functions of the differential amplifier 418, the low pass filter 426, the summer 430 and the scaler 440 described above with respect to FIG. 16. The resulting signal is provided to the A/D converter 408 (FIG. 17d) through the test switch 444 (FIG. 17f). The A/D converter 408 provides 12 bit words to the programmable peripheral 462 which is implemented as a scratch pad RAM having two 8 bit ports and one 6 bit port. The information in these ports is accessible by the CPU 402 (FIG. 17a), which is preferably an Intel 8085 microprocessor, over the combined address/data bus 616. The CPU 402 operates at approximately 3 megahertz.

Preferably three Intel proprietary 2 kilobyte electronically programmable read-only memory (EPROM) integrated circuits or chips 556a, 556b and 556c form the program memory 404. Each chip has two 8 bit input-/output ports for interface with the function switches 494, and the LED displays 478 (FIG. 17a), the D/A converter 452 and 4 digit display 490. (The terms integrated circuit, chip, etc., may be used equivalently herein.) These EPROM chips 556a, 556b and 556c (FIGS. 17a and 17b) are accessible by the CPU 402 over the combined address/data bus 558. Each Intel EPROM chips 556a, 56b and 556c contains means for latching out the lower eight address bits from the combined address/data bus 558. However, if the functions of the EPROM chips are implemented with other commercial EPROMs, it may be necessary to include additional hardware to latch out the lower eight address bits, such as is described below relative to EPROM chips 568a and 568b (FIG. 17e). A chip select decoder 559 (FIG. 17c) enables the EPROM 56a, 556b or 556c allocated with the storage and port addresses to be accessed by the CPU 402.

One 8 bit port of the EPROM chip 556a provides digit information for the four digit LED display 490 (FIG. 17a) through the display driver 492 (FIG. 17b). The other 8 bit port of EPROM 556a monitors the program switch 502 and the zero switch 500 (FIG. 17a). One of the 8 bit ports of the EPROM chip 556c controls the LED display lamps 478 (FIG. 17a). A number of bits of the other port controls the display driver 492. A single chip 560 (FIG. 17c) provides the 12 bit D/A converter 452 and the 12 bit latch 454 functions to produce the analog test signal. The chip 560 is provided 12 bits of digital data from the output ports of the EPROM chip 556b over the bus 562. The generated analog test signal is sent over the lines 564 to the scaling operational amplifier 566. The resultant signal is coupled to the A/D converter 408 through the test switch 444 (FIG. 17f).

Two standardized commercially available 4 kilobyte EPROM chips 568a and 568b (FIG. 17e) add an additional 8 kilobytes of read-only memory, thus totaling the fourteen kilobytes of program memory 404. These EPROM chips 568a and 568b are also accessed across the address/data bus 558. However, since these are standardized commercial EPROM chips, a latch 570 (FIG. 17d) is needed to latch out the lower eight address bits from the address/data bus 558. These lower eight address bits are sent to the EPROM chips 568a and 568b over the address only bus 572. A chip select decoder 574 (FIG. 17b) determines which EPROM chip 568a or 568b contains the sector of memory being addressed.

Five 8 kilobyte by 8 bit static random access memory (RAM) chips 576a, 576b, 576c, 576d and 576e (FIGS. 17b-17d) provide the 40 kilobytes of random access memory comprising the storage memory 406. Preferably these RAM chips 576a-e are standardized commercially available chips, and thus, the addressing scheme described above relative to the EPROM chips 568a and 568b is again necessary. Accordingly, when the CPU 402 addresses a memory location in one of these chips across the address/data bus 558, the latch 570 will latch out the lower eight address bits which are provided to the chips 576a-e over the address only bus 572. A chip select decoder 578 enables the appropriate RAM chip containing the address to be accessed. The chip select decoder 578 is provided conditioned power through the opto-isolator 580 (FIG. 17a) which disables the RAM chips 576a-e when power is low, thus preventing data changes in the RAM chips when power is turned ON or OFF.

The timing signals for the EPROM chips 556a, 556b, 556c, 568a and 568b, the RAM chips 576a-c and the UART 500 is generated by the timer chip 582 (FIG. 17e).

The specific implementation of the functions of the dedicated processor 14 in hardware, as shown in FIGS. 17a-f and described above, is but one way in which the dedicated processor could be constructed. Other implementations of the dedicated processor and arrangements and selection of specific chips and components which accomplish the same objective will be apparent to one skilled in the art.

OPERATION

Referring now to FIGS. 18-25 and 29-34 there are shown several flowcharts illustrating the operation of the general processor 16 and dedicated processor 14. Various steps in the operation will be referenced in the following discussion by a number contained within parentheses ( ) which corresponds to an identical number in the figures. Note that as used in the figures an arrow pointing toward a letter or number indicates that the routine will jump to the step on the flowchart indicated by another arrow extending from the same letter or number encircled at another location on the flowchart. The various flowcharts illustrate a preferred structure that, given the ensuing discussion, one of ordinary skill in the art could reduce to computer program code suitable for execution by the resident processor or some other computer program executing device or system.

To begin a DSR test the power must first, of course, be turned on via power switch 43 if it has not been turned on already. Upon power up, the general processor 16 and dedicated processor 14 will perform their initialization routines. The general processor 16 will perform those functions conventionally performed at power up by an IBM compatible microcomputer. The dedicated processor 14 will execute a software reset of the CPU 402 (step 800, FIG. 20) thus zeroing its program counter and causing it to perform its initial functions, such as clearing its memory and setting up its ports (802), and preparing for communication with the general processor 16 (804).

The operator will then weigh or measure out an approximate amount of the test specimen and place it in the cavity 152 of the specimen container 148. The rotor and stator temperature controllers 58, 60, respectively located on the lower control panel 56 on the front face of the DSR 12 are set to the temperatures that it is desired that the test specimen be heated. Preferably, both temperature controllers will be set to approximately the same temperature to ensure an even temperature throughout the test specimen. The stroke timer 62, also located on the lower control panel 56, is set with a preheat time selected large enough to ensure that the test specimen will reach the temperature selected on the temperature controllers 58, 60 before being deflected. The operator will also set the external program switch 502, located on the front face of the dedicated processor 14, to a position indicating whether PROGRAM I, or PROGRAM II or PROGRAM III is to be performed.

Once the general processor 16 has completed its initialization functions, the operator may then command the general processor to begin execution of the desired program. The executable code within the general processor is generally divided into or considered as two segments: the first, which executes PROGRAM I or PROGRAM II, is run by entering, or typing the characters, DSR1 or DSR2 at the operating system level; the second, which executes PROGRAM III, is run by entering DSR3 at the operating system level. The reason for the distinct segments of code is that since PROGRAM I and PROGRAM II may be executed solely within the dedicated processor 14, the DSR may be configured to operate under certain embodiments without the action of the general processor. However, to perform the functions required by PROGRAM III, and to allow a high degree of operator interaction, if desired, PROGRAM III requires the use of the general processor. Depending on the command entered, the general processor will display main menu 1 (FIG. 18, 600), corresponding to PROGRAM I or PROGRAM II, or main menu 2 (601), corresponding to PROGRAM III. Notice that many of the selections provided by the menus are identical, such as calibrating the DSR system, changing the system configuration, performing an operation verification function, or returning to the operating system.

Before examining the functioning of the code which performs the selected test, PROGRAM I, PROGRAM II, or PROGRAM III, the common functions will be discussed. Exiting to the operating system, in this case, DOS, is self explanatory. It allows the operator to switch from performing PROGRAM I or PROGRAM II tests to a PROGRAM III test, or vice-versa. It also allows other functions or programs typical of a microcomputer to be executed. The DEAD WEIGHT CALIBRATION option (generally, 602) provides a method of calibrating the DSR system. Briefly, a known weight is suspended and connected to the system in a fashion which causes it to exert a known force on the load cell. Through interaction with the dedicated processor 14, the corresponding torque measured by the DSR system is displayed on the 4 digit LED display 490. Based on that display a technician can calibrate the system, such as by adjusting the manual zero 422 and span 412 to produce the correct value. The VERIFY option (604) allows the operator to interact with the dedicated processor 14 (see FIG. 23) through the general processor 16, such as to set the start level or to perform diagnostics. Similarly, the CHANGE CONFIGURATION option (606, FIG. 18) allows the operator to modify system default values, such as degree of curve fit, rotor height, shift times, etc., some of which are also transferred to the dedicated processor 14.

An option available from menu 1 only is the INPUT PROGRAM II DATA FILE option, which as is described more fully later, allows the operator to enter a previously stored PROGRAM II data file for graphical manipulation, such as by changing the curve fit or scaling factors. An option available from the PROGRAM III menu, main menu 2, only is the CHANGE DSR FIXTURE DIMENSIONS option. This option allows an operator to change critical geometric values, such as those which comprise the form factor. Since these values are necessary only to the conversion performed in PROGRAM III from torque to shear stress relaxation values, and the determination of the fundamental viscoelastic properties derived therefrom, modification of the values are not permitted when running PROGRAM I or PROGRAM II.

Figure 18A:
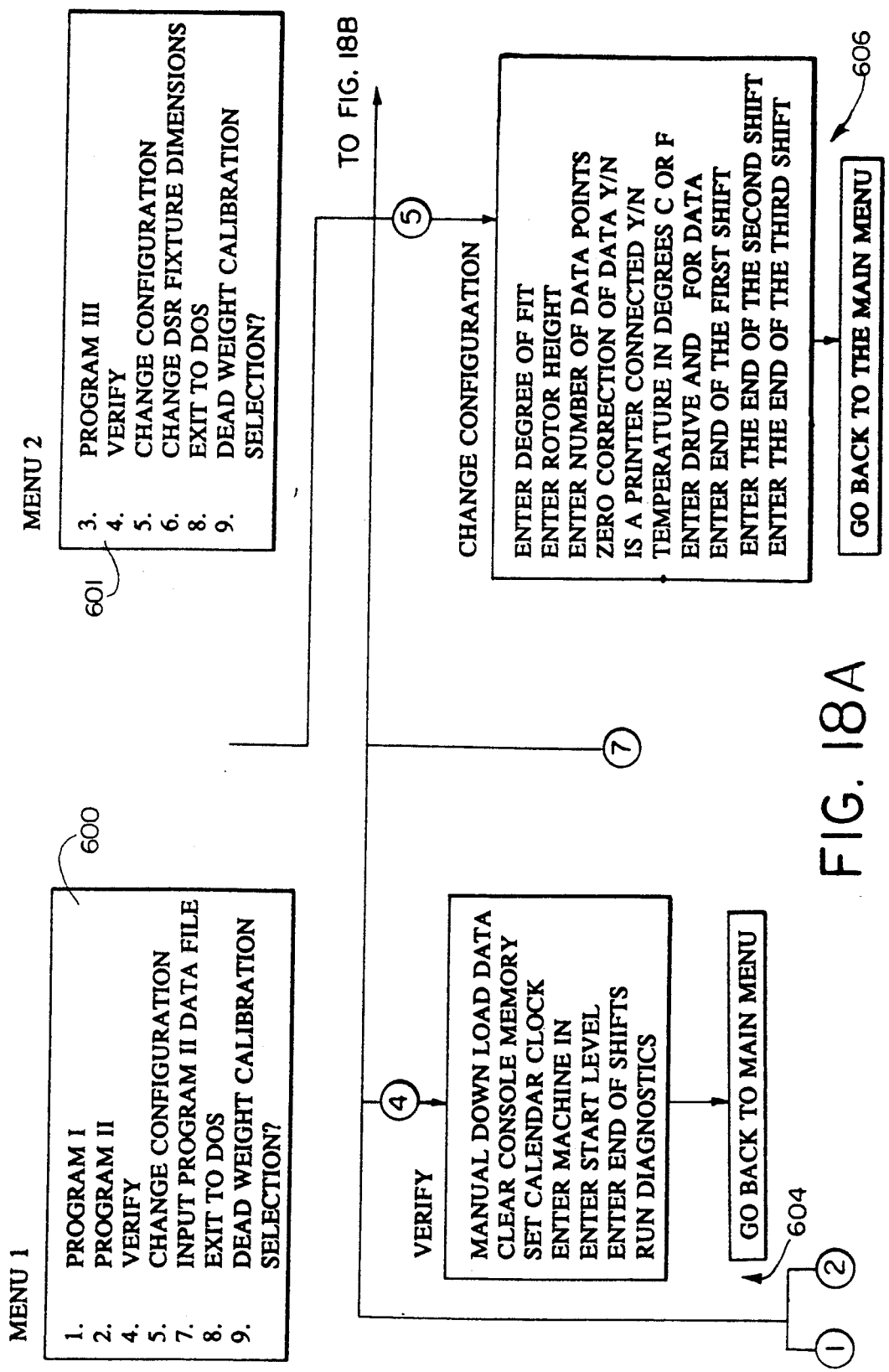
FIGS. 18 and 19 are flow charts illustrating the functioning of general software within the general processor including parts of PROGRAMS I, II and III.
Figure 18B:
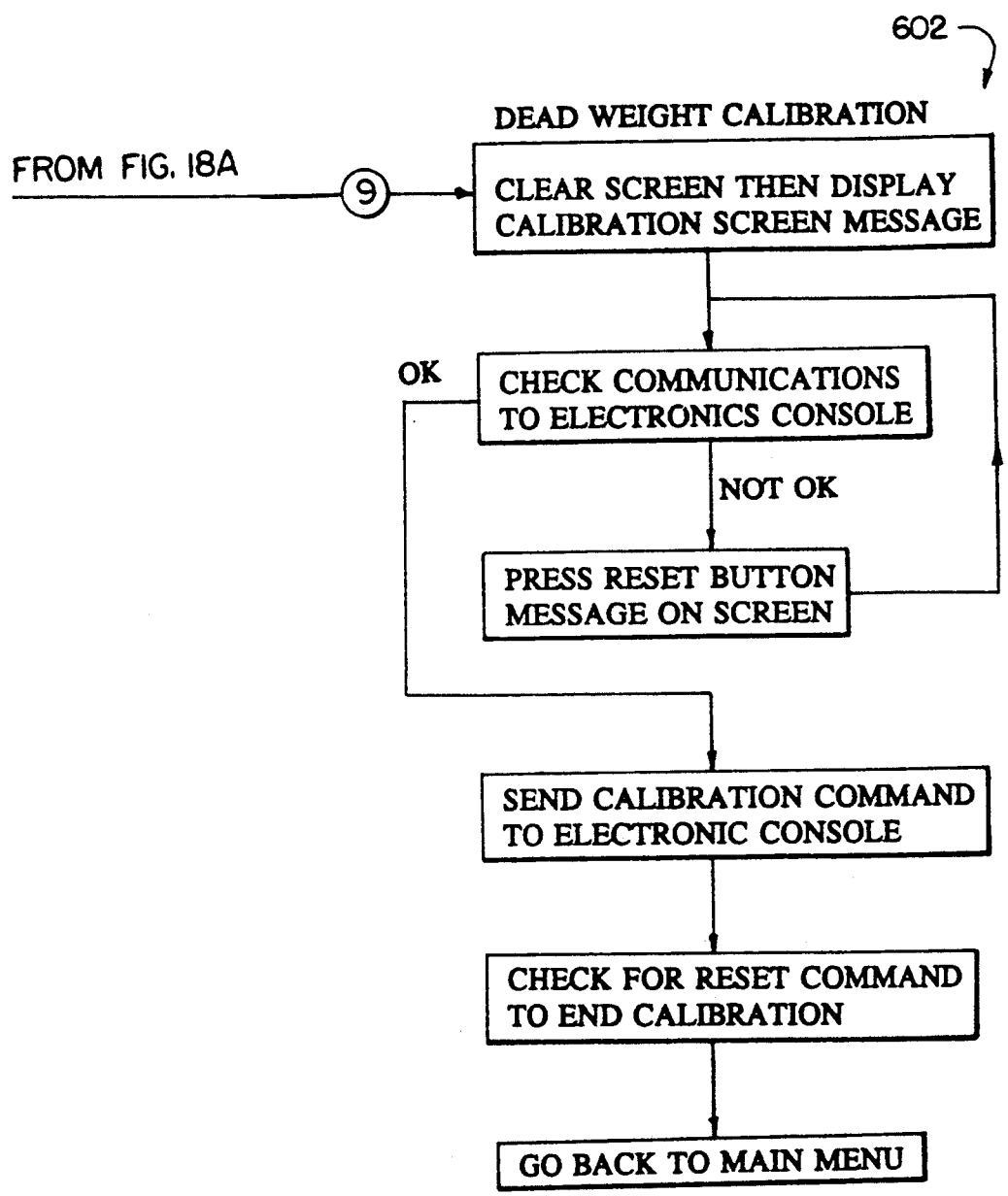
Figure 19A:
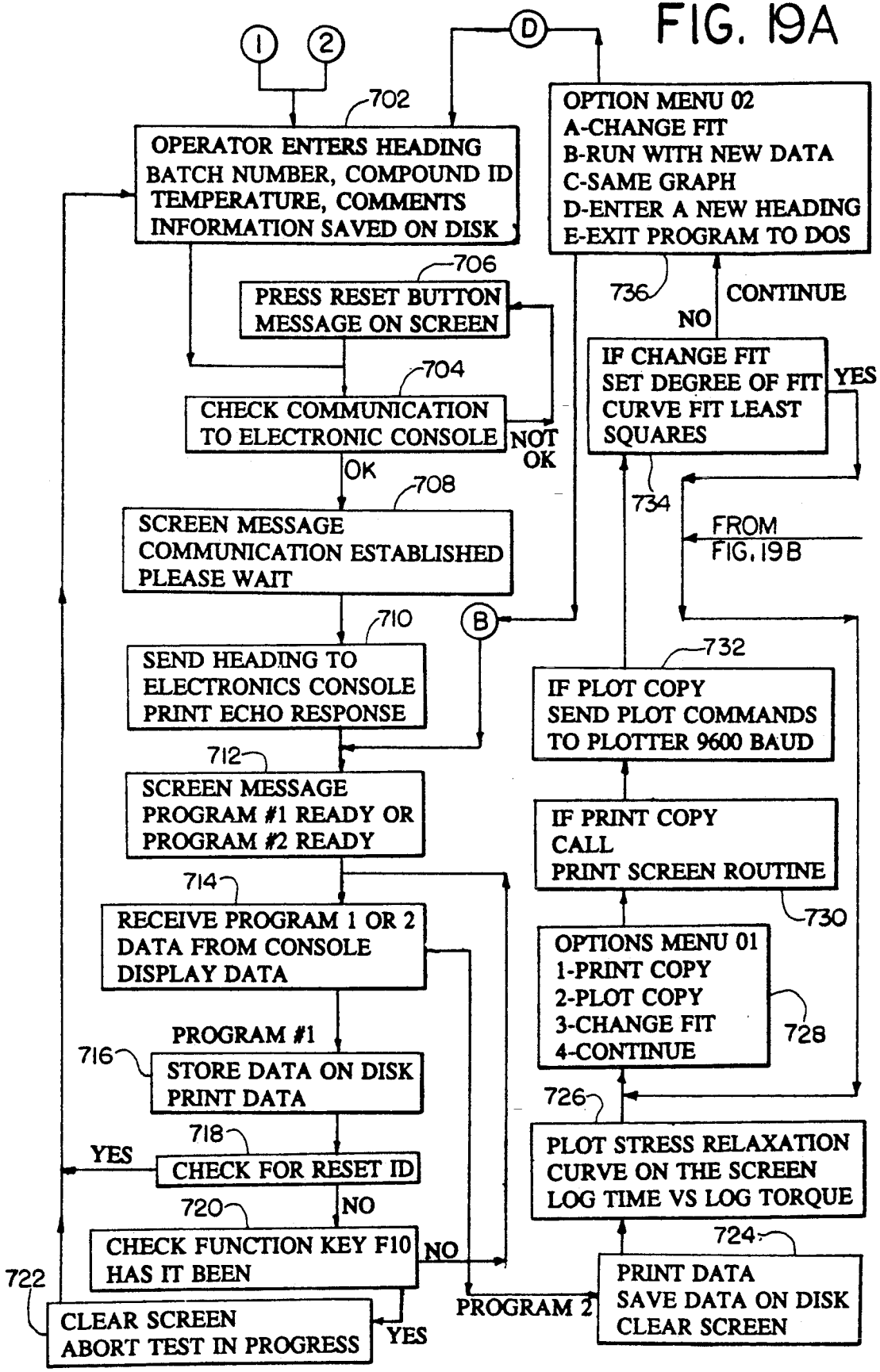
Figure 19B:
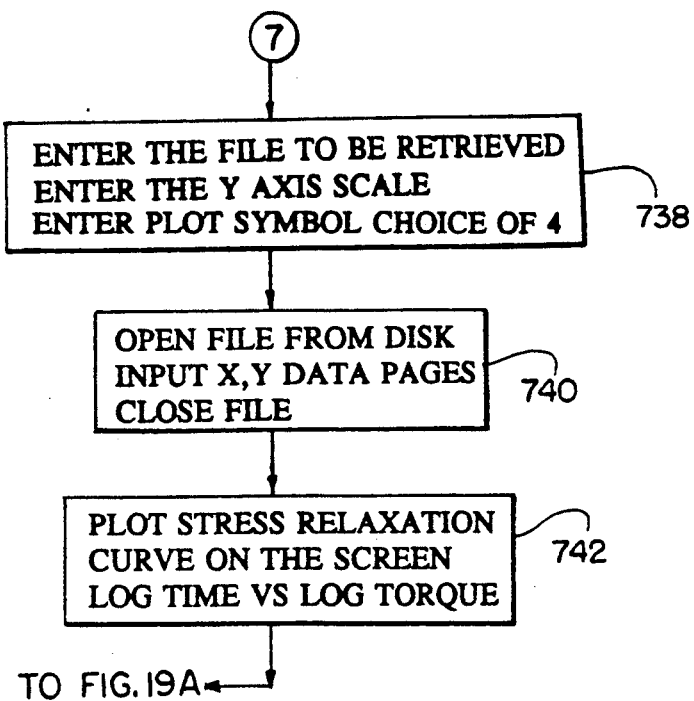
Figure 20:
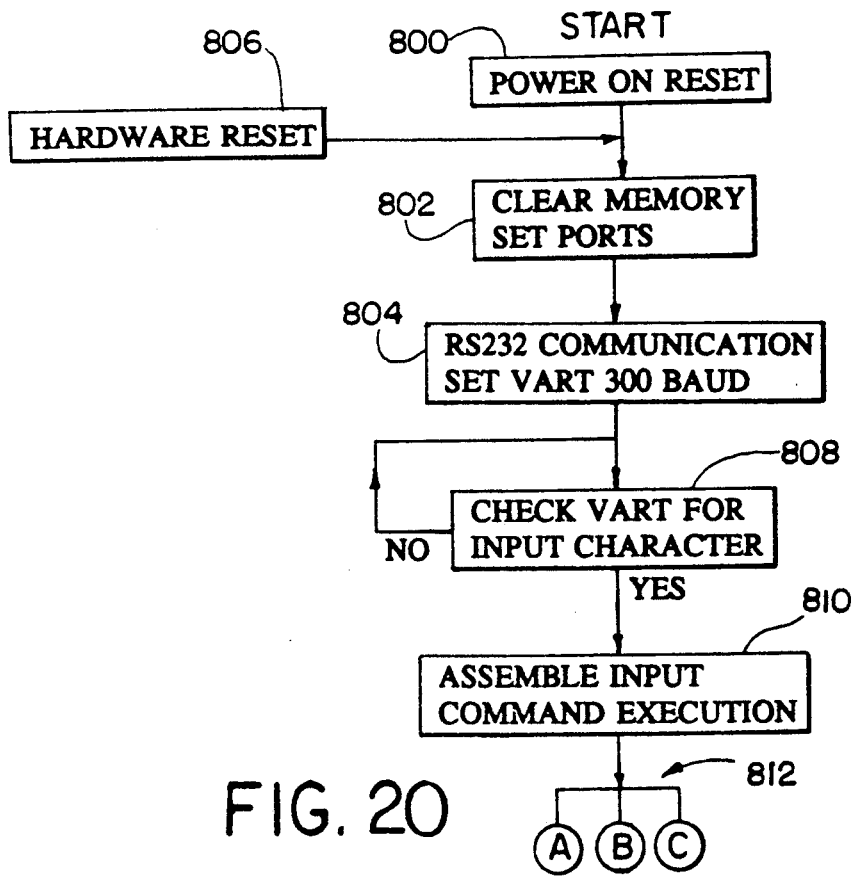
FIGS. 20 through 23 are flow charts illustrating software functions of the dedicated processor including parts of PROGRAMS I, II and III.

To perform a DSR test of a viscoelastic material the operator will select the specific test desired to be performed, PROGRAM I, PROGRAM II or PROGRAM III, from applicable main menu (600 or 601 FIG. 18). If PROGRAM I or PROGRAM II has been selected, the general processor 16 will jump to a routine that controls the test functions of the dedicated processor 14 (FIG. 19). That routine then prompts the operator to enter information identifying the material to be tested and various test parameters (702), such as the test temperature (i.e., the temperature entered into the rotor and stator temperature controllers 58, 60). The routine will then attempt to establish communication with the dedicated processor 14 over the RS-232 data bus (704). If communication is not successful, the processor will instruct the operator to reset the dedicated processor 14 (706). This executes a hardware reset of the dedicated processor 14 (see FIG. 20, step 806) and causes the dedicated processor to reset its memory and to set its ports (802) and to prepare for communication again (804). The general processor routine then attempts communication again (704, FIG. 19). If communication is established, an appropriate message will appear on the monitor (708) and the routine will begin to serially transfer a command to the dedicated processor 14 indicating whether the PROGRAM I, or PROGRAM II test routines are to be executed (710).

If PROGRAM III has been selected, the general processor will immediately establish communication with the dedicated processor 14 and begin to serially transfer to the dedicated processor the command to execute PROGRAM III code and the number of data points to collect.

The dedicated processor circuitry will obtain the command or commands from the general processor 16 in a bit string format over the data bus (808, FIG. 20), and the bits will be assembled to form individual input commands (810). Based on the assembled command, the dedicated processor 14 will transfer program control to the appropriate routine to execute the PROGRAM I, PROGRAM II or PROGRAM III test routines (812).

If the PROGRAM I test routine has been selected for execution (see FIG. 21), the routine will request and obtain the header information from the general processor (810-812) and store that information in its storage memory 406 (814). The routine will then command the precision timer 458 to begin generating a 4000 hertz clock signal which is set to the A/D converter 408 to establish the digital conversion rate of 4000 12 bit words per second (816). The routine then clears a flag to indicate that a valid test has not yet begun. (Herein the phrase "valid test" is used to denote that the DSR device has actually deflected the test specimen.) The CPU 402 then begins accessing words from the programmable interface device 462, checking the start flag to determine if a valid test is in progress (818) and comparing each word against a preset value to determine whether a valid test has begun (820), as will be discussed more fully below. Since a valid test should not have yet occurred, the routine will stay in a loop (818-820) accessing words and checking the start flag (818), which will indicate that a valid test is not in progress, comparing the newly accessed word to a start level (820), which the word should not exceed since a valid test is not in progress (818-820), and then accessing another word to begin the loop again.

If PROGRAM II or PROGRAM III has been selected (see FIG. 22), the routine handling these tests will also request and obtain necessary information from the general processor (852-854) and store that information again in the storage memory 406 (856). The precision timer 458 will now, however, be commanded to begin generating a 1000 hertz clock signal which is sent to the A/D converter to establish the digital conversion rate of 1000 12 bit words per second (858). The start flag will be cleared to indicate that a test is not in progress. The CPU 402 then begins accessing words from the programmable interface device 462, checking the start flag to determine if a valid test is in progress (860) and comparing each word against a preset value to determine whether a valid test has begun (862), as will be discussed more fully below. Since a valid test is not in progress the routine will loop (860-862), as is described above relative to PROGRAM I, waiting for the test to begin.

From the time that the dedicated processor 14 has been commanded by the general processor 16, through an operator selection from the main menus, to perform a PROGRAM I, PROGRAM II or PROGRAM III test, the dedicated processor will continue to convert the input signal from the load cell 206 to corresponding digital words which are analyzed by the selected routine to determine whether the test sample has been deflected.

It should be noted that to this point many of the functions performed by the operator, such as setting the temperature controllers, selecting the test to be performed from the main menu, placing the test specimen in the specimen cavity, etc., may be performed in a different order than that presented above. The order depicted above is illustrative only; other sequences which accomplish the same end will be apparent to one skilled in the art and are included in the scope of the invention.

Once the operator has entered all information requested by the general processor 16 and that information has been transferred to the dedicated processor 14, the general processor will display a message on the monitor indicating that the DSR is ready to begin a test (712, FIG. 19). Assuming all other operator functions have been performed as outlined above, the operator may then raise the stator assembly by simultaneously holding the switches 44a and 44b in the CLOSE position. This actuates the hydraulic cylinder 80 causing it to elevate the stator table 76 and stator assembly 34 toward the rotor 158.

As the stator table 76 reaches a position approximately 0.050 inches below final closure height, the upper limit switch 112 contacts the bottom surface 120 of the rotor table 74, whereby automated control of the elevation of the stator assembly 34 will raise it to a predetermined distance below the rotor 158. At this point the closure gauges visually indicate to the operator that the stator assembly 34 has reached the height where continued elevation is performed automatically and the operator may then release the switches 44a and 44b.

From this point on the DSR test is completely automated and requires no operator participation until the test has been completed. This greatly improves the reliability and accuracy of the test results and the calculated fundamental viscoelastic properties by eliminating any variables attributable to human interaction. Also, since there is no operator interaction required during the critical period of the test (i.e., the time period from just prior to the deflection of the test sample until the output of the results) the level of skill and attention required of the operator is at a minimum.

As the stator assembly 34 approaches its final closure elevation, the conical surface 156 of the rotor 158 enters the cavity 152 of the specimen container 148 and compresses the test specimen contained therein. This forces discontinuations, such as voids or bubbles, out of the test specimen and extrudes excess specimen material between the outer edge of the surface 156 of the rotor 158, and the cylindrical surface 162 of the specimen container 148. The heating element 184 in the rotor 158, now in intimate contact with the test specimen, thus begins contributing to evenly heating the test specimen sandwiched between the rotor surface 156 and cavity 152.

Once the stator assembly 34 reaches a position just below its final elevation, a second upper limit switch, the fine limit switch 114 contacts the adjustable contact 124 and electrically closes thus starting the preheat stroke timer. This causes the DSR to pause for a preset preheat period (the time entered into the stroke timer 62) to ensure that the temperature of the specimen material has reached its preset temperature. During this period the stator assembly will reach its final elevation, and the residual stresses, created during the compression of the test specimen material contained between the conical surface 156 of the rotor 158 and the surfaces 160, 162 of the specimen container 148, will substantially dissipate.

Air pressure maintaining the cylinder rod 212 in its extended position is then exhausted through port 216 and five seconds are allowed to elapse to ensure that the pressure in the cylinder has returned to ambient. At that time an impulse of approximately 70 psi of pressure is introduced to the cylinder 210 through port 214 to retract the cylinder rod 212. The axial retraction of the cylinder rod 212 is translated into angular rotation by the universal joint 202 and rotor arm 200 through the rotor shaft 168 thus causing the desired rotation of the rotor 158.

Upon the impulsive rotational deflection of the rotor 158 the test specimen contained between the surface 156 of the rotor and the surfaces 160, 162 of the specimen cavity 152 will deform and exert a resisting torque upon the surfaces 158, 160 and 162. This torque is translated back through the rotor shaft 168 and rotor arm 200 to the universal joint 202 where the torque is converted to an axial force exerted through the extension arm 204 to the load cell 206. The stress sensing element or elements of the load cell 206 will convert the mechanical stress developed by the axial force into an analog signal that is proportional to the axial force. This analog signal generated in the load cell 206 is sent over lines 208 to the dedicated processor 14 for processing in accordance with the previously selected test, PROGRAM I, PROGRAM II, or PROGRAM III, as is discussed individually below.

PROGRAM I

Figure 21:
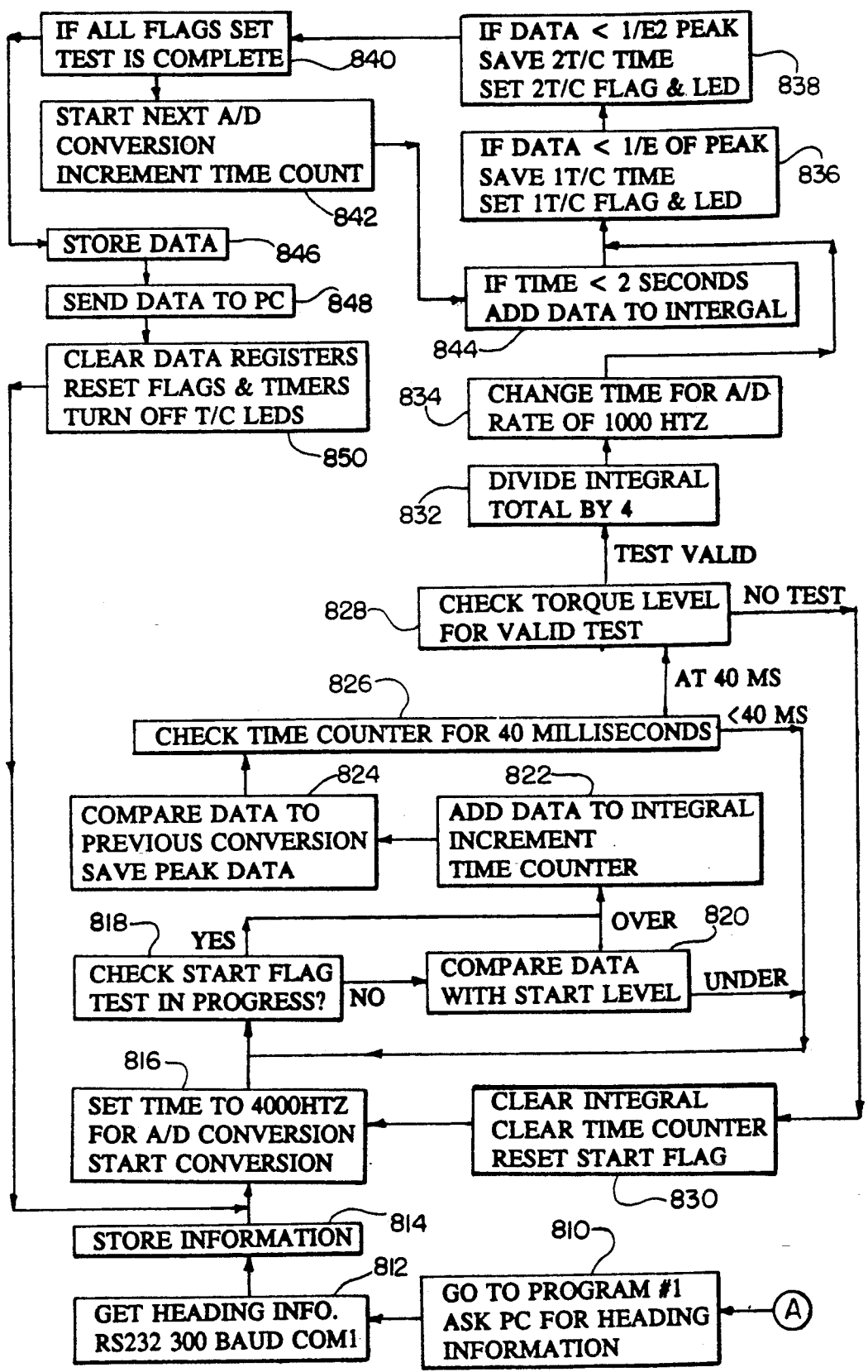

Digressing briefly to the period in time just before the test specimen is deflected and with reference to FIG. 21, it is seen, as mentioned above, that the PROGRAM I test routine has already requested and obtained header information from the general processor 16 (810-812), stored the information in memory (814), set the digital conversion rate to 4000 12 bit words per second (816), and set up a loop to await the beginning of an actual test (818-820). This processing prior to the start of a valid test is necessary because the dedicated processor 14, which is now functioning in a completely automated mode, must itself determine when the actual deflection of the test specimen has occurred and begin to store and to analyze the test data immediately thereafter.

It is possible for the routine to determine when the test specimen has been deflected by comparing the digital data word representation of the scaled and filtered analog signal against certain criteria to which a torque-time response curve of an actual test conforms. To explain, it is known that during an actual DSR test (meaning when the test specimen has actually been deflected) the torsional stress developed in a viscoelastic material subjected to the previously discussed angular deflection will rise to maximum at some point during a 40 millisecond window, usually within 5-10 milliseconds of deflection, and then relax along a generally exponentially response curve. For a given material it is known that this developed stress, and thus the signal generated by the load cell, will exceed a certain known value, called the START LEVEL, which is chosen well below the approximate maximum stress expected to be developed within the test material but above most signals that might be encountered due to stresses developed by compressing the sample to a constant thickness or other anomalies. It is also known that the developed stress will not relax to a value of less than one-half of the START LEVEL at the end of the 40 millisecond window. Consequently, the digitized response curve can be compared to these known characteristics of an actual curve to determine definitely whether the test specimen has been deflected.

Until a data word has been obtained from the programmable interface 462 that exceeds the START LEVEL value it is known that test specimen has not yet been deflected and, consequently, each previous word written to the storage memory 403 will be overwritten. Once a word is examined that exceeds START LEVEL (820) there are two possibilities: 1) that the test specimen has been deflected and the data word is the digitized equivalent of the stress created in the sample; or, 2) that an anomalous signal has occurred on the input line to the dedicated processor. Since the routine cannot ascertain at this time whether an actual test has occurred or whether the signal is an anomaly, the routine assumes the data to be part of an actual test.

Therefore, a 40 millisecond window is initiated and the start flag is set to indicate that a valid test is in progress. The first word that exceeded the START LEVEL then forms the beginning of the two-second integration sum, and the 40 millisecond timer is incremented (822). The accessed data word is then compared to the maximum recorded torque value, which is zero in this case, and thus becomes the temporary maximum torque value (824). The timer is checked to determine if 40 milliseconds has elapsed since START LEVEL was exceed (826). Since 40 milliseconds has not elapsed, no other action is taken and the next data word is accessed and sequentially stored in the memory 406 along with the elapsed time thus beginning the accumulation of a digital representation of the relaxation torque vs. time curve in memory.

The routine will then check the start flag, which will now indicate that a valid test is in progress (818). The data word is then added to the two second integration sum and the 40 millisecond timer is incremented (822).

The data word is compared to the temporary maximum torque value and if the data word exceeds that value, the maximum torque value is updated (824). The timer is then checked again to determine if the 40 millisecond window has expired (826); if not, the next data word is digitized at the 4000 data word per second rate and the loop repeats (818, 822-826).

Once it is determined that the 40 millisecond window has expired (826), the last accessed data word is compared to a value of one half of START LEVEL (828). If this data word is less than one-half of the START LEVEL, the assumption made above (that since a data word exceeded START LEVEL, the test must be a valid test) is deemed to be in error and the test is declared to be an anomaly. The two second integral sum, the 40 millisecond timer, and start flag are then cleared (830), and the test is started anew in a loop (818-820 again searching for a data word that exceeds START LEVEL. Once a valid test is later begun, the new sequentially stored data words will be written over the words previously stored in the storage memory 406 during the invalid test.

If the last accessed data word has not decayed to a value of less than one half of START LEVEL, the test is declared valid and continues. Since the maximum torque for a valid test is known to occur within the 40 millisecond window, the temporary maximum torque value obtained during the window (step 824) must be the maximum torque TM. The test continues by dividing the present two second integration sum by 4 (832) to equally weight it with values subsequently accumulated during the lesser 1000 data word per second rate at which the A/D converter 408 is now set (834).

Since the stresses in the specimen material decay exponentially, the time it takes to decay to approximately zero will be very large and difficult to accurately measure due to the limited 12 bits of resolution of the A/D converter 408 and the comparatively small rate of change of the torque signal at times near the end of the test. For these reasons it is advantageous to base system measurements on well known time constants which are a measure of the time that it takes a signal or function to decay to a certain percentage of its maximum amplitude. The first time constant $T_1$ of a generalized system is defined as $1/e^1$ or 36.79 percent (rounded to the nearest hundredth for convenience of discussion) of the maximum amplitude and the second time constant $T_2$ is defined as $1/e^2$ or 13.53 percent of the maximum amplitude. Consequently, for the DSR system the first time constant $T_1$ will be the time that it takes the digital representation of the torque signal to decay to a value of 36.79 percent of the maximum measured torque TM, and the second time constant $T_2$ will be the time it takes the digital representation to decay to 13.53 percent of TM.

The latest accessed data word, which has been previously added to the two second integral sum (822) and checked to determine whether a valid test is in progress (828), is now compared to a value equalling 36.79 percent of the maximum measured torque TM (mathematically, 1/e*TM), called TC1 (836). If the data word has decayed to a value less than TC1, then the first time constant $T_1$ has been reached and the time in milliseconds since the START LEVEL was surpassed (as determined thus far by step 822) is stored in the storage memory 406 as T1, and a flag is set to indicate that event. At this time the CPU 402 also writes to a port in the program memory 404 to light the LED lamp 482, located on the front face of the dedicated processor 14, to provide a visual indication that the first time constant $T_1$ has been reached. If the data word examined has not decayed to less than TC1, then no action is taken.

Similar to the above step relevant to the first time constant $T_1$, the routine then determines whether the second time constant $T_2$ has been reached (838). The data word is compared to a value equalling 14.53 percent of the maximum measured torque TM (mathematically, $1/e^{2}*TM$), called TC2. If the data word has decayed to a value less than TC2, then the second time constant $T_2$ has been reached and the time in milliseconds since the START LEVEL was surpassed (as determined thus far by step 822) is stored in the storage memory 406 as T2, and a flag is set to indicate the event. At this time the CPU 402 also writes to a port in the program memory device 404 to light the LED lamp 484, located on the front face of the dedicated processor 14, to provide a visual indication that the second time constant $T_2$ has been reached. Again, if the data word examined has not decayed to less than TC2, then no action is taken.

On the first pass through these steps (836, 838) it is unlikely that the digitized representation of the torque vs. time response curve will have decayed to the value at first time constant $T_1$, since the data word compared to TC1 is the first data word accessed at the end of the 40 millisecond window and the test has been determined to be valid. (And, of course, since the value at the second time constant $T_2$ is less than that at the first time constant $T_1$, the second time constant $T_2$ also should not have yet been reached.) Accordingly, it is unlikely that the first or second time constants will have been reached during the 40 millisecond window when the data words were not being compared to TC1 or TC2.

Next, the routine checks the time constant flags and the test time to determine if the test has been concluded (840). If both flags are not set, indicating that at least the second time constant $T_2$ has not yet been reached, or the test time is less than two seconds, then the test is not over and another data word is accessed for processing and the test time is incremented (842). If the test time is still less than 2 seconds, the data word is added to the two second integration sum (844). The data word is then compared to TC1 and TC2 to determine if the first or second time constants have been reached (836, 838) and the time constant flags and test time are again examined to determine if the test has been concluded (840). The routine remains in this loop (840, 842, 844, 836, 838, 840) accessing data words, adding them to the two second integral sum and comparing the words to TC1 and TC2 until both time constants have been reached and the two second integral has been calculated.

Once the test is completed, the data (T1, T2, the torque v. time coordinates and the two second integral) are stored (846) and sent to the general processor 16 over the RS-232 data bus (848). The data registers are then cleared, all flags and the test timer are reset, and the LED displays are turned off (850). The routine then sets the A/D converter 408 to the 4000 data word per second rate (816) and begins a loop searching for the start of a new test (817, 818, 820).

The general processor 16 on the other end of the RS-232 data bus receives the test information from the dedicated processor 14 and displays the data in numerical form on the display monitor 20 (714, FIG. 19). That data is then stored on the hard disk or floppy disk of the general processor 16 and printed on the attached printer 17 (716). The routine executing within the general processor 16 then checks to see whether the reset switch has been depressed (718). If so, the test running within the dedicated processor 14 has been aborted, and the operator is prompted to again enter information for a new test (702). If the reset button has not been depressed, the routine will determine whether the operator has chosen to alter the test information, which is indicated by pressing the function key F10 (720). If the function key has been depressed, the display monitor is cleared and the PROGRAM I test in progress in the dedicated processor 14 is aborted (722), and the operator is again prompted to enter new test information data (702). If the function key has not been depressed, then the routine again waits to receive new PROGRAM I test data from the dedicated processor 14 (714).

As can be seen from the above, if it is not necessary to re-enter test information data and a reset has not occurred, the dedicated processor 14 and general processor 16 are autonomously performing repeated PROGRAM I tests, accumulating, analyzing and storing data for numerous tests, without operator intervention. Consequently, once PROGRAM I has been selected from the main menu (700 FIG. 18), and the operator has entered the requested test information, such as at the beginning of a shift, no interaction between the operator and the general processor 16 or dedicated processor 14 is necessary during subsequent DSR tests. The operator simply places a desired amount of the test material in the specimen cavity, closes the DSR machine, and then waits for the DSR to perform the test itself, when the test is over the operator opens the DSR machine, replaces the used test sample with a new test sample and again closes the DSR machine to perform the next DSR test. This process may be repeated indefinitely until it is desired to perform a test on a different type of material or to change the testing parameters or testing information.

PROGRAM II/PROGRAM III

As is discussed above, the routine executing the PROGRAM II and PROGRAM III tests is already running prior to the actual deflection of the test specimen. It has requested and obtained header information from the general processor 16 (852-854, see FIG. 22), stored the information in memory (856), set the digital conversion rate to 1000 12 bit words per second (858), and set up a loop to await the beginning of an actual test (860, 862, 864). Whether the routine is executing the PROGRAM II test or performing the data collection aspect of the PROGRAM III test, the routine performs the same operations in detecting when the test specimen has been deflected and in determining whether a valid test is in progress.

As is described more fully with respect to PROGRAM I above, it is known that for a valid test the torsional stress developed in a viscoelastic material subjected to the previously discussed angular deflection will rise to maximum at some point during a 40 millisecond window, exceeding a certain known value, called the START LEVEL, and then relax along a generally exponentially response curve. It is also known that the developed stress will not relax to a value of less than one-half of the START LEVEL at the end of the 40 millisecond window. Consequently, these criteria are again used to evaluate whether a signal corresponds to an actual test, or is the result of an anomaly.

The routine thus accesses a data word from the programmable interface 462 (860) which is collecting data words from the A/D converter 408 at a rate of 1000 words per second. Assuming the routine has not already determined that a test is in progress, data words are accessed and examined in a loop until it is determined that START LEVEL has been exceeded (860, 862, 864). When START LEVEL has been exceeded, the start flag is set and a 40 millisecond window is opened (866). It should be noted that the value for START LEVEL is offset by 96 digital counts, thus corresponding to 9.6 inch-lbs$_f$ from that entered by the operator prior to the start of the test. This relates to the 9.6 inch-lbs$_f$ of analog offset added to the analog input signal received by the A/D converter 408 by setting the program switch 502 to the PROGRAM II/PROGRAM III position.

As further words are accessed (860), the routine will check the start flag (862) and note that a test is in progress. Consequently, the routine will increment the test timer (866) and examine it to determine whether 40 milliseconds have elapsed since START LEVEL was surpassed (868). The routine will continue in this loop (860, 862, 866, 868) until the test timer has been incremented sufficiently to exceed 40 milliseconds. Once the 40 millisecond window has closed, the routine checks the last data word accessed to determine whether it has dropped below one-half of START LEVEL (870). If it has, the test is declared an anomaly, the test timer and start flag are reset (872), and the routine again sets up a loop wherein it repeatedly accesses data words and compares them to START LEVEL to detect the start of a new test (860, 862, 864). If, however, the data word accessed at the end of the 40 millisecond window was above one-half of START LEVEL (870), the test is declared to be valid and the CPU 402 will turn on LED lights 482 and 484 (corresponding to the time constant LEDs of PROGRAM I) by writing to the appropriate ports in the program memory 404 to indicate that a valid test is in progress (874). At this point the routine also determines whether the operator had selected either the PROGRAM II or PROGRAM III test to be performed, as are described separately in the subsections below.

A) PROGRAM II

If PROGRAM II has been selected, the routine will next collect 21 data points at evenly logarithmically spaced intervals between 0.04 seconds to 400 seconds and temporarily store the data along with the corresponding times (876). When all of the data has been collected, after 400 seconds, the CPU 402 writes to a port in the program memory device 404 which lights the ready LED 488 to provide a visual indication to the operator that all data has been accumulated. The sample is then removed. The operator then presses the zero switch 500 on the face of the dedicated processor 14 which instructs the CPU 402 to read the output of the load cell at zero torque. This zero value indicates the drift of the load cell 206 over the comparatively long PROGRAM II test. The routine then corrects the collected data points based on the zero value to improve the accuracy of the results, performs a logarithmic based conversion of the data points and restores the corrected log based data points (878).

The results are paired log-torque vs. log-time data points which are sent to the plotter 18, such as to produce the representative graph of FIG. 5, and to the general processor 16 for numerical and graphical display on the attached monitor 20 (880). The routine then clears the data registers, resets the start flag and the test timer, turns off the LEDs (882), and begins looping to find the start of a new test (860, 862, 864).

Once the general processor receives the PROGRAM II data from the dedicated processor 14 (714, FIG. 19), the numerical data is printed on the attached printer 17, and saved on a hard or floppy disk (724). The general processor 16 then plots a log torque versus log time stress relaxation curve on the display monitor 20 (726) and displays a number of continuing selections (728) for the operator to chose (728) such functions include printing or plotting a copy of the stress relaxation curve (730, 732, respectively), or changing the degree of fit of the curve drawn through the torque versus time coordinates (734). In each of these circumstances once the function is performed, the routine returns to the menu to allow the operator to select another function. Once all desired functions have been performed, the routine continues to the second menu which allows the operator to select from a separate set of additional functions, such as changing the preset curve fit, returning to the PROGRAM II test, saving the log torque versus log time stress relaxation curve on disk, entering new test information, or exiting the program to the main operating system, such as DOS (736).

As with PROGRAM I, PROGRAM II requires only a small amount of operator interaction. In fact, if the operator desires to simply continue running repeated PROGRAM II tests, he need only provide responses to two prompts (728, 736), selecting the continue option in the first instance, and in option 2 to re-run PROGRAM II with new data in the second instance.

PROGRAM II test data which has been stored on disk can be recalled from the main menu 700 by selecting the appropriate choice. In this case the routine prompts the user to enter the file containing the data to be retrieved (see FIG. 19, step 738). The routine then opens the file, retrieves the data (740) and displays the log torque versus log time stress relaxation curve on the display monitor 20 (742). The routine then allows the operator to select the functions provided through menus 1 and 2 described above (728, 736) including printing or plotting the curve (730, 732), changes the degree of fit of the curve (734) or performing PROGRAM II test run with new data, etc.

B) PROGRAM III

Figure 22:
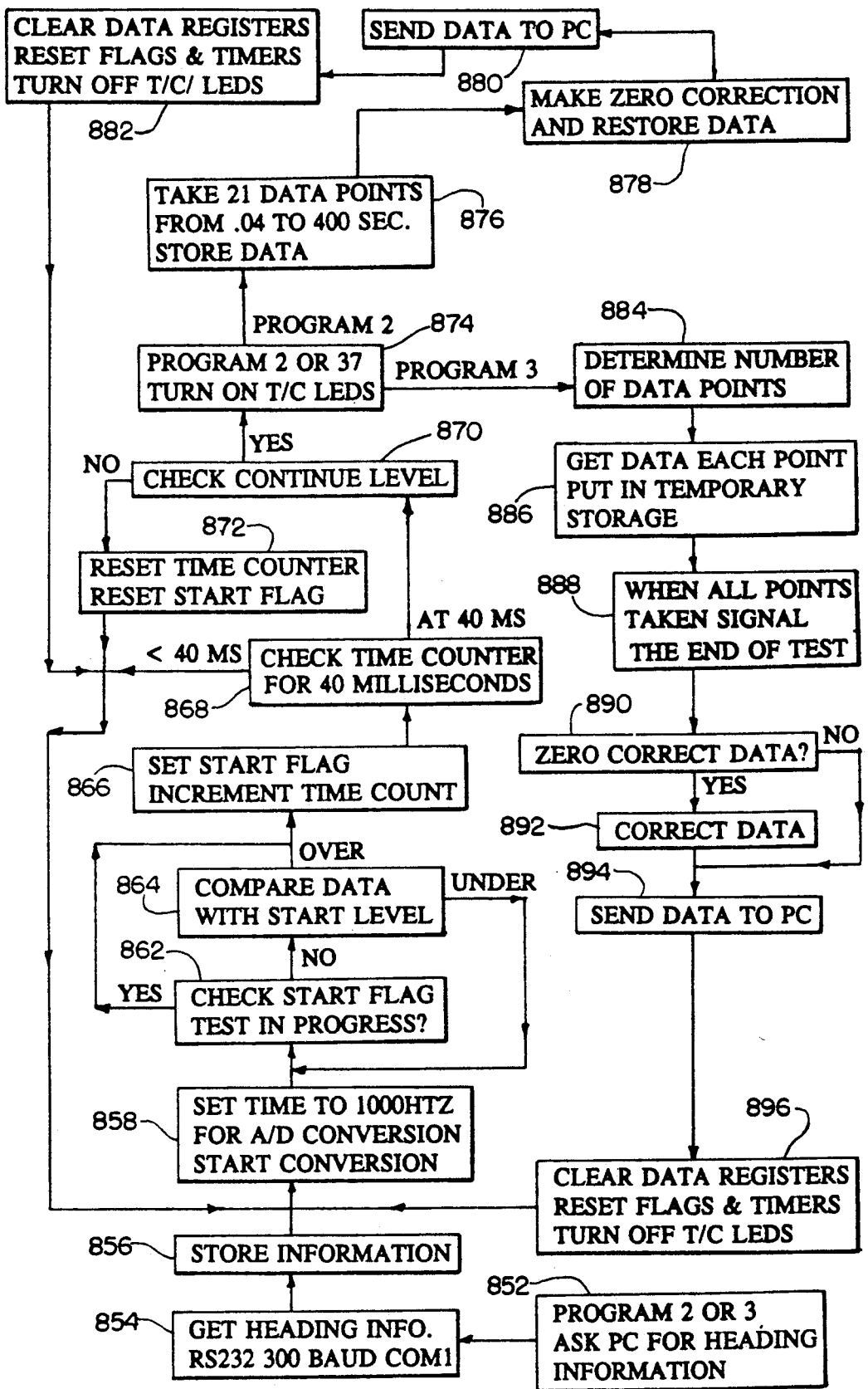
Figure 23:
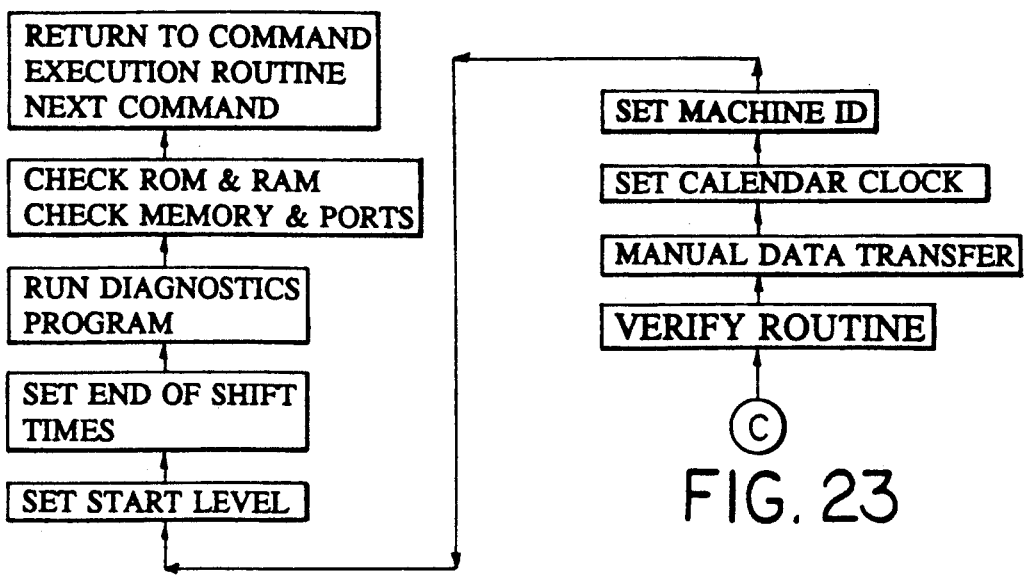
Figure 25:
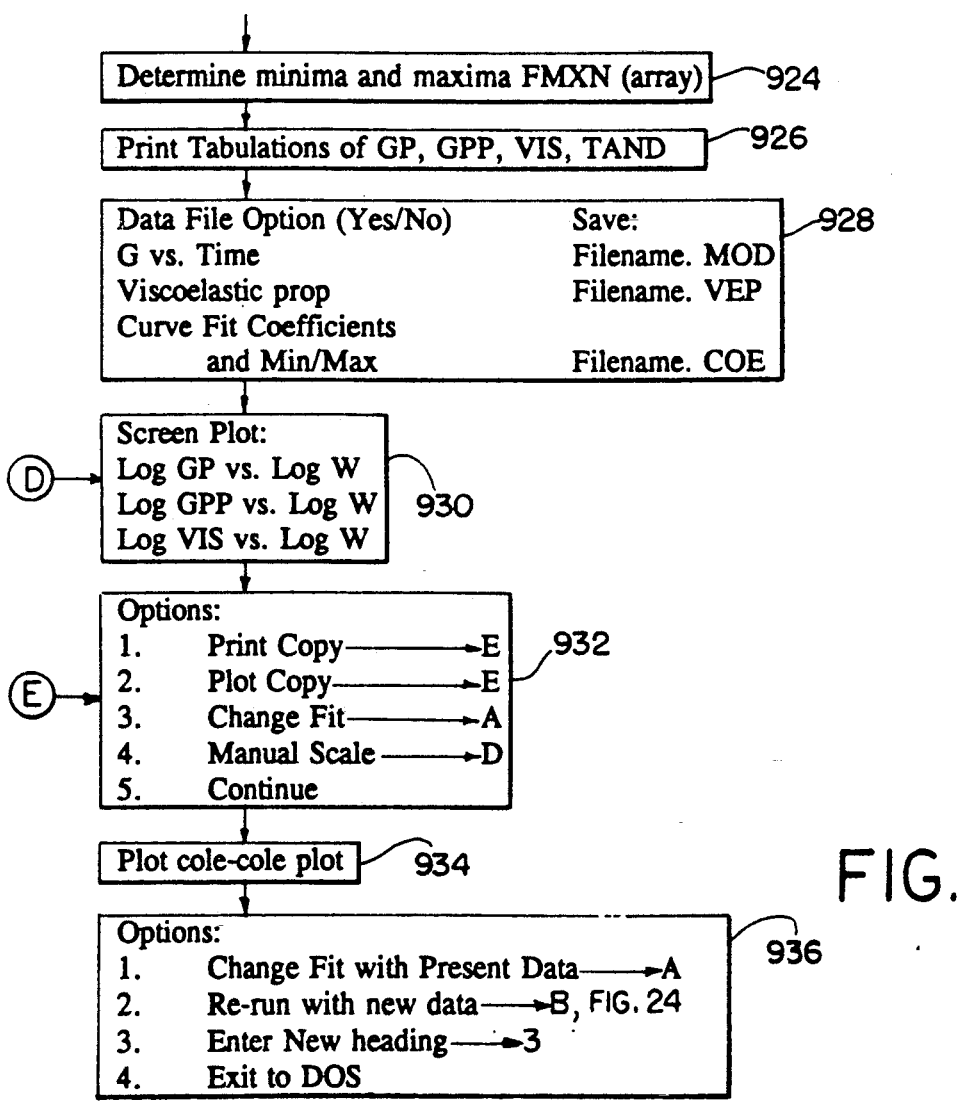
FIGS. 24 and 25 are flow charts illustrating the functioning of code within the general processor related to PROGRAM III data analysis.
Figure 24:
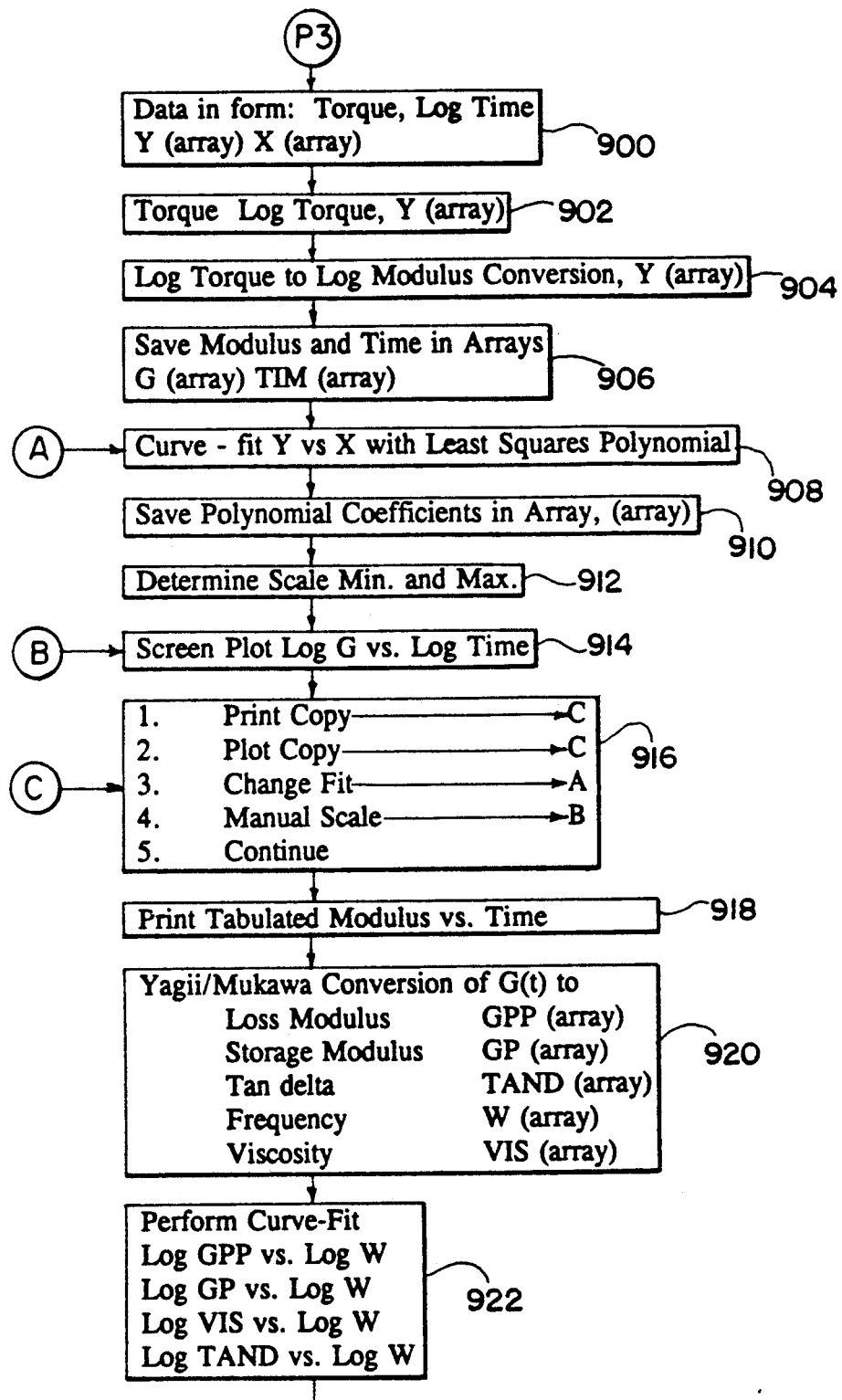

If the PROGRAM III test has been selected, the routine executing within the dedicated processor 14 will have been previously provided with the number of data points that were selected for collection (884, FIG. 22). The routine then collects that many evenly logarithmically spaced data points and temporarily stores the data points in memory with a corresponding time (886). Once all of the data points have been collected, the CPU 402 writes to a port in the program memory device 404 which lights the ready LED 488 to provide a visual indication to the operator that all data has been accumulated (888). The operator then removes the sample from the DSR and presses the zero switch 500 on the face of the dedicated processor 14 which instructs the CPU 402 to read the output of the load cell at zero torque. This zero value indicates the drift of the load cell 206 over the comparatively long PROGRAM III test. The routine then determines if data correction is necessary (890), and, if so, the routine corrects the collected data points to improve the accuracy of the results (892).

The torque vs. log time data points are now transferred to the general processor 16 over the RS-232 data bus for further processing by the general processor in accordance with PROGRAM III. The routine executing in the dedicated processor then clears the data registers, resets the start flag and the test timer, turns off the LEDs (896), and begins looping to find the start of a new test (860, 862, 864).

The remainder of PROGRAM III data analysis is executed in the general computer 16 with the log-torque vs. log-time data pairs computed by and received from the dedicated processor 14 over the RS-232 bus (FIG. 19, 714). The PROGRAM III routine of the general processor 16 stores the torque data points and the log time points in separate one dimensional arrays (see FIG. 24, step 900), called TORQUE(array) and X(array), respectively. Hereinafter, both in the discussion and in FIGS. 24–25 and FIGS. 29–34, software variable names are denoted by all capitals. Further, those variables that are also arrays are denoted by the use of "(array)" appended to the variable name with the number of uses of "(array)" indicating the dimensionality of the array. For convenience, only the introductory use of an array variable in the discussion and in the figures will include the "(array)" appendix.

The routine then performs a logarithmic conversion of the torque relaxation values in TORQUE and places the results in another one dimensional array, Y(array) (902). The log torque values in Y can then be converted to obtain the logarithm of the relaxation modulus which is restored in Y (904). The log relaxation modulus values in Y are then converted to relaxation modulus values which are stored in G(array) and their corresponding times are stored in TIM(array) (906). The relaxation modulus, commonly abbreviated as G, is used to in the well known Yagii/Maekawa approximation to yield approximations of the fundamental viscoelastic properties of the test material.

The conversion from log torque relaxation values to log relaxation modulus values is possible from a knowledge of the geometry of the test specimen at deflection and the amount of deflection. The geometry of the deformed test specimen is a function of the dimensions of the rotor 158 and the specimen cavity 152, as well as the closure height, all of which have been measured for a particular DSR device 12 and stored in a data file in the general processor 16. A review of the mathematical basis for determining the relaxation modulus is discussed below.

The torque, represented in equation 1 as T, measured during the DSR test is dependent upon the stress generated within the test specimen (confined between the conical surface 156 of the rotor 158 and the surfaces 160 and 162 of the specimen container 94) and transmitted to the conical rotor surface, is described by Equation 1:

$$T = \int^A R \cdot \tau \cdot dA \qquad (1)$$

where
$\tau$ = shear stress
R = moment arm
A = surface area of rotor

In Equation 1 the shear stress $\tau$ can be replaced by the product of the specimen deformation or strain $\gamma$ and the shear relaxation modulus G as shown in Equation 2:

$$T = \int^A R \cdot G \cdot \gamma \cdot dA \qquad (2)$$

If it is assumed that the relaxation modulus G is independent of strain, i.e., that the behavior of the test specimen can be described by linear viscoelastic theory, then G can be considered as a constant with regard to the integration, although it varies as a function of time. Removing G from the integrand yields Equation 3:

$$T = G \int^A R \cdot \gamma \cdot dA \qquad (3)$$

The integral, which relies on an accurate description of the test specimen strain, represents the reciprocal of the geometric form factor between the rotor 158 and specimen container cavity 152. Since the actual geometry of the rotor 158 and specimen container cavity 152 are known, the form factor can be calculated and used to solve equation 3. Since the relaxation torque T is measured during the test, it is also a known value at a given time. Consequently, the shear relaxation modulus G is the only remaining unknown in Equation 3 and it can thus be solved by multiplying the form factor by the measured relaxation torque T.

It is noteworthy that Equation 3 does not consider the effects of strain rate history during the deformation. Typically, classical stress relaxation experiments try to impose a nearly instantaneous deformation on the test specimen. Realistically, however, stress relaxation data generated during the initial time period following the formation are discarded since it is known that data obtained at times greater than 5 or 10 times the time period required to impose the deformation are essentially equivalent to those obtained from an ideally instantaneous deformation. The data captured by the PROGRAM III routine executed within the dedicated processor 14 meet this criterion. Thus, Equation 3 above provides an adequate starting point for the development of a model.

Figure 26:
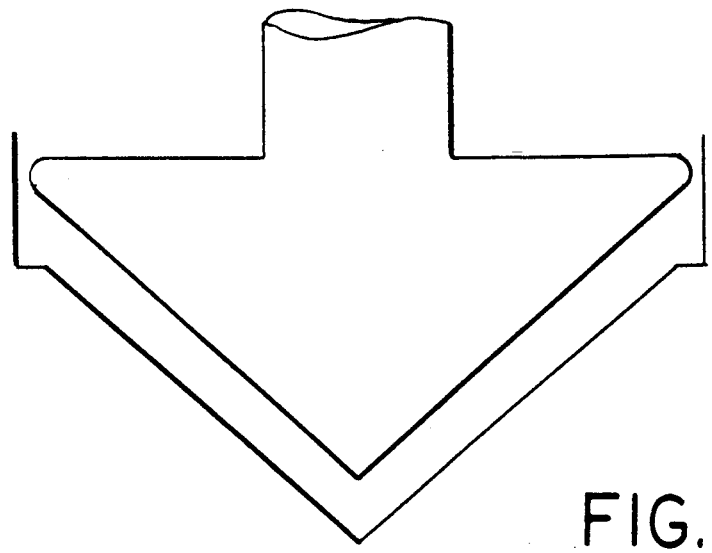
FIG. 26 is a close-up view of the rotor and stator shown at closure.
Figure 27:
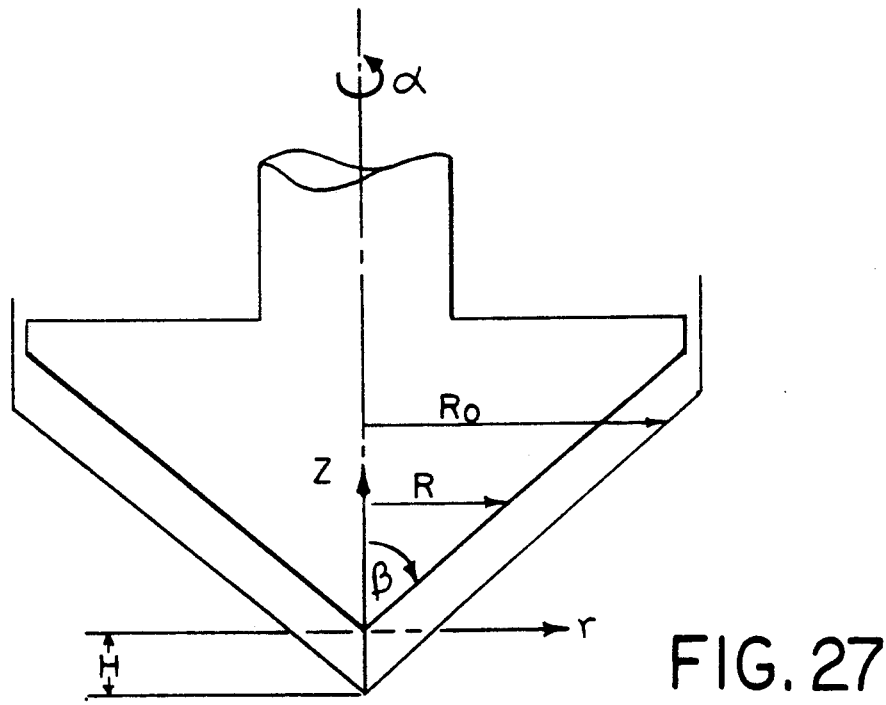
FIG. 27 is a close-up view of the rotor and stator as mathematically modelled.

A close-up view of the actual geometry of the rotor 158 and the specimen container cavity 152 at closure is shown in FIG. 26. To reduce the complexities involved in mathematically modeling this geometry to arrive at its form factor, a few minor approximations are incorporated to arrive at the test geometry as shown in FIG. 27. Also shown in FIG. 27 are the z-r coordinate system and the variables used to define the test geometry. Both the radius of rotor, R, and the radius of the specimen container recess, $R_o$, vary along the z axis. The vertical distance H between the rotor 158 and the surface 160 of the specimen container cavity 152 and the angular deflection, $\alpha$, by which the strain is imposed are operator selectable and thus are treated as variables.

In order to facilitate modeling the strain throughout the test specimen, a transformation to a "local" coordinate system is beneficial. For this purpose the Y-axis is positioned normal or perpendicular to the conical surface 156 of the rotor 158. The local X-axis lies tangential to the rotor surface 156 and points in the direction of the angular deflection $\alpha$. The local strain of an element of "fluid" is thus described by Equation 4:

$$\gamma = \frac{\Delta X}{\Delta Y} \quad (4)$$

where
- $\Delta X$ = tangential movement of a point on the rotor surface resulting from the $\alpha$ angular deflection.
- $\Delta Y = S$, the separation between the rotor and stator along the Y-axis.

The above transformation to a local coordinate system is the basis of the known "lubrication approximation" which permits the description of local strain (as is shown) of an element of fluid confined in a narrow gap as long as the dimensions of the gap are much smaller than the radius of curvature of the gap. The use of the approximation for the DSR becomes questionable at small values of z (values near the points of the conical surfaces); however, the contribution of the stress in this region compared to the total torque is minimal due to the small moment arm, R in the region. As z increases the radius of curvature and consequently the moment arm R increases, thus the accuracy of the overall approximation becomes less questionable.

Figure 28:
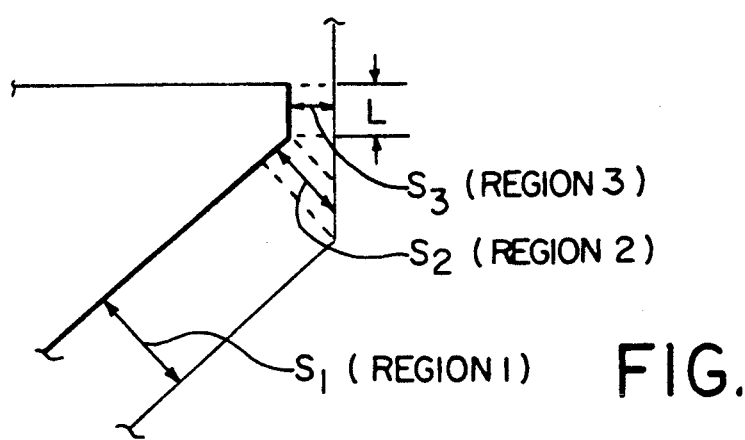
FIG. 28 is a sectional view of the rotor and stator illustrating the individual mathematical modelling regions.
Figure 29:
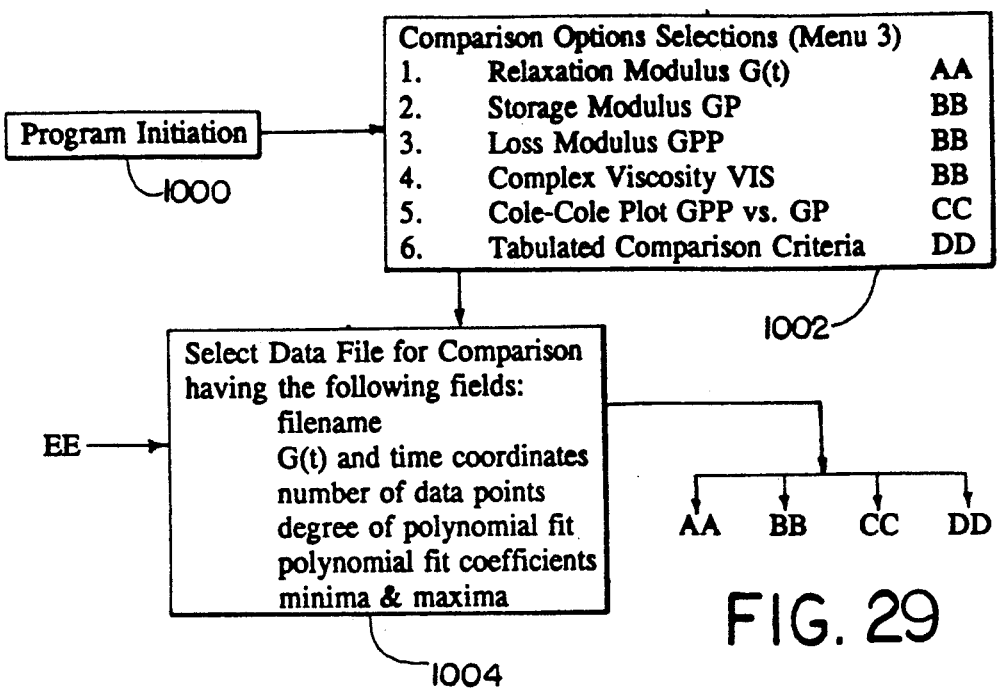
FIGS. 29 through 34 are flow charts illustrating PROGRAM III data comparison functions within the general processor.
Figure 30:
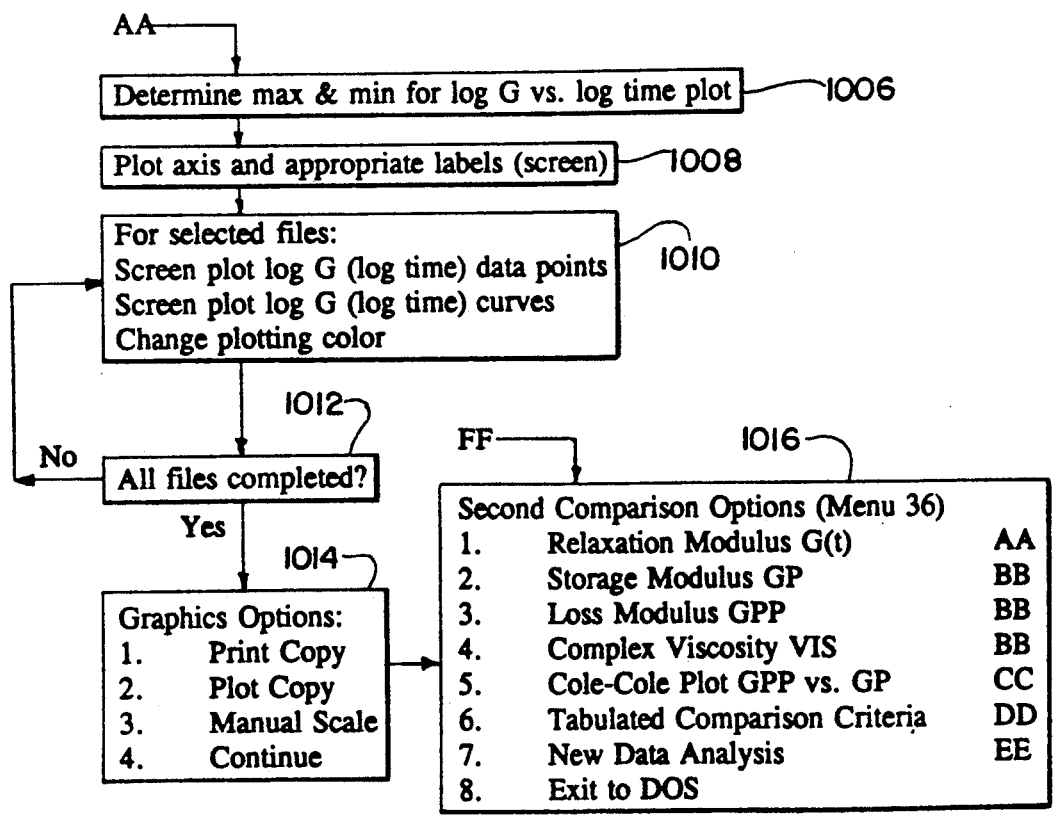

FIG. 28 shows schematically the manner in which $\Delta Y$ or S, the separation between the conical surface of the rotor 100 and the surface of the specimen cavity 94, varies as a function of z. It becomes apparent from the figure that the DSR test geometry requires the consideration of three separate regions. Specifically, the total torque consists of the sum of the torque components for each of the three regions; yielding Equation 5.

$$T = T_1 + T_2 + T_3 \quad (5)$$

A derivation of the strain and torque components for each region yield the following results:

$$\text{Region 1 strain, } \gamma_1 = \frac{\alpha z \tan \beta}{H \sin \beta} \quad (6)$$

$$T_1 = G \cdot B \cdot \frac{(A - H)^4}{4} \quad (7)$$

where $$A = \frac{Ro_{max} + H (\sin \beta)^2}{\tan \beta}$$

$$B = \frac{2\pi \alpha (\tan \beta)^3}{H (\sin \beta)(\cos \beta)}$$

$$\text{Region 2 strain, } \gamma_2 = \frac{\alpha z \tan \beta}{\sin \beta (A - z)} \quad (8)$$

$$T_2 = \quad (9)$$

$$GHB \left[ -\frac{z(A-z)^2}{2} + 2Az(A-z) - A^2 z \ln(A-z) - \frac{(A-z)^3}{6} + A(A-z)^2 + A^2(A-z)(1 - \ln[A-z]) \right]_{z_1}^{z_2}$$

where $z_1$ and $z_2$ are the limits of integration.

$$\text{Region 3 strain, } \gamma_3 = \frac{\alpha R_{max}}{Ro_{max} - R_{max}} \quad (10)$$

where
$R_{max}$ = maximum rotor radius
$Ro_{max}$ = maximum stator radius $$T_3 = \frac{G 2 \pi R_{max}^3 \alpha L}{Ro_{max} - R_{max}} \quad (11)$$

where L = vertical length of Region 3

Substitution of Equations 7, 9, and 11 into Equation 5 provides the mathematical model of the DSR test. Examination of the torque components indicates that G, the stress relaxation modulus, appears as a single multiplication factor (the unknown variable) in each; the remaining terms are all known quantities obtained from either manufactured dimensions of the rotor 158 and specimen cavity 152 or operator selected options (i.e., deflection angle $\alpha$ and closure height H). Thus, the sum of the terms, with G removed as a multiplier, is the reciprocal of the geometrical form factor for the DSR test. The stress relaxation modulus G as a function of time is then obtained by multiplying the measured torque relaxation T as a function of time by the form factor.

Consequently, the log torques values in the array Y are multiplied by a form factor, calculated in accordance with the above mathematical analysis, and again stored in Y to yield the log stress relaxation modulus G (904). These values are then converted back to base 10 to obtain the stress relaxation modulus which is stored in the array G (906).

A least squares polynomial curve fit of a preselected degree is then performed, such as by using Crout's reduction technique, on the stress relaxation modulus and time coordinates, as found in the G and X arrays respectively (908). The polynomial coefficients yielded by the curve fit routine are stored in C(array) (910) for later use in determining the fundamental viscoelastic properties of the test specimen.

Figure 6:
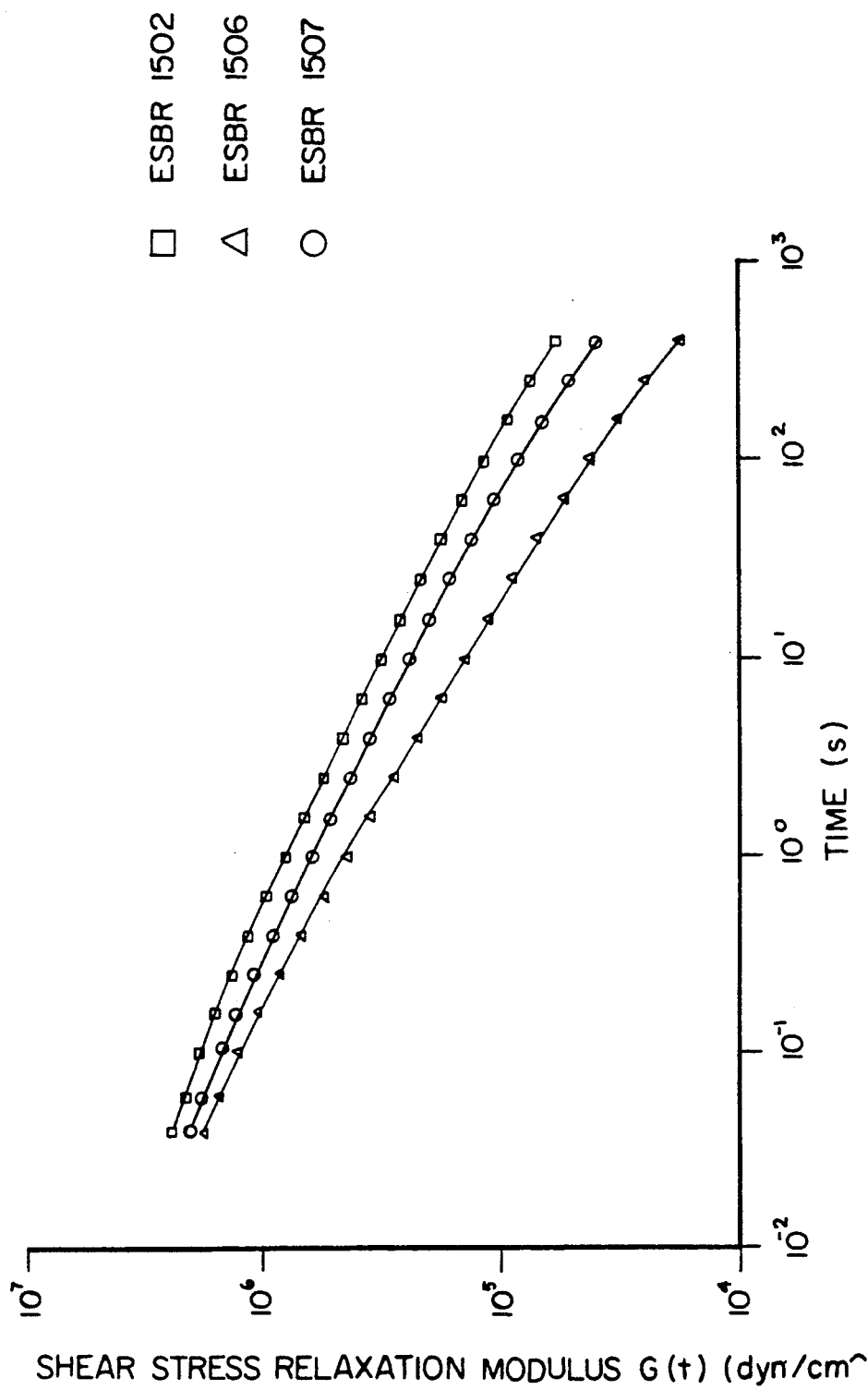
FIGS. 6 through 9 are graphs representative of those produced by PROGRAM III.
Figure 7:
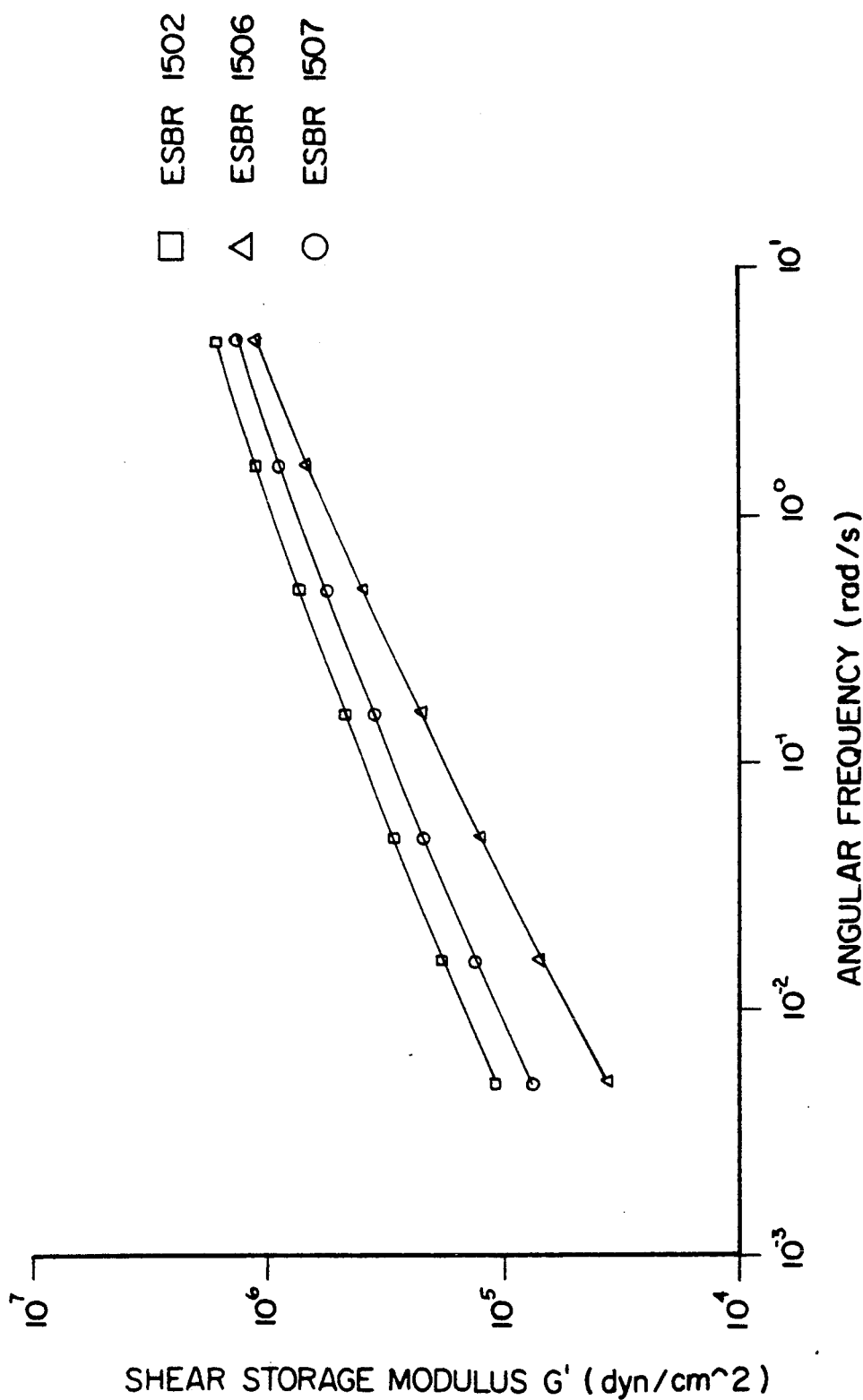
Figure 8:
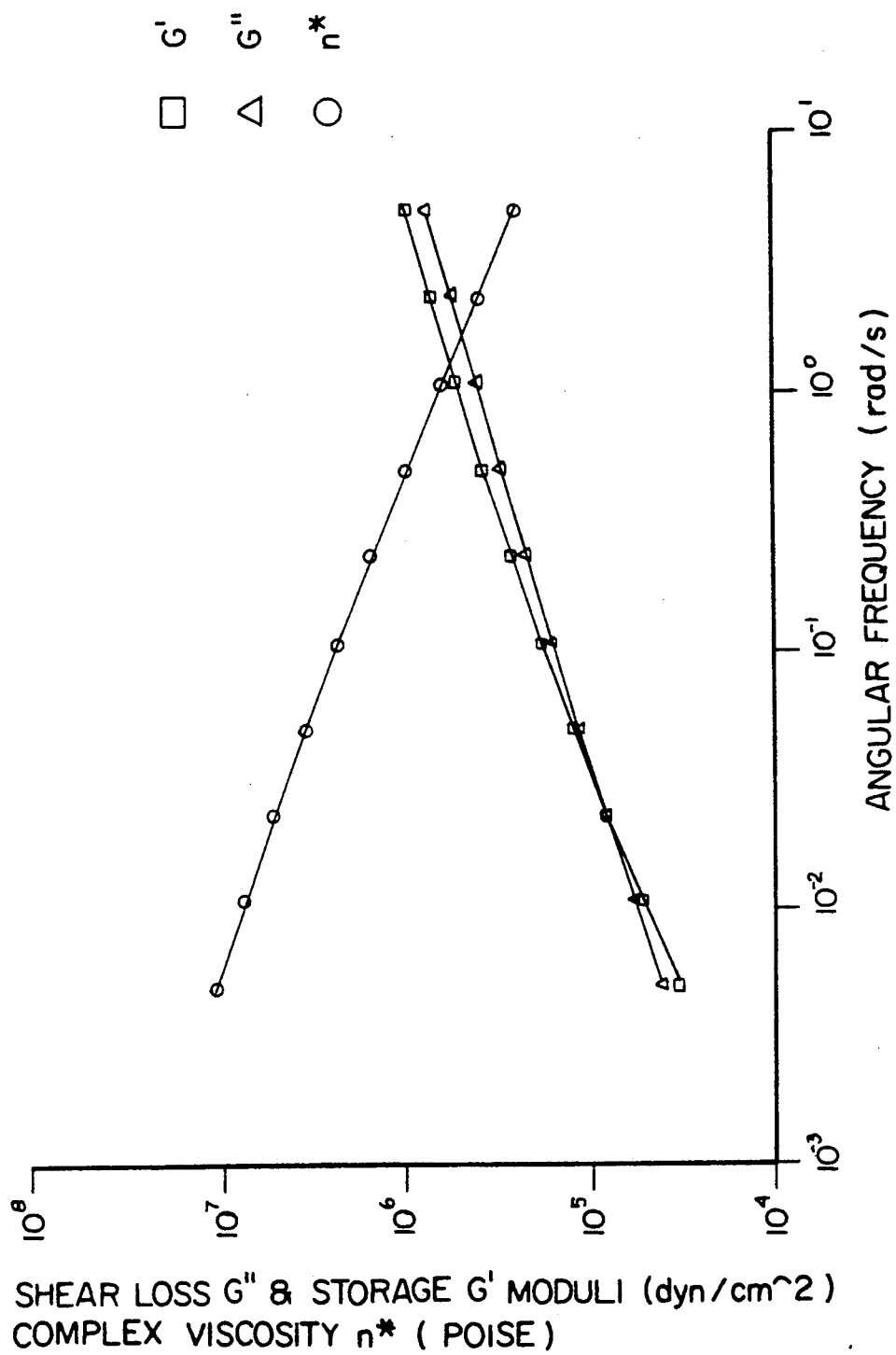
Figure 9:
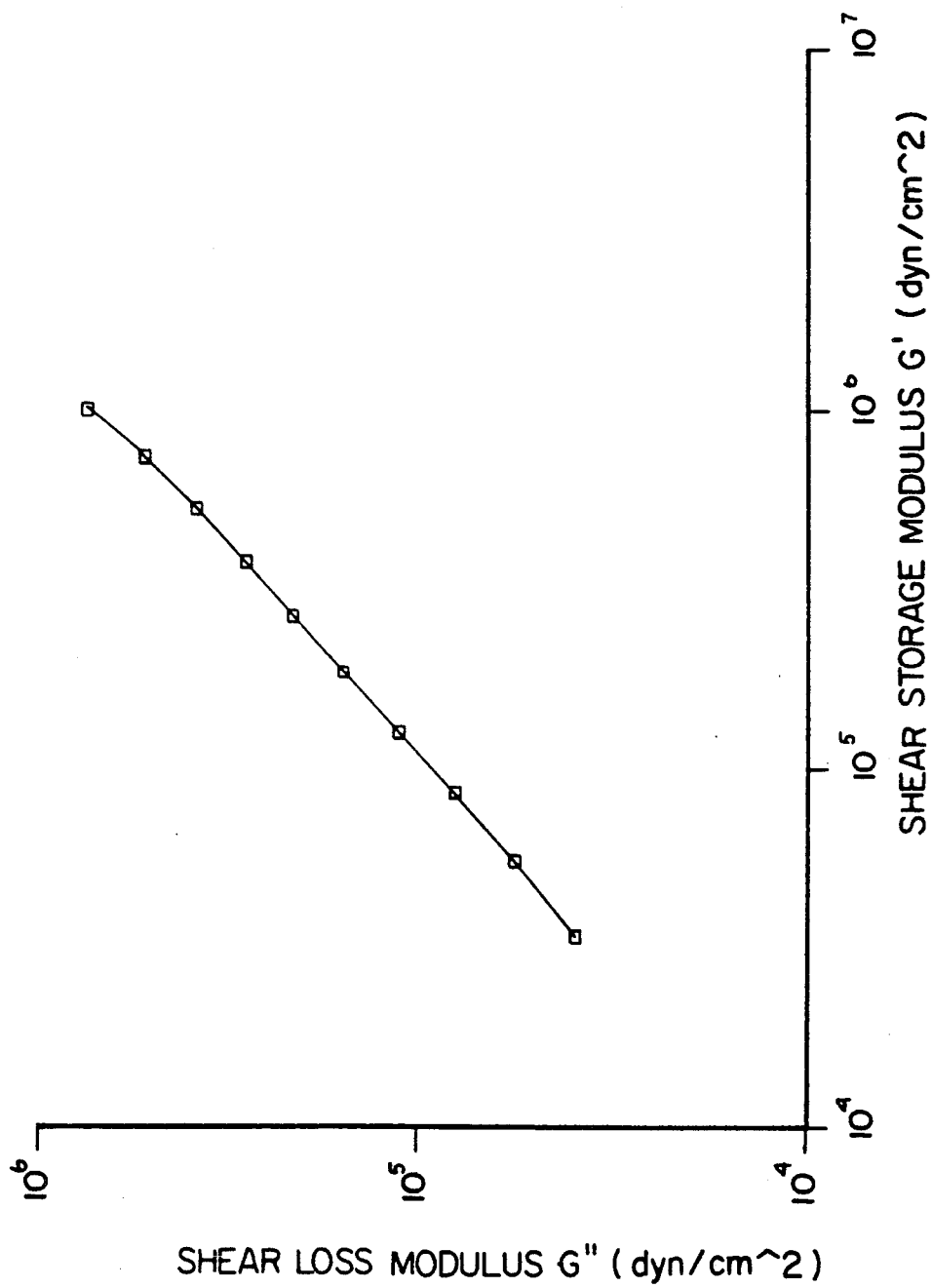

The routine then determines the minima and maxima of the log stress relaxation modulus and log time to obtain the appropriate scaling factors (912), and plots a log stress relaxation modulus vs. log time curve on the display monitor 20 (914). The operator or technician is then provided with a number of options from which to select (916), such as printing or plotting a copy of the curve, changing the degree of curve fit of the curve so as to more reasonably match the flow of the curve with the actual data points, manually entering the scaling coordinates of the plot, or continuing. (FIG. 6 illustrates typical log stress relaxation modulus vs. log time curves for three different materials.) If a selection other that continuing is made the routine will jump to the appropriate place in the routine to perform the function and then will eventually return to this menu to allow selection of another or even the same function. Note, as mentioned above, that as used in the figures an arrow pointing toward a letter or number indicates that the routine will jump to the step on the flowchart indicated by another arrow extending from the same letter or number encircled at another location on the flowcharts.

Once any rescaling, printing, etc., functions are performed as selected from the menu (916), the stress relaxation modulus vs. time data is tabulated and printed on the attached printer (918).

The polynomial coefficients as determined above (908) with the preselected or modified degree of fit are then used in an implementation of the known Yagii-Maekawa approximation to generate fundamental frequency dependent viscoelastic property information, including the loss modulus GPP(array), the storage modulus GP(array), the complex viscosity VIS(array), and the loss tangent TAND(array); each as a function of angular frequency W(array) (920).

A least square curve fit is then performed for the log base value of each of these viscoelastic properties, GPP, GP, VIS, TAND, as a function of the log based frequency W (922). The maxima and minima of the viscoelastic property data ar determined for the purposes of scaling the graphical results (924), and the property data is printed in a tabulation form on the attached printer 17 and displayed on a display monitor 20 (926). The operator is also given the option at this time of saving any of the viscoelastic properties as well as relaxation modulus versus time data and the curve fit coefficients in a series of data files (928).

A graphic plot of the loss modulus GPP, the storage modulus GP, and the complex viscosity VIS is then displayed as a function of angular frequency on the same graph on the display monitor 20 (930). The operator is then given a series of options from which further functions may be selected, such as printing or plotting the screen plot (see FIG. 8), changing the degree of fit of the curves, manually scaling the data, or simply continuing. In each case, except for when continuing is selected, the routine will jump to the appropriate instructions to perform the desired function. Those functions will be performed and eventually the options will be once again displayed (932). A Cole-Cole plot, which is a plot of the loss modulus as a function of the storage modulus, is then performed and displayed (934) (see FIG. 9.) The operator is then provided with a second set of functions from which to select, including a change in degree of fit again, performing the PROGRAM III test again with new data, entering new test information, or exiting the program all together (936).

As with PROGRAM I or PROGRAM II, a series of PROGRAM III tests may be run sequentially with very little operator interaction. For example, once the operator has closed the DSR device to the required height, the test is performed and results are generated with no further action by the operator. Once the test has been completed, the operator need only answer a few simple prompts, which among other things store the data for later analysis, to re-run the PROGRAM III test with new data. In this manner a number of tests can be performed and the results saved for future analysis by a skilled technician or engineer.

Once one or a series of PROGRAM III tests have been completed, the results may be reviewed and compared through software manipulation of stored data. Initially, this section of PROGRAM III code performs basic initiation functions such as determining the communication parameters for interface with the printer 17 or plotter 18, and characteristics of the display monitor 20 (see FIG. 29, Step 1000). The routine then prompts the user to select the comparison options desired, such as comparing the relaxation modulus or storage modulus curves for a number of previously performed tests (1002). The user is then prompted to select the data files, corresponding to previously performed tests, desired for comparison (1004). These files contain identifiers such as the file name as well as the relaxation modulus and time coordinates, the number of data points collected during the test, the degree of polynomial fit and the related coefficients for the test, and the minima and maxima of the coordinates. Depending on the options selected from Menu 3 (1002) the routine will then jump to a corresponding subroutine to perform the required functions. Note that in FIGS. 29 through 34 the comparison option selections and corresponding subroutines are identified by double letters, such as AA, BB, etc.

If the user choose to compare the relaxation modulus curves for a number of previously performed tests, the routine will jump to the appropriate subroutine (AA) and, initially, determine the maximum and minimum values amongst all the selected files to perform their appropriate scaling (1006). The routine then plots the axis and appropriate labels on the display monitor (1008) plots the relaxation modulus vs. time data coordinates for the first selected file on the graph, and then plots the relaxation modulus curve, determined by the polynomial fit coefficients on the graph (1010). Note that while the data points identified on the graph with appropriate symbols, such as squares, circles, etc., are actual collected data points from the test, the curves are a function of a least squares fit routine, and thus may not pass through the actual data points.

Once the data points and associated curve for a selected file has been completed, the plotting color and symbol are changed (1010) and the routine determines whether all the selected files and related coordinates have been plotted (1012). If not, the step of plotting the coordinates and associated curve is then repeated (1010) until all the files have been plotted on the graph. The user is then provided with the option of printing or plotting the graph shown on the display monitor, manually rescaling the graph or performing no function at all (1014). If the user chooses to manually rescale the graph, program control will return to Step (1010) to again plot the selected files. Once all the desired graphics options have been selected and completed, a second comparison options menu (Menu 3b) is displayed to allow the user to compare other properties, select new data files for comparison, or exit the program all together (1016).

Figure 31:
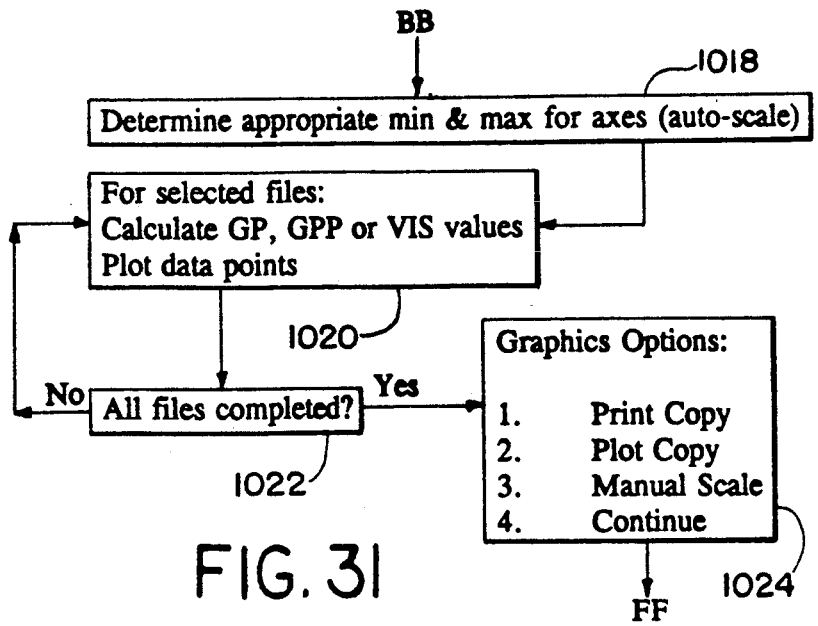

If the user selected comparisons of the storage modulus, loss modulus, or complex viscosity data from the previously performed tests in either Menu 1 or Menu 2, the routine jumps to the appropriate subroutine to handle these comparisons (BB, see FIG. 31). This routine provides the user the option of plotting one property for all of the data files on the same graph. Based on the selection the routine will then determine the appropriate minimum and maximum values based on the selected files (1018), and then, based on the scaling factor, calculate and plot the scaled points (1020). The routine then checks to determine whether all the files have been plotted on the graph (1022) and repeats the process until the graph is completed. The user is then again provided with graphics options from which to select, such as printing or plotting the displayed graph or manually rescaling the graph (1024). Upon completion of the graphics options, the second comparison options menu is then redisplayed allowing further comparisons by the user (1016).

Figure 32:
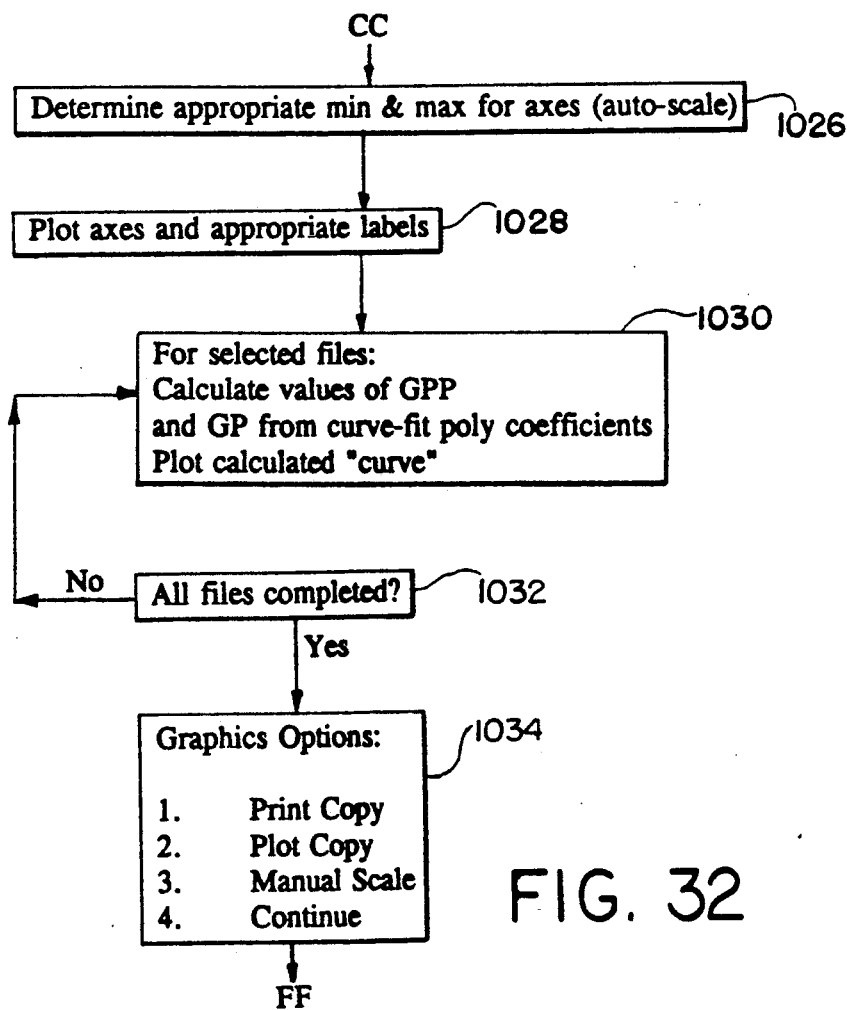
Figure 33:
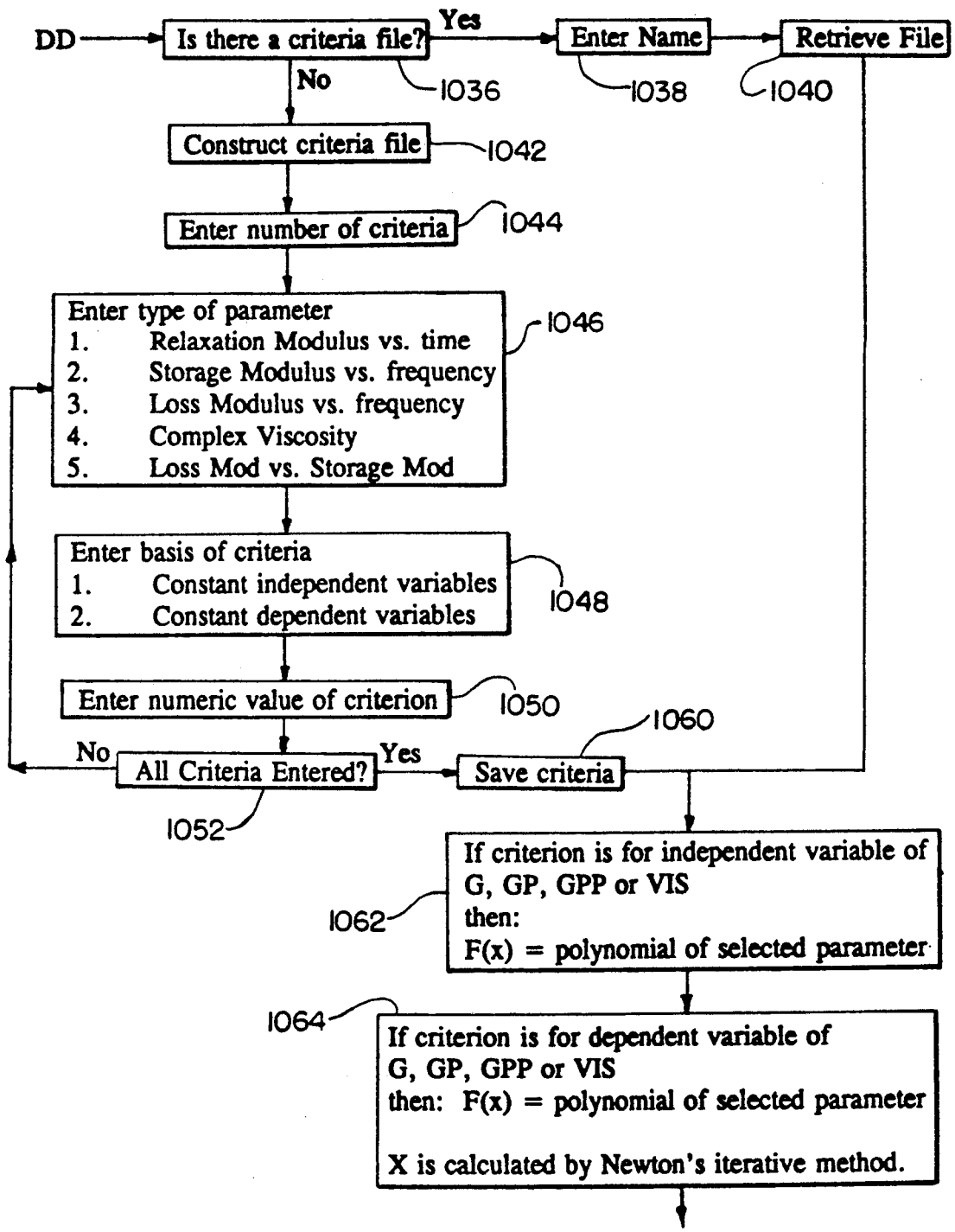
Figure 34:
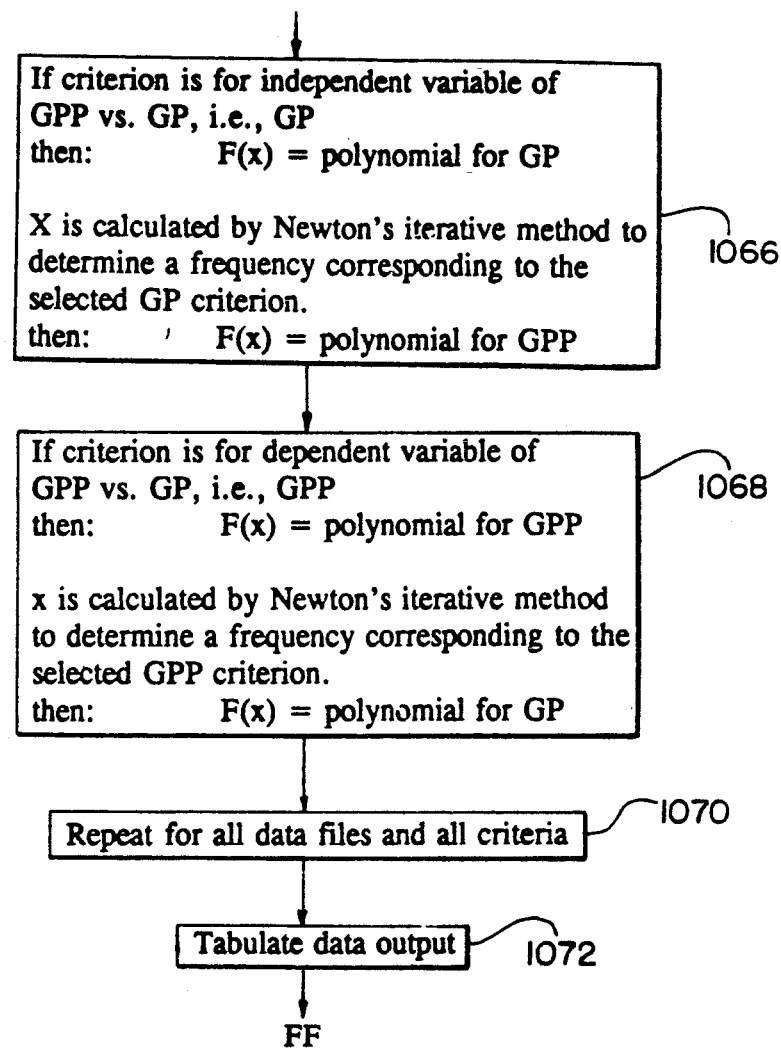

If the user has selected a COLE-COLE plot, which is a plot of the shear loss modulus as a function of the shear storage modulus, the routine will jump to the subroutine associated therewith (CC, see FIG. 32). The routine first determines the maximum and minimum values for both the loss modulus and storage modulus data points for scaling of the curve (1026). The axes are then plotted and identified with the appropriate labels (1028). Since the actual values of the loss modulus GPP and the storage modulus GP yielded from the YAGII/-

MAEKAWA conversion are a function of angular frequency, the least squares curve fit polynomial coefficients of each is used to calculate GPP as a function of GP (1030). A sufficient number of these values are determined and plotted to yield a relatively smooth curve. The points identified by symbols along the curve, consequently, are not actually test data points, but rather are convenient points along the calculated curve. This process is repeated for all the selected files until the graph is complete (1030, 1032). The user is then once again provided with graphics options from which printing, plotting or rescaling may be selected (1034). Once the graphics options have been selected and completed, program control is returned to the second comparison options menu to allow the selection of further comparisons, etc. (1016).

Another option which the user has from either of the main menus is to select the tabulated comparison criteria. This option allows the user to select a set of criteria for comparing the various samples at either constant property values or time/frequency values. The responsible routine (DD, FIG. 33) first determines whether a criteria file has already been developed (1036). If so, the user is prompted to enter the name of the criteria file (1038) and the routine will retrieve the file (1040) and then proceed to tabulate the values as discussed below. If a criteria file has not been constructed, a suitable file will be opened (1042). The user is then prompted to enter the number of criteria to be tabulated (1044), and to enter the type of parameter types from which the tabulation will be made (1046). Examples of the parameters are the relaxation modulus vs. time, storage or loss modulus vs. frequency, the complex viscosity vs. frequency or the loss modulus vs. the storage modulus. The user is then prompted to enter the basis of criteria, in other words, whether the property value to be held constant is an independent or dependent variable in the parameter type (1048). The user is then prompted to enter the numeric value of the criteria to be held constant (1050). If the total number of criteria selected have not all been entered (1052) the user is again prompted to enter the next type of parameter (1046), the basis of criteria (1048), and the numeric value of the constant criterion (1050) and all the criteria are stored (1060).

The basis for tabulating values based on the constant criterion depends on the parameter type and whether the criterion is a dependent or independent variable. If the criterion is a constant independent variable of the relaxation modulus, the storage modulus, the loss modulus, or the complex viscosity, the numeric value of the criterion is simply entered into the function of the parameter type as determined by the coefficients of the least squares polynomial, and the result is the tabulated value (1062). If the constant criterion is, however, a dependent variable of the relaxation modulus, storage modulus, loss modulus, or complex viscosity parameters, then the tabulated value for each PROGRAM III test is determined by Newton's well-known iterative method (1064). Consequently, the least squares polynomial of the selected parameter type, i.e., G, GP, GPP or VIS, is solved for the independent variable iteratively. The iterative solution is continued until the desired independent variable is calculated within a preset tolerance or the number of iterations exceeds a preset maximum, where upon a warning is issued.

If the constant criterion selected is the independent variable of the loss modulus vs. storage modulus parameter type, i.e., GP, then a two-step process is performed (1066). First, the least squared polynomial of the storage modulus vs. frequency is iteratively solved for the frequency at the constant criterion GP using Newton's iterative method. Secondly, the solved for frequency value is then entered into the least squared polynomial for the loss modulus vs. frequency, yielding the desired loss modulus tabulation.

If the selected constant criterion is the dependent variable of the loss modulus vs. storage modulus parameter type, i.e., GPP, then a two-step process is again followed (1068). In this case the least squared polynomial for the loss modulus is iteratively solved for the frequency corresponding to the selected constant GPP criterion using Newton's iterative method. Secondly, the least squared polynomial of the storage modulus vs. frequency is then solved using the frequency determined above, thus yielding the tabulated storage modulus.

One of the above processes (1062, 1064, 1066, 1068) is repeated for all the data files and all criterion until the tabulation is complete (1070). The tabulated data is then placed in the appropriate format and displaced on the display monitor (1072). The user is then again provided with the second comparison options menu to perform further comparisons, begin a new data analysis, or exit the program all together (1016).

While specific embodiments of the mechanical and electrical hardware, and the computer software structure are recited herein it will be appreciated that other embodiments and implementations that accomplish the spirit of the invention are possible and that the invention is not in any way limited to the specific embodiments discussed. For example, in some instances it may be possible to implement a system performing many of the same functions without separate dedicated and general processors, or to employ similar processing elements such as optical computers or parallel processors. In such instances it would be apparent to modify the software to operate most effectively and efficiently within the constraints and capabilities of the specific processing element or elements implemented. Further, the described embodiments, mechanics, and geometries of the DSR machine could be modified in other like ways which would impart an impulsive rotational deflection on the test specimen and detect the reactive torsional stresses developed in the test specimen.

What is claimed is:

1. An apparatus for determining the fundamental viscoelastic properties of a viscoelastic material, comprising:
   a) means for imparting a torsional stress in a viscoelastic material;
   b) means for measuring the relaxation of such torsional stress over time and converting such relaxation stress to a representative waveform; and
   c) processing means for determining the frequency dependent fundamental viscoelastic properties of such material based on the shape of a portion of such waveform.

2. The apparatus of claim 1, wherein said processing means includes a first processor for producing a digital representation of such waveform, and a second processor for determining the fundamental viscoelastic properties from a portion of such digital representation.

3. The apparatus of claim 2, wherein said first processor aborts such determination if such digital waveform is atypical of a waveform for a viscoelastic material subjected to a torsional stress.

4. The apparatus of claim 1, wherein said means for measuring and converting includes a load cell.

5. The apparatus of claim 4, wherein said load cell includes a whetstone bridge for converting mechanical stress to an electrical signal.

6. The apparatus of claim 1, wherein said means for imparting a torsional stress includes rotor means and stator means between which such viscoelastic material is compacted.

7. The apparatus of claim 6, wherein said means for imparting a torsional stress includes impulsively rotating said rotor means a predetermined angular distance.

8. The apparatus of claim 7, wherein such predetermined angular distance corresponds to 2 degrees of rotation.

9. The apparatus of claim 7, wherein such predetermined angular distance corresponds to 1 degree of rotation.

10. The apparatus of claim 7, wherein such predetermined angular distance corresponds to ½ degree of rotation.

11. The apparatus of claim 7, wherein said rotor means and said stator means include means for heating such viscoelastic material to a predetermined temperature prior to impulsively rotating said rotor means.

12. A method of determining the fundamental viscoelastic properties of a viscoelastic material, comprising the steps of:
   a) imparting a torsional stress in a viscoelastic material;
   b) measuring the relaxation of such torsional stress over time and converting such relaxation stress to a representative analog waveform;
   c) digitizing such representative analog waveform to produce a representative digital waveform; and
   d) determining the frequency dependent fundamental viscoelastic properties of such material based on the shape of a portion of such representative digital waveform.

13. The method of claim 12, wherein such representative digital waveform is a sample of evenly logarithmicly spaced in time torque amplitudes of such analog waveform.

14. The method of claim 13, wherein said step of determining includes the step of converting such torque values to time dependant shear relaxation modulus values.

15. The method of claim 14, wherein said step of converting includes multiplying such torque values by a form factor representing the geometry of the viscoelastic material under test conditions.

16. The method of claim 14, wherein said step of determining includes the step of transforming such time dependent shear stress relaxation modulus values to frequency based fundamental viscoelastic properties using the Yagii/Mukaewa approximation technique.

17. The method of claim 12, further including the step of analyzing the shape of such digital waveform to determine whether a waveform constitutes a valid test.

18. The method of claim 17, wherein said step of analyzing includes determining when in time the amplitude of such waveform has exceeded a certain threshold value, and comparing the amplitude of such waveform at a time interval later to confirm that the amplitude of such waveform is at least half of said threshold value.

* * * * *